United States Patent [19]

Ikawa et al.

[11] Patent Number: 5,286,869

[45] Date of Patent: Feb. 15, 1994

[54] 1,4-DIHYDROPYRIDINE DERIVATIVES

[75] Inventors: Hiroshi Ikawa; Akiyoshi Kadoiri, both of Tokyo; Yasuo Sekine, Kanagawa, all of Japan

[73] Assignee: Fujirebio Kabushiki Kaisha, Tokyo, Japan

[21] Appl. No.: 492,951

[22] Filed: Mar. 12, 1990

Related U.S. Application Data

[63] Continuation-in-part of Ser. No. 285,095, Dec. 15, 1988, abandoned.

[30] Foreign Application Priority Data

Jun. 17, 1989 [JP] Japan .................. 1-153591

[51] Int. Cl.$^5$ ............................ C07D 401/12
[52] U.S. Cl. ................................ 546/278
[58] Field of Search ................ 546/278, 322

[56] References Cited

U.S. PATENT DOCUMENTS 3,644,627  2/1972  Bossert ................ 514/356

FOREIGN PATENT DOCUMENTS 0094159  5/1983  European Pat. Off. .
0097821  5/1983  European Pat. Off. .
0145434  3/1984  European Pat. Off. .
0191724  1/1986  European Pat. Off. .
0257616  8/1987  European Pat. Off. .
 320984  6/1989  European Pat. Off. .
3512995 10/1985  Fed. Rep. of Germany .
8807531 10/1988  PCT Int'l Appl. .
2162513  6/1985  United Kingdom .

OTHER PUBLICATIONS

Chemical Abstracts, vol. 106, No. 5, Feb. 2, 1987 Columbus, Ohio, USA Shimizu et al. "1,4-Dihydropyridine derivatives" p. 532, column 1, abstract-No. 32861e.

Primary Examiner—Mary C. Lee
Assistant Examiner—Jacqueline Haley
Attorney, Agent, or Firm—Burgess, Ryan & Wayne

[57] ABSTRACT 1,4-Dihydropyridine derivatives of formula:

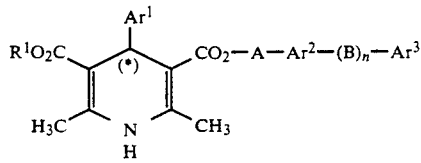

wherein $Ar^1$ represents an aromatic hydrocarbon group or an aromatic heteromonocyclic or heterobicyclic group containing therein 1 to 3 atoms selected from the group consisting of oxygen, sulfur and nitrogen; $R^1$ represents a hydrocarbon group which may have one or more substituents; A represents (i) a straight chain or branched chain unsaturated hydrocarbon group, (ii) a cyclic unsaturated hydrocarbon group, or (iii) a group selected from the group consisting of —R—O—N=CH—, —R—N=N—, —R—CH=N— and —R—N=CH—, in which R is an alkylene group having 1 to 6 carbon atoms; B represents an alkylene or alkenylene group having 1 to 3 carbon atoms, which may have a substituent; $Ar^2$ represents an aromatic hydrocarbon group or a heterocyclic group; $Ar^3$ represents a heterocyclic group which may have one or more substituents; and n is 0 or 1, and the corresponding optical active 1,4-dihydropyridine derivatives, having an optically active cite as indicated by *, have both superior vasodilative and platelet aggregation inhibiting activities.

24 Claims, No Drawings

1,4-DIHYDROPYRIDINE DERIVATIVES

This application is a continuation-in-part of application Ser. No. 07/285,095, filed Dec. 15, 1988, now abandoned.

BACKGROUND OF THE INVENTION

The present invention relates to 1,4-dihydropyridine derivatives having superior vasodilative and platelet aggregation inhibiting activities.

Many derivatives of 1,4-dihydropyridine are known, which are remedies for diseases of circulatory system such as remedies for ischemic heart disease, cerebral circulatory disease and hypertension. For example, 1,4-dihydro-2,6-dimethyl-4-(2-nitrophenyl)pyridine-3,5-dicarboxylic acid dimethyl ester (U.S. Pat. No. 3,644,627; hereinafter referred to as "NIFEDIPINE") and 1,4-dihydro-2,6-dimethyl-4-(3-nitrophenyl)pyridine-3,5-dicarboxylic acid-3-[2-(N-benzyl-N-methylamino)ethyl]ester-5-methyl ester hydrochloride (Japanese Patent Publication No. 45075/1980; hereinafter referred to as "NICARDIPINE") have already been utilized as hypotensor and coronary vasodilator. Moreover, other derivatives of 1,4-dihydropyridine having vasodilative activity together with inhibitory activity on platelet aggregation have been disclosed in Japanese Patent Applications as listed below: Japanese Patent Application Laid-open Nos. 140989/1981, 215684/1985, 226876/1985, 5076/1986, 10576/1986, 47477/1986, 197578/1986, 212581/1986 and 187468/1987.

1,4-dihydropyridine derivatives such as NIFEDIPINE and NICARDIPINE have high vasolidating activity, but they are unsatisfactory as remedy for arteriosclerosis. Therefore, researches are being made for obtaining 1,4-dihyropyridine derivatives having vasodilating activity together with platelet aggregation-inhibiting activity, capable of inhibiting platelet aggregation and curing arteriosclerosis. However, satisfactory remedies having the above-mentioned activities have not been found yet.

SUMMARY OF THE INVENTION

It is therefore an object of the present invention to provide medicines having higher inhibitory activity on platelet aggregation together with vasodilative activity.

Another object of the present invention is to provide medicines for vasodilation and inhibition of platelet aggregation, which have a low toxicity and do not exhibit significant side effects.

A further object of the present invention is to provide medicines for vasodilation and inhibition of platelet aggregation, which are particularly effective for preventing and curing arteriosclerosis.

These objects of the present invention can be achieved by 1,4-dihydropyridine derivatives having general formula (I) and optical active 1,4-dihydropyridine derivatives having general formula (II):

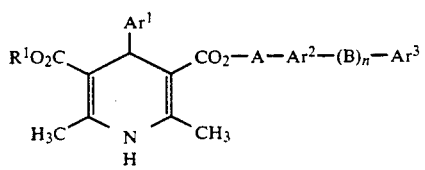
(I)

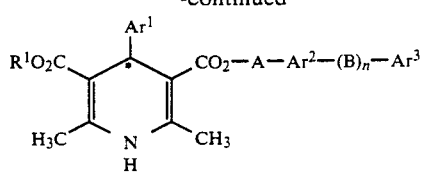
(II)

\* optically active site wherein $Ar^1$ represents an aromatic hydrocarbon group or an aromatic heteromonocyclic or heterobicyclic group containing therein 1 to 3 atoms selected from the group consisting of oxygen, sulfur and nitrogen; $R^1$ represents a hydrocarbon group which may have one or more substituents; A represents (i) a straight chain or branched chain unsaturated hydrocarbon group, (ii) a cyclic unsaturated hydrocarbon group, or (iii) a group selected from the group consisting of $-R-O-N=CH-$, $-R-N=N-$, $-R-CH=N-$, and $-R-N=CH-$, in which R is an alkylene group having 1 to 6 carbon atoms; B represents an alkylene or alkenylene group having 1 to 3 carbon atoms, which may have a substituent; $Ar^2$ represents an aromatic hydrocarbon group or a heterocyclic group; $Ar^3$ represents a heterocyclic group which may have one or more substituents; and n is 0 or 1.

DETAILED DESCRIPTION OF THE PREFERRED EMBODIMENTS

In the 1,4-dihydropyridine derivatives having the above general formula (I) and the optical active 1,4-dihydropyridine derivatives having the above general formula (II), $Ar^1$ may be an aromatic hydrocarbon group such as a phenyl group and a naphthyl group. Of these groups, a phenyl group is preferable as the aromatic hydrocarbon group represented by $Ar^1$.

Furthermore, $Ar^1$ may be an aromatic heteromonocyclic or heterobicyclic group containing therein 1 to 3 atoms selected from the group consisting of oxygen, sulfur and nigrogen (hereinafter referred to as the heterocyclic group), such as a pyridyl group, a benzoxazolyl group, a quinolyl group, a furyl group, a thienyl group, an isoquinolyl group, a benzthiazolyl, a benzoxadiazolyl and a benzthiadiazolyl. Of these groups, a pyridyl group, a benzoxazolyl group, a quinolyl group, a furyl group, and a thienyl group are preferable as the heterocyclic group represented by $Ar^1$.

The aromatic hydrocarbon groups or heterocyclic groups represented by $Ar^1$ may have one or more substituents selected from the group consisting of a nitro group, a trihalomethyl group such as trifluoromethyl and trichloromethyl, a cyano group, a halogen such as fluorine, chlorine, bromine and iodine, a phenoxy group, an amido group, a lower alkoxyl group having 1 to 4 carbon atoms, a lower alkyl group having 1 to 4 carbon atoms, a lower alkylthio group, a lower alkoxycarbonyl group, and a lower alkylcarbonyl group. Of these substituents, a nitro group, a trihalomethyl group such as trifluoromethyl and trichloromethyl, a cyano group, a halogen such as fluorine, chlorine, bromine and iodine, a phenoxy group are preferable as the substituents of the aromatic hydrocarbon groups or heterocyclic groups represented by $Ar^1$.

Specific preferred examples of the aromatic hydrocarbon group or heterocyclic group represented by $Ar^1$ are 2-nitrophenyl group, 3-nitrophenyl group, 4-nitrophenyl group, 2-cyanophenyl group, 2,3- dichlorophenyl group, 2-furyl group, 2-thienyl group, 3-thienyl group, 1-naphthyl group, 4-quinolyl group, 3-azidophenyl group, 3-trifluoromethylphenyl group, 4-methoxyphenyl group, 4-methylthiophenyl group, 3-pyridyl group, 4-methylphenyl and 3-trichloromethylphenyl group.

$R^1$ is a straight chain, branched chain or cyclic, saturated or unsaturated hydrocarbon group having 1 to 6 carbon atoms, which may have a substituent such as an alkoxyl group having 1 to 6 carbon atoms, a thioalkoxyl group, a mono- or di-substituted amino group, a halogen, a cyano group, a nitro group, a nitrato group, a hydroxyl group, a phenoxy group, a phenylthio group, a piperidino group, a pyrrolidino group, a substituted piperazinyl group, a morpholino group and a phenyl group. The phenyl substituent may further have one or two substituents selected from the group consisting of a halogen, a cyano group, a trihalomethyl group, an azido group, a disubstituted amino group, a lower alkyl group having 1 to 4 carbon atoms, a lower alkoxy group having 1 to 4 carbon atoms, a lower alkylthio group, a lower alkylcarbonyl group, a lower alkoxycarbonyl group, a carbamoyl group, a halomethyl group and a hydroxymethyl group. As the hydrocarbon group containing oxygen represented by $R^1$, an alkoxyalkyl group is preferable, and as the substituent of the hydrocarbon group represented by $R^1$, a disubstituted amino group is preferable for use in the present invention.

The nitrogen atom contained in the hydrocarbon group represented by $R^1$ may link with a group selected from the group consisting of a lower alkyl group having 1 to 3 carbon atoms, an aryl group or an aralkyl group.

Further, $R^1$ may be a group represented by $-A-Ar^2-(B)_n-Ar^3$ in which A, $Ar^2$, $Ar^3$, B and n are respectively the same as those defined previously in the general formula of the 1,4-dihydropyridine derivatives.

Preferred examples of the group represented by $R^1$ are a methyl group, an ethyl group, a propyl group, a n-butyl group, a n-pentyl group, a n-hexyl group, an isopropyl group, an isobutyl group, a cyclopentyl group, a cyclohexyl group, a propenyl group, a 2-butenyl group, a 3-butenyl group, a 2-pentynyl group, a 2,4-hexadienyl group, a 2,4-hexadiynyl group, a hexa-2-yn-4-ene group and a hexa-2-en-4-yne group.

Preferred examples of the group represented by $R^1$ containing therein an oxygen atom, a sulfur atom or a nitrogen atom are a methoxyethyl group, an ethoxyethyl group, a methoxypropyl group, an ethoxypropyl group, a methylthioethyl group, an ethylthioethyl group, a methylthiopropyl group, an ethylthiopropyl group, a phenylthioethyl group, a 2-(N-methylamino)ethyl group, a 2-(N,N-dimethylamino)ethyl group, a 2-(N-phenyl-N-methylamino)ethyl group, a 2-(N-benzyl-N-methylamino)ethyl group, a 2-(4-phenylpiperazin-1-yl)ethyl group, a 2-{4-(diphenylmethyl)-piperazinyl-}ethyl group, a 2-morpholinoethyl group a N-benzylpyrrolidin-3-yl group and an N-benzylpiperidin-3-yl group.

A represents (i) a straight chain or branched chain unsaturated hydrocarbon group, preferably a straight chain or branched hydrocarbon having 3 to 12 carbon atoms, (ii) a cyclic unsaturated hydrocarbon group, preferably a cyclic unsaturated hydrocarbon having 4 to 12 carbon atoms, preferably in which unsaturated hydrocarbon groups, at least an unsaturated bond thereof is conjugated with the aromatic hydrocarbon or heterocyclic group represented by $Ar^2$, or (iii) a group selected from the group consisting of $-R-O-N=CH-$, $-R-N=N-$, $-R-CH=N-$ and $-R-N=CH-$, in which R is an alkylene group having 1 to 6 carbon atoms.

The hydocarbon groups represented by A may have a substituent selected from the group consisting of a halogen, a phenyl group, a pyridyl group, a thienyl group, a furyl group, a cyano group, an alkylcarbonyl group and an alkoxycarbonyl group.

Preferred examples of the group represented b A are as follows:

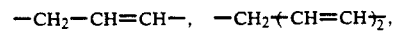

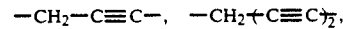

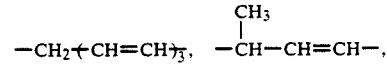

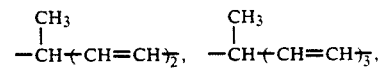

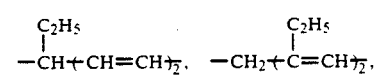

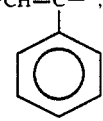

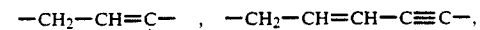

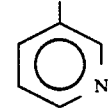

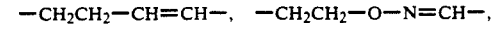

$-CH_2CH_2-CH=CH-$, $-CH_2CH_2-O-N=CH-$, $-CH_2CH_2-N=CH-$, $-CH_2CH_2CH=N-$, $-CH_2CH_2-N=N-$, and $-CH_2-C\equiv C-CH=CH-$.

$Ar^2$ may be o-, m- or p-phenylene group, a furandiyl group, a thiophenediyl group, a pyridinediyl group or a pyrrolediyl group, or $Ar^2$ may be linked with A by a methylene group, an ethylene group, a vinyl group, an oxygen atom, a sulfur atom or an amino group to form a 5- or 6-membered condensed ring.

Preferred examples of the group represented by Ar² are as follows:

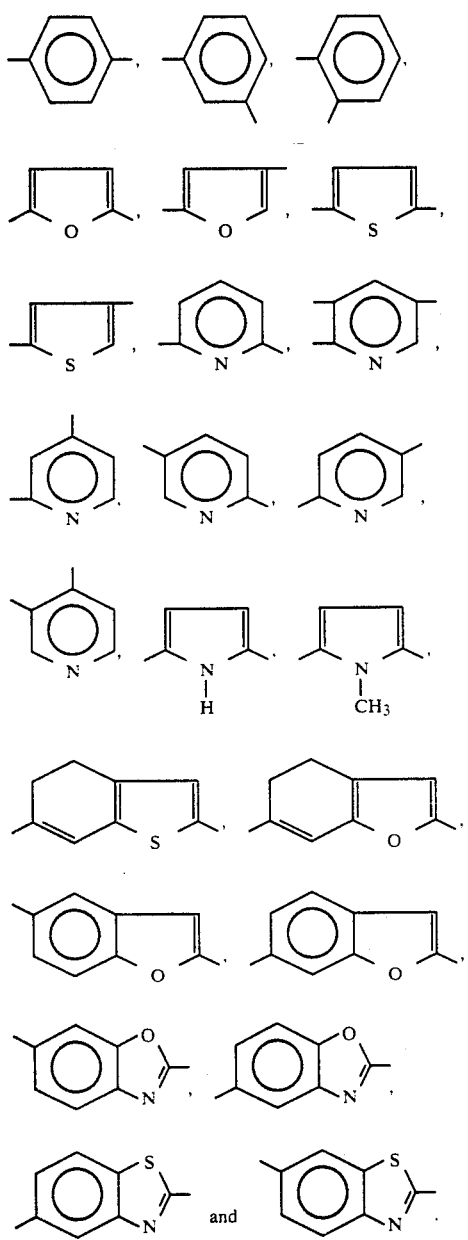

B may be an alkylene or alkenylene group having 1 to 3 carbon atoms, which may have a substituent selected from the group consisting of a lower alkyl group having 1 to 4 carbon atoms, a cyclic alkyl group, an aryl group and an aralkyl group.

Preferred examples of the group represented by B are a methylene group, an ethylene group, a trimethylene group, an ethylidene group, a benzylidene group, a vinylene group, a cyclohexylmethylene group and a 2-phenylethylidene group.

Ar³ may be a heterocyclic group with five or six members containing therein at least one atom selected from the group consisting of nitrogen, oxygen and sulfur. Preferred examples of the group represented by Ar³ are a 2-pyrrolyl group, a 2-pyridyl group, a 3-pyridyl group, a 4-pyridyl group, an imidazolyl group, a 2-oxazolyl group, a 4-oxazolyl group, a 2-thiazolyl group, a triazolyl group and a tetrazolyl group.

B may be linked with Ar² or Ar³ by a methylene group, an ethylene group, a vinylene group, an oxygen atom, a sulfur atom or a nitrogen atom to form a ring with five or six members, such as

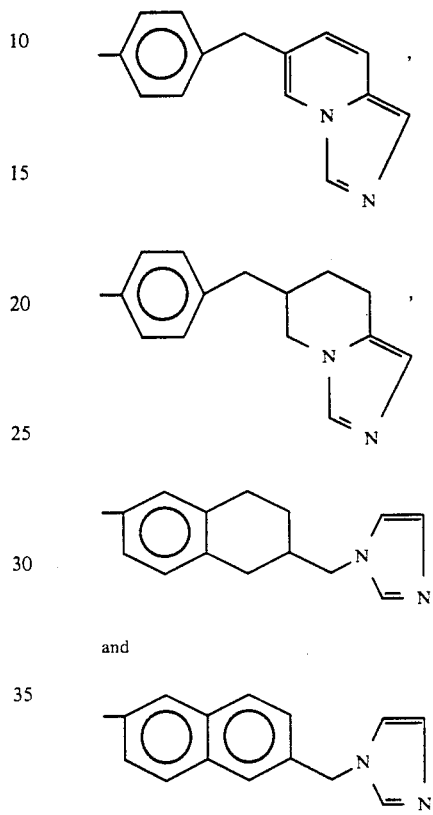

and

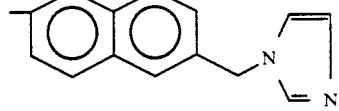

Specific examples of 1,4-dihyropyridine derivative having the general formula (I) are as follows:

3-[4-(1-imidazolylmethyl)phenyl]-2-propen-1-yl methyl 1,4-dihydro-2,6-dimethyl-4-phenylpyridine-3,5-dicarboxylate, 3-[4-(1-imidazolylmethyl)phenyl]-2-propen-1-yl methyl 4-(3-azidophenyl)-1,4-dihydro -2,6-dimethylpyridine-3,5-dicarboxylate, 3-[4-(1-imidazolylmethyl)phenyl]-2-propen-1-yl methyl 1,4-dihydro-2,6-dimethyl-4-(3-trichloromethylphenyl)pyridine-3,5-dicarboxylate, 3-[4-(1-imidazolylmethyl)phenyl]-2-propen-1-yl methyl 4-(3-cyanophenyl)-1,4-dihydro -2,6-dimethylpyridine-3,5-dicarboxylate, 3-[4-(1-imidazolylmethyl)phenyl]-2-propen-1-yl methyl 1,4-dihydro-2,6-dimethyl-4-(3-methylphenyl)pyridine-3,5-dicarboxylate, 3-[4-(1-imidazolylmethyl)phenyl]-2-propen-1-yl methyl 1,4-dihydro-2,6-dimethyl-4-(3-methoxyphenyl)pyridine-3,5-dicarboxylate, 3-[4-(1-imidazolylmethyl)phenyl]-2-propen-1-yl methyl 1,4-dihydro-2,6-dimethyl-4-(4-methythiophenyl)pyridine-3,5-dicarboxylate, 3-[4-(1-imidazolylmethyl)phenyl]-2-propen-1-yl methyl 1,4-dihydro-2,6-dimethyl-4-(3-hydroxyphenyl)pyridine-3,5-dicarboxylate, 3-[4-(1-imidazolylmethyl)phenyl]-2-propen-1-yl methyl 4-(3-benzyloxyphenyl)-1,4-dihydro -2,6-dimethylpyridine-3,5-dicarboxylate, 3-[4-(1-imidazolylmethyl)phenyl]-2-propen-1-yl methyl 4-(3-cinnamyloxyphenyl)-1,4-dihydro-2,6-dimethylpyridine-3,5-dicarboxylate, 3-[4-(1-imidazolylmethyl)phenyl]-2-propen-1-yl methyl 4-(3-benzoylphenyl)-1,4-dihydro -2,6-dimethylpyridine-3,5-dicarboxylate, 3-[4-(1-imidazolylmethyl)phenyl]-2-propen-1-yl methyl 4-(3-chlorophenyl)-1,4-dihydro -2,6-dimethylpyridine-3,5-dicarboxylate, 3-[4-(1-imidazolylmethyl)phenyl]-2-propen-1-yl methyl 1,4-dihydro-2,6-dimethyl-4-(3-fluorophenyl)pyridine-3,5-dicarboxylate, 3-[4-(1-imidazolylmethyl)phenyl]-2-propen-1-yl methyl 1,4-dihydro-2,6-dimethyl-4-(2-nitrophenyl)pyridine-3,5-dicarboxylate, 3-[4-(1-imidazolylmethyl)phenyl]-2-propen-1-yl methyl 1,4-dihydro-2,6-dimethyl-4-(3-nitrophenyl)pyridine-3,5-dicarboxylate, 3-[4-(1-imidazolylmethyl)phenyl]-2-propen-1-yl methyl 1,4-dihydro-2,6-dimethyl-4-(4-nitrophenyl)pyridine-3,5-dicarboxylate, 3[-4-(1-imidazolylmethyl)phenyl]-2-propen-1-yl methyl 4-(3-bromophenyl)-1,4-dihydro -2,6-dimethylpyridine-3,5-dicarboxylate, 3[-4-(1-imidazolylmethyl)phenyl]-2-propen-1-yl methyl 1,4-dihydro-2,6-dimethyl-4-(3-iodophenyl)pyridine-3,5-dicarboxylate, 3-[4-(1-imidazolylmethyl)phenyl]-2-propen-1-yl methyl 4-(2-chloro-3-nitrophenyl) -1,4-dihydro-2,6-dimethylpyridine-3,5-dicarboxylate, 3-[4-(1-imidazolylmethyl)phenyl]-2-propen-1-yl methyl 1,4-dihydro-2,6-dimethyl-4-(2-fluoro-3-nitrophenyl)pyridine-3,5-dicarboxylate, 3-[4-(1-imidazolylmethyl)phenyl]-2-propen-1-yl methyl 4-(3-chloro-2-fluorophenyl) -1,4-dihydro-2,6-dimethylpyridine-3,5-dicarboxylate, 3-[4-(1-imidazolylmethyl)phenyl]-2-propen-1-yl methyl 1,4-dihydro-2,6-dimethyl-4-(2,3-difluorophenyl)pyridine-3,5-dicarboxylate, 3-[4-(1-imidazolylmethyl)phenyl]-2-propen-1-yl methyl 1,4-dihydro-2,6-dimethyl-4-(2-furyl)pyridine-3,5-dicarboxylate, 3-[4-(1-imidazolylmethyl)phenyl]-2-propen-1-yl methyl 1,4-dihydro-2,6-dimethyl-4 -(3-furyl)pyridine-3,5-dicarboxylate, 3[-4-(1-imidazolylmethyl)phenyl]-2-propen-1-yl methyl 1,4-dihydro-2,6-dimethyl-4-(2-thienyl)pyridine-3,5-dicarboxylate, 3-[4-(1-imidazolylmethyl)phenyl]-2-propen-1-yl methyl 1,4-dihydro-2,6-dimethyl-4-(3-thienyl)pyridine-3,5-dicarboxylate, 3-[4-(1-imidazolylmethyl)phenyl]-2-propen-1-yl methyl 1,4-dihydro-2,6-dimethyl-4-(1-naphthyl)pyridine-3,5-dicarboxylate, 3[-4-(1-imidazolylmethyl)phenyl]-2-propen-1-yl methyl 1,4-dihydro-2,6-dimethyl-4-(1-isoquinolyl)pyridine-3,5-dicarboxylate, 3-[4-(1-imidazolylmethyl)phenyl]-2-propen-1-yl methyl 1,4-dihydro-2,6-dimethyl-4-(2-quinoxalyl)pyridine-3,5-dicarboxylate, 3-[4-(1-imidazolylmethyl)phenyl]-2-propen-1-yl methyl 4-(2-chloropyridyl)-1,4-dihydro -2,6-dimethylpyridine-3,5-dicarboxylate, 3-[4-(1-imidazolylmethyl)phenyl]-2-propen-1-yl methyl 1,4-dihydro-2,6-dimethyl-4-(2-methylpyridyl)pyridine-3,5-dicarboxylate, 3-[4-(1-imidazolylmethyl)phenyl]-2-propen-1-yl methyl 1,4-dihydro-2,6-dimethyl-4-(2-methoxypyridyl)pyridine-3,5-dicarboxylate, 3[-4-(1-imidazolylmethyl)phenyl]-2-propen-1-yl methyl 4-(5-bromopyridyl)-1,4-dihydro -2,6-dimethylpyridine-3,5-dicarboxylate, 3-[4-(1-imidazolylmethyl)phenyl]-2-propen-1-yl methyl 4-(2-aminopyridyl)-1,4-dihydro -2,6-dimethylpyridine-3,5-dicarboxylate, 3-[4-(1-imidazolylmethyl)phenyl]-2-propen-1-yl methyl 1,4-dihydro-2,6-dimethyl-4-(2-mercaptopyridyl)pyridine-3,5-dicarboxylate, 3-[4-(1-imidazolylmethyl)phenyl]-2-propen-1-yl methyl 1,4-dihydro-2,6-dimethyl-4-(3-pyridazinyl)pyridine-3,5-dicarboxylate, 3-[4-(1-imidazolylmethyl)phenyl]-2-propen-1-yl methyl 1,4-dihydro-2,6-dimethyl-4-pyrazinylpyridine-3,5-dicarboxylate, 3[-4-(1-imidazolylmethyl)phenyl]-2-propen-1-yl methyl 1,4-dihydro-2,6-dimethyl-4-(2-pyrimidyl)pyridine-3,5-dicarboxylate, 3-[4-(1-imidazolylmethyl)phenyl]-2-propen-1-yl methyl 4-(7-benzoxazolyl)-1,4-dihydro -2,6-dimethylpyridine-3,5-dicarboxylate, 3-[4-(1-imidazolylmethyl)phenyl]-2-propen-1-yl methyl 4-(7-benzothiazolyl)-1,4-dihydro -2,6-dimethylpyridine-3,5-dicarboxylate, 3-[4-(1-imidazolylmethyl)phenyl]-2-propen-1-yl methyl 4-(2, 1,3-benzoxadiazole-3-yl)-1,4-dihydro-2,6-dimethylpyridine-3,5-dicarboxylate, 3[-4-(1-imidazolylmethyl)phenyl]-2-propen-1-yl methyl 4-(2, 1,3-benzothiadiazole-3-yl)-1,4-dihydro-2,6-dimethylpyridine-3,5-dicarboxylate, 3-[4-(1-imidazolylmethyl)phenyl]-2-propen-1-yl methyl 1,4-dihydro-2,6-dimethyl-4-(3-indolyl)pyridine-3,5-dicarboxylate, 3-[4-(1-imidazolylmethyl)phenyl]-2-propen-1-yl methyl 1,4-dihydro-2,6-dimethyl-4-(2,3,4-trimethoxyphenyl)pyridine-3,5-dicarboxylate, 3-[4-(1-imidazolylmethyl)phenyl]-2-propen-1-yl methyl 1,4-dihydro-2,6-dimethyl-4-(2,3,4-trifluorophenyl)-pyridine-3,5-dicarboxylate, 3-[4-(1-imidazolylmethyl)phenyl]-2-propen-1-yl methyl 1,4-dihydro-2,6-dimethyl-4-(2,3,6-trichlorophenyl)-pyridine-3,5-dicarboxylate, 3[-4-(1-imidazolylmethyl)phenyl]-2-propen-1-yl methyl 1,4-dihydro-2,6-dimethyl-4-(2,4,6-trimethylphenyl)-pyridine-3,5-dicarboxylate, 3[-4-(1-imidazolylmethyl)phenyl]-2-propen-1-yl methyl 1,4-dihydro-2,6-dimethyl-4-(3,4,5-triethoxyphenyl)-pyridine-3,5-dicarboxylate, 3[-4-(1-imidazolylmethyl)phenyl]-2-propen-1-yl methyl 4-(2-chloro-3,5-dinitrophenyl) -1,4-dihydro-2,6-dimethylpyridine-3,5-dicarboxylate, 3-[4-(1-imidazolylmethyl)phenyl]-2-propen-1-yl methyl 1,4-dihydro-2,6-dimethyl-4-(3-methyl-2-thienyl)-pyridine-3,5-dicarboxylate, 3-[4-(1-imidazolylmethyl)phenyl]-2-propen-1-yl methyl 1,4-dihydro-2,6-dimethyl-4-(2-cyanophenyl)pyridine-3,5-dicarboxylate, 3-[4-(1-imidazolylmethyl)phynyl]-2-propen-1-yl methyl 1,4-dihydro-2,6-dimethyl-4-(3-trifluoromethylphenyl)pyridine-3,5-dicarboxylate, 3-[4-(1-imidazolylmethyl)phenyl]-2-propen-1-yl methyl 1,4-dihydro-2,6-dimethyl-4-(2,3-dichlorophenyl)-pyridine-3,5-dicarboxylate, 3-[4-(1-imdazolylmethyl)phenyl]-2-propen-1-yl methyl 1,4-dihydro-2,6-dimethyl-4-(4-quinolyl)pyridine-3,5-dicarboxylate, 3-[4-(1-imidazolylmethyl)phenyl]-2-propen-1-yl mehyl 1,4-dihydro-2,6-dimethyl-4-(3-pyridyl)pyridine-3,5-dicarboxylate, methyl 3-[4-(1,2,3,4-tetrazol-1-ylmethyl)phenyl]-2-propen-1-yl 1,4-dihydro-2,6-dimethyl-4-(3-nitrophenyl)-pyridine-3,5-dicarboxylate, methyl 3-[4-(1,2,4-triazol-1-ylmethyl)phenyl]-2-propen-1-yl 1,4-dihydro-2,6-dimethyl-4-(3-nitrophenyl)pyridine-3,5-dicarboxylate, 3-[4-(1,3,4-triazol-1-ylmethyl)phenyl]-2-propen-1-yl 1,4-dihydro-2,6-dimethyl-4-(3-nitrophenyl)pyridine-3,5-dicarboxylate, methyl 3-[4-(3-pyridylmethyl)phenyl]-2-propen-1-yl 1,4-dihydro-2,6-dimethyl-4-(3-nitrophenyl)-pyridine-3,5-dicarboxylate, 3[-4-(1-imidazolyl)phenyl]-2-propen-1-ylmethyl 1,4-dihydro-2,6-dimethyl-4-(3-nitrophenyl)pyridine-3,5-dicarboxylate, 3-[6-(1-imidazolylmethyl)pyridine-2-yl]-2-propen-1-yl methyl 1,4-dihydro-2,6-dimethyl-4-(3-nitrophenyl)-pyridine-3,5-dicarboxylate, 3-[3-(1-imidazolylmethyl)phenyl]-2-propen-1-yl methyl 1,4-dihydro-2,6-dimethyl-4-(3-nitrophenyl)pyridine-3,5-dicarboxylate, 3[-2-(1-imidzolylmethyl)phenyl]-2-propen-1-yl methyl 1,4-dihydro-2,6-dimethyl-4-(3-nitrophenyl)pyridine-3,5-dicarboxylate, 3-[5-(1-imidazolylmethyl)-2-thiophene]-2-propen 1-yl methyl-1,4-dihydro-2,6-dimethyl -4-(3-nitrophenyl)-pyridine-3,5-dicaboxylate, 3[-5-(1-imidzolylmethyl)-2-furan]-2-propen-1-yl methyl 1,4-dihydro-2,6-dimethyl-4-(3-nitrophenyl)pyridine-3,5-dicarboxylate, 6-(1-imidzolylmethyl)benzoxazol-2-yl-methyl methyl 1,4-dihydro-2,6-dimethyl-4(3-nitrophenyl) pyridine-3,5-dicarboxylate, isopropyl 3-[4-(1-imidazolylmethyl)phenyl]-2-propen-1-yl 1,4-dihydro-2,6-dimethyl-4-(3-nitrophenyl)pyridine-3,5-dicarboxylate, di-3-[4-(1-imidazolylmethyl)phenyl]-2-propen-1-yl 1,4-dihydro-2,6-dimethyl-4-(3-nitrophenyl)pyridine-3,5-dicarboxylate, 5-[4-(1-imidazolylmethyl)phenyl]-2,4-pentadien-1-yl methyl-1,4-dihydro-2,6-dimethyl-4-(3-nitrophenyl)-pyridine-3,5-dicarboxylate, 3[-4-(1-imidazolylmethyl)phenyl]-2-propen-1-yl 2-methoxyethyl 1,4-dihydro-2,6-dimethyl -4-(3-nitrophenyl)-yridine-3,5-dicarboxylate, 2,4-hexadien-1-yl 3-[4-(1-imidazolylmethyl)phenyl]2-propen-1-yl 1,4-dihydro-2,6-dimethyl-4-(3-nitrophenyl)pyridine-3,5-dicarboxylate, cinnamyl 3-[4-(1-imidazolylmethyl)phenyl]-2-propen-1-yl 1,4-dihydro-2,6-dimethyl-4-(3-nitrophenyl)pyridine-3,5-dicarboxylate, ethyl 3-[4-(1-imidazolylmethyl)phenyl]-2-propen-1-yl 1,4-dihydro-2,6-dimethyl-4-(3-nitrophenyl)pyridine-3,5-dicarboxylate, 5-[4-(1-imidazolylmethyl)phenyl]-pent-3-en-4-yne-1-yl methyl 1,4-dihydro-2,6-dimethyl-4-(3-nitrophenyl)-pyridine-3,5-dicarboxylate, 3-[4-(1-imidazolylmethyl)phenyl]-2-propyne-1-yl methyl 1,4-dihydro-2,6-dimethyl-4-(3-nitrophenyl)-pyridine-3,5-dicarboxylate, 4-[4-(1-imidazolylmethyl)phenyl]-3-buten-2-yl methyl 1,4-dihydro-2,6-dimethyl-4-(3-nitrophenyl)pyridine-3,5-dicarboxylate, 4-[4-(1-imidazolylmethyl)phenyl]-3-buten-1-yl methyl 1,4-dihydro-2,6-dimethyl-4-(3-nitrophenyl)pyridine-3,5-dicarboxylate, 3-[4-{1-(1-imidazolyl)ethyl}phenyl]-2-propen-1-yl methyl 1,4-dihydro-2,6-dimethyl-4-(3-nitrophenyl)-pyridine 3,5-dicarboxylate, 3-[4-(1-imidazolylmethyl)phenyl]-2-fluoro-2-propen-1-yl methyl 1,4-dihydro-2,6-dimethyl-4-(3-nitrophenyl)pyridine-3,5-dicarboxylate, 3-[4-(1-imidazolylmethyl)phenyl]-2-methyl-2-propen-1-yl methyl 1,4-dihydro-2,6-dimethyl-4-(3-nitrophenyl)pyridine-3,5-dicarboxylate, 3-[4-(1-imidazolylmethyl)phenyl]-2-buten-1-yl methyl 1,4-dihydro-2,6-dimethyl-4-(3-nitrophenyl)pyridine-3,5-dicarboxylate, 2-[4-(1-imidazolylmethyl)benzylideneamino]ethyl methyl 1,4-dihydro-2,6-dimethyl-4-(3-nitrophenyl)-pyridine-3,5-dicarboxylate, and 2-[{4-(l-imidazolylmethyl)benylideneamino}oxy]ethyl-methyl-1,4-dihydro-2,6-dimethyl-4-(3-nitrophenyl)-pyridine-3,5-dicarboxylate.

Process For Preparation Of 1,4-Dihydropyridine Derivatives 1,4-dihydropyridine derivatives having the general formula (I) can be prepared by either Process 1 or Process 2 as shown below:

Process 1

Esters having the general formula (I-1):

$$CH_3COCH_2COOR^1 \qquad (I\text{-}1)$$

are allowed to react with aldehydes having general formula (I-2):

$$Ar^1\text{—}CHO \qquad (I\text{-}2)$$

and then are allowed to react with β-aminoacrylic acid ester having general formula (I-3):

$$CH_3(NH_2)C=CH\text{—}COOA\text{—}Ar^2\text{—}B\text{—}Ar^3 \qquad (I\text{-}3)$$

wherein $R^1$, $Ar^1$, A, B, $Ar^2$ and $Ar^3$ are the same as those as shown in the above.

Esters having the general formula (I-1) include methyl acetoacetate, ethyl acetoacetate, isopropyl acetoacetate, 2-methoxyethyl acetoacetate, 2-cyanoethyl acetoacetate, 3-phenyl-2-propen-1-yl acetoacetate, 2,4-hexadiene cetoacetate, 3-{4-(1-imidazolylmethyl)-phenyl}-2-propen-1-yl acetoacetate, 2-(N-benzyl-N-methylamino)ethyl acetoacetate, N-benzylpiperidin-3-yl acetoacetate and N-benzyl-pyrrolidin-3-yl acetoacetate.

Aldehydes having the general formula (I-2) include 2-nitrobenzaldehyde, 3-nitrobenzaldehyde, 4-nitrobenzaldehyde, 3-trifluoromethylbenzaldehyde, 3-azidobenzaldehyde, 3-pyridinecarboxaldehyde, 4-quinolinecarboxaldehyde, 2-cyanobenzaldehyde, 2,3-dichlorobenzaldehyde, furfural, 2-thiophenecarboxaldehyde, 3-thiophenecarhoxaldehyde, 4-methoxybenzaldehyde, 4-methylthiobenzaldehyde and 4-tolualdehyde.

β-aminoacrylic esters having general formula (I-3) include 3-{4-(1-imidazolylmethyl)phenyl}-2-propen-1-yl aminocrotonate, 3-{4-(pyridin-3-yl-methyl)-phenyl}-2-propen-1-yl aminocrotonate, 3-{4-(1,2,4-triazol-1-yl-methyl) phenyl)-2-propen-1-yl aminocrotonate, 3-{4-(1,2,3,4-tetrazol-1-yl-methyl)phenyl}-2-propen -1-yl aminocrotonate, 3-{2-(1-imidazolylmethyl)-phenyl}-2-propen-1-yl aminocrotonate, 3-{3-(1-imidazolyl-methyl)phenyl}-2-propen-1-yl amino-crotonate, 3-{5-(1-imidazolylmethyl) furan}-2-propen-1-yl aminocrotonate, 3-{5-(1-imidazolylmethyl)thiophene)-2-propen-1-yl aminocrotonate 3-{5-(1-imidazolylmethyl)pyridine)-2-propen-1-yl aminocrotonate, 3-{2-(1-imidazolyl-methyl)-1-methyl-pyrrol-5-yl}-2-propen-1-yl aminocrotonate, 3-[4-{1-(1-imidazolyl)ethyl} phenyl]-2-propen-1-yl aminocrotonate, 3-{4-(1-imidazolyl)phenyl)-2-propen-1-yl aminocrotonate, 3-{4-(l-imidazolylmethyl) phenyl}-2-propen-1-yl aminocrotonate, 5-{4-(1-imidazolylmethyl)phenyl}-2,4-pentadien-1-yl aminocrotonate, 4,5-dihydro-2-(1-imidazolyl)methyl thianaphten-6-yl methyl aminocrotonate, 4,5-dihydro-2-{α-(1-imidazolyl)benzyl} thianaphten-6-yl methyl amino-crotonate and 3-{4-(imidazo[1,2-a]pyridin-6-yl-methyl)phenyl}-2-propen-1yl aminocrotonate.

The reactions are carried out in an inactive solvent such as methanol, ethanol, propanol, isopropanol, benzene, toluene, dioxane, tetrahydrofuran, dimethyl sulfoxide and dimethylformamide at temperatures of 50° C. to 150° C.

Process 2

Carboxylic acid or carboxylic acid derivatives having the following general formula (I-4)

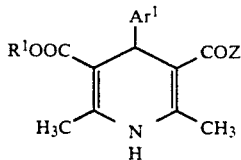

are allowed to react with alcohol derivatives having the following general formula (I-5)

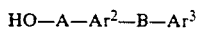

wherein $R^1Ar^1$, A, B, $Ar^2$ and $Ar^3$ are the same as those as shown in the above, and Z is a hydroxyl group, a halogen atom, a methylsulfonyloxy group or a benzotriazol-1-oxy group.

Carboxylic acid and derivatives thereof having the general formula (I-4) can be easily obtained by the conventional process (for instance, described in Chemical Pharmaceutical Bulletin, 28 2809 (1980)).

The carboxylic acid derivatives having general formula (I-4) include 1,4-dihydro-2,6-dimethyl-5-methoxycarbonyl-4-(3-nitrophenyl)pyridine-3-carboxylic acid, 1,4-dihydro-2,6-dimethyl-5-methoxycarbonyl-4-(3-nitrophenyl)pyridine-3-carboxylic acid chloride, 1,4-dihydro-2,6-dimethyl-5-ethoxycarbonyl-4-(3-nitrophenyl)pyridine-3-carboxylic acid chloride, 1,4-dihydro-2,6-dimethyl-5-isopropyloxycarbonyl-4-(3-nitrophenyl)pyridine-3-carboxylic acid chloride, 1,4-dihydro-2,6-dimethyl-5-(2,4-hexadien-1-yl)oxycarbonyl-4-(3-nitrophenyl)pyridine -3-carboxylic acid chloride, 1,4-dihydro-2,6-dimethyl-5-(3-phenyl-2-propen-1-yl)oxycarbonyl-4-(3-nitrophenyl) pyridine-3-carboxylic acid chloride and 1,4-dihydro-2,6-dimethyl-5-[3-{4-(1-imidazolylmethyl)phenyl}-2-propen -1-yl]oxycarbonyl-4-(3-nitrophenyl)pyridine-3-carboxylic acid chloride.

Alcohol derivatives having the general formula (I-5) are easily available and such alcohol derivatives include 3-{4-(1-imidazolylmethyl)phenyl}-2-propen-1-ol, 3-{4-(3-pyridylmethyl)phenyl} -2-propen-1-ol, 3-{14-(1,2,4-triazol-1-yl-methyl)phenyl}-2-propen-1-ol, 3-{4-(1,2,3,4-tetrazol-1-yl-methyl)phenyl}-2-propen-1-ol, 3-{2-(1-imidazolylmethyl)-phenyl}-2-propen-1-ol, 3-{3-(1-imidazolylmethyl)phenyl)-2-propen-1-ol, 3-{5-(1-imidazolylmethyl)furan}-2-propen-1-ol, 3-{5-(1-imidazolylmethyl)thiophene)-2-propen-1-ol, 3-{2-(1-imidazolylmethyl)-1-methylpyrrol-5-yl}-2-propen-1-ol, 3-[4-{1-(1-imidazolyl)ethyl]phenyl]-2-propen-1-ol, 3-{4-(1-imidazolyl)phenyl}-2-propen-1-ol, 3-{4-(1-imidazolylmethyl)phenyl)-2-propyn-1-ol, 5-{4-(1-imidazolylmethyl)phenyl)-2,4-pentadien-1-ol, 4,5-dihydro-2-(1-imidazolyl)methylthia naphten-6-yl-methanol, 4,5-dihydro-2-{α-(1-imidazolyl)benzyl}thianaphten-6-yl-methanol and 3-{4-(imidazo-[1,2-a]pyridin-6-yl-methyl)phenyl}-2-propen-1-ol.

In the above-mentioned processes. When "Z" in general formula (I-4) is a hydroxyl group, the reaction is carried out in the presence of acids (inorganic acid such as HCl or $H_2SO_4$, or Lewis acid such as $BF_3$) or condensing agents such as dicyclohexylcarbodiimide (DCC). The acids are used in an amount of 0.1 to 10 equivalents to carboxylic acids or derivatives thereof represented by general formula (I-4), and the condensing agents are used in an amount of one to two equivalents to the carboxylic acid or derivatives thereof represented by general formula (I-4). When "DCC" is used as a condensing agent, a base such as N,N-dimethylaminopyridine may be used in an amount of 0.1 to one equivalent to "DCC". The reaction is carried out in inactive solvents such as benzene, toluene, dichloromethane, chloroform, acetonitrile, dichloroethane or acetone. It is preferable that the above reaction be carried out at 0° C. to 120° C.

Starting compounds for preparing 1,4-dihydropyridine derivatives of the present invention can be synthesized as follows:

1. Synthesis of (E)-3-[4-(1-imidazolylmethyl)phenyl]-2-propen-1-ol:

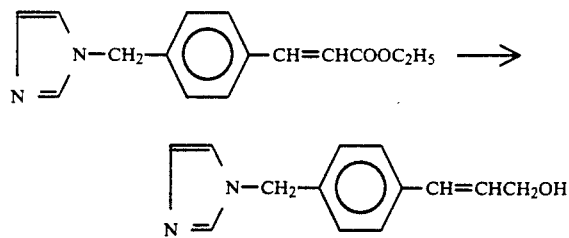

5.12 g (50 mM) of ethyl (E)-3-[4-(1-imidazolylmethyl)phenyl]acrylate was dissolved in 30 ml of tetrahydrofuran, and to this solution was added dropwise 93 ml of 1.5 M toluene solution of diisobutylaluminum hydride over one hour, while stirring under cooling with ice-cold water, and the reaction mixture was further stirred for one hour. Thereafter, to the mixture was added 1.5 ml of saturated brine, and after the mixture was stirred for two hours, the insoluble matter was filtered off and the filtrate was distilled under reduced pressure to remove the solvent, whereby the captioned compound was obtained. The yield was 7.75 g (72.3%).

NMR δCDCl₃ : 4.33 (d, 2H, J=5Hz), 5.10 (s, 2H), 6.37 (dt, 1H, J=16Hz, 5Hz), 6.61 (d, 1H, J=16Hz), 6.89 (s, 1H), 7.09-7.12 (d like, 3H), 7.35-7.38 (d like, 2H), 7.54 (s, 1H).

2. Synthesis of (E)-3-{4-(1-imidazolylmethyl)-phenyl}-2-propen-1-yl acetoacetate

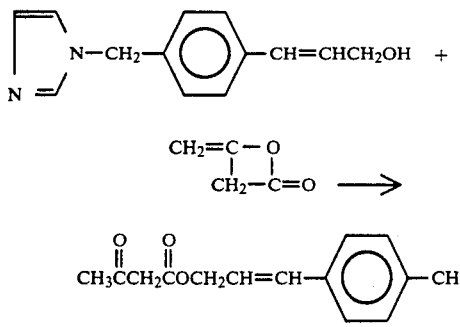

6.42 g (30 mM) of (E)-3-{4-(1-imidazolylmethyl)-phenyl}-2-propen-1-ol was dissolved in 30 ml of benzene, and to this solution was added 0.305 g (0.3 mM) of triethylamine. The mixture was heated at a temperature of 70° C. To this solution was added dropwise 3.03 g (36 mM) of diketene over 30 minutes and the mixture was stirred for one hour. The solvent was distilled off and the residue was chromatographed on a silica gel column, whereby the captioned compound was obtained. The yield was 8.95 g.

NMR δCDCl₃ : 2.28 (s, 3H), 3.51 (s, 2H), 4.80 (d, 2H, J=6Hz), 5.11 (s, 2H), 6.28 (dt, 1H, J=6Hz, 15Hz), 6.66 (d, 1H, J=15 HZ), 6.89 (s, 1H), 7.09 (s, 1H), 7.11 (d, 2H, J=7 HZ), 7.38 (d, 2H, J=7Hz), 7.54 (s, 1H).

3. Synthesis of (E)-3-{4-(1-imidazolylmethyl)-phenyl}-2-propen-1-yl 3-aminocrotonate

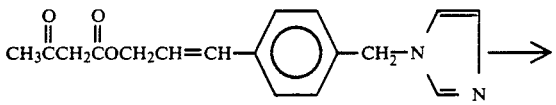

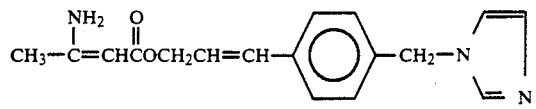

5.97 g (20 mM) of (E)-3-{4-(1-imidazolylmethyl)-phenyl}-2-propen-1-yl acetoacetate was dissolved in 50 ml of methanol, and to the solution was added 7.71 g (160 mM) of amMonium acetate at room temperatures, while stirring, and the mixture was stirred for six hours. To the solution were added 100 ml of dichloromethane and a saturated aqueous solution of sodium hydrogencarbonate to alkalize the solution. After the dichloromethane phase was separated from the aqueous solution, washed repeatedly with water, and then dried over anhydrous sodium sulfate, the solvent was distilled away, whereby to obtain 5.32 g of the captioned compound was obtained. The yield was 5.32 g (89.4%).

NMR δCDCl₃ : 1.92 (s, 3H), 4.58 (s, 1H), 4.73 (d, 2H, J=6Hz), 5.09 (s, 2H), 6.32 (dt, 1H, J=16, 6Hz), 6.62 (d, 1H, J=16Hz), 6.89 (s, 1H), 7.10 (d like 3H), 7.37 (d, 2H, J=8.4Hz), 7.54 (s, 1H).

Examples of 1,4-dihydropyridine derivatives of the present invention will be shown below:

EXAMPLE 1-1

(E)-3-[4-(1-imidazolylmethyl)phenyl]-2-propen-1-yl methyl 1,4-dihydro-2,6-dimethyl-4-(3-nitrophenyl)pyridine-3,5-dicarboxylate:

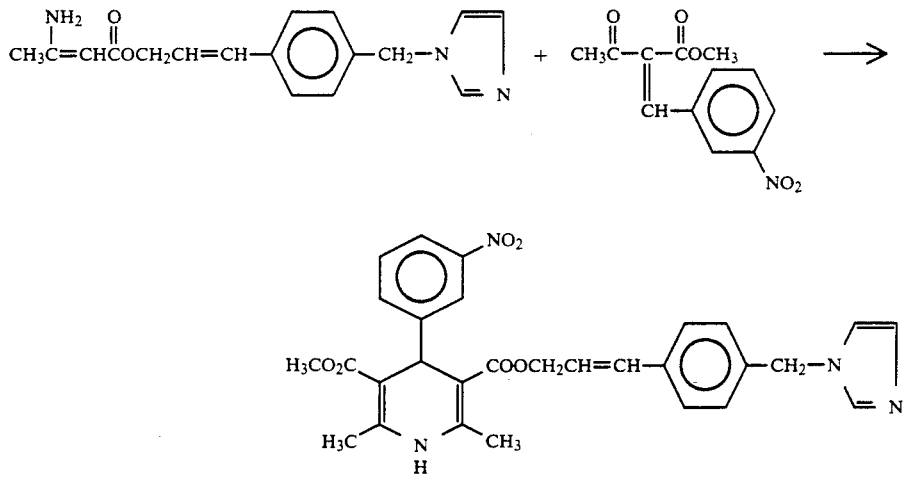

2.97 g (10 mM) of 3-[4-(1-imidazolylmethyl)phenyl]-2-propen-1-yl 3-aminocrotonate and 2.49 g (10 mM) of methyl 2-(3-nitrobenzylidene)acetoacetate were dissolved in 50 ml of toluene and then the solution was refluxed for eight hours. After cooling, the crystals were filtered off and then recrystallized from methanol whereby the captioned compound was obtained. The yield was 4.01 g (76%).

Melting point (°C) 176-178.4 (dec.).

NMR δCDCl₃ : 2.37 (s, 3H), 2.39 (s, 3H), 3.63 (s, 3H), 4.6~4.8 (m, 2H), 5.12 (s, 2H), 6.23 (dt, 1H, J=16Hz), 6.40 (brs, 1H), 6.50 (d, 1H, J=16 Hz), 6.92 (s, 1H), 7.1-7.13 (m, 3H), 7.31-7.37 (m, 3H), 7.57 (s, 1H), 7.58 (d, 1H, J=8,2 Hz), 8.13 (t, 1H, J=2 Hz).

| IR (cm⁻¹) | νCO | 1696 |

-continued

| | vNO$_2$ | 1530 1352 |
|---|---|---|

| Elemental analysis C$_{29}$H$_{28}$N$_4$O$_6$ | | | |
|---|---|---|---|
| | C (%) | H (%) | N (%) |
| Found | 65.78 | 5.29 | 10.76 |
| Calcd. | 65.90 | 5.34 | 10.60 |

EXAMPLE 1-2

Synthesis of (E)-3-[4-(1-imidazolylmethyl)-phenyl]-2-propen-1-yl methyl 1,4-dihidro-2,6-dimethyl-4-(3-nitrophenyl)pyridine-3,5-dicarboxylate:

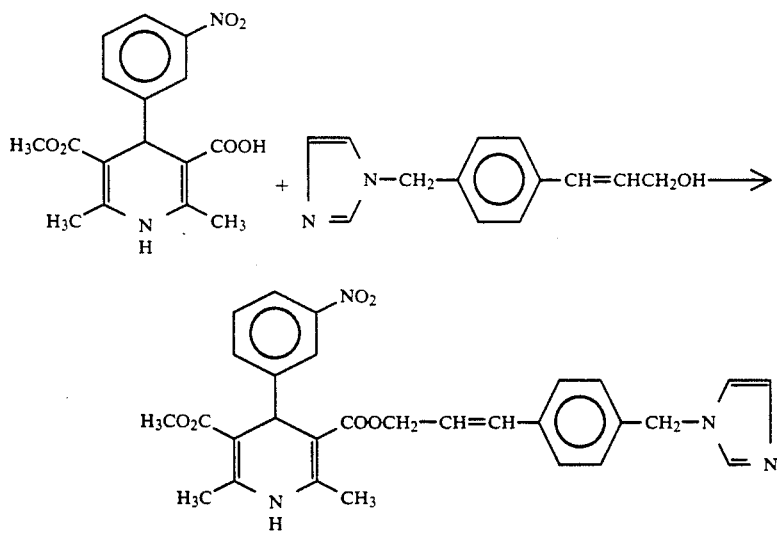

1.66 g (5 mM) of 1,4-dihydro-2,6-dimethyl-5-methoxycarbonyl-4-(3-nitrophenyl)pyridine-3-carboxylic acid together with 1.09 g (5 mM) of 3-[4-(1-imidazolylmethyl)phenyl]-2-propen-1-ol, 1.03 g (5 mM) of dicyclohexylcarbodiimide and 0.61 g (5 mM) of 4-N,N-dimethylaminopyridine were dissolved in 20 ml of toluene, while heating, and refluxed for eight hours. The hot solution was cooled to room temperature and the crystals produced were filtered off. The filtrate was washed with water and dried over anhydrous sodium sulfate.

After the solvent was distilled off, the residue was purified by chromatography on a silica gel column, whereby the captioned compound was obtained. The yield was 2.58 g (97.6%).

This compound is identical as the compound of Example 1-1 in melting point, NMR and IR values.

EXAMPLE 2

Methyl (E)-3-[4-(3-pyridylmethyl)phenyl]-2-propen-1-yl 1,4-dihydro-2,6-dimethyl-4-(3-nitrophenyl)pyridine-3,5-dicarboxylate:

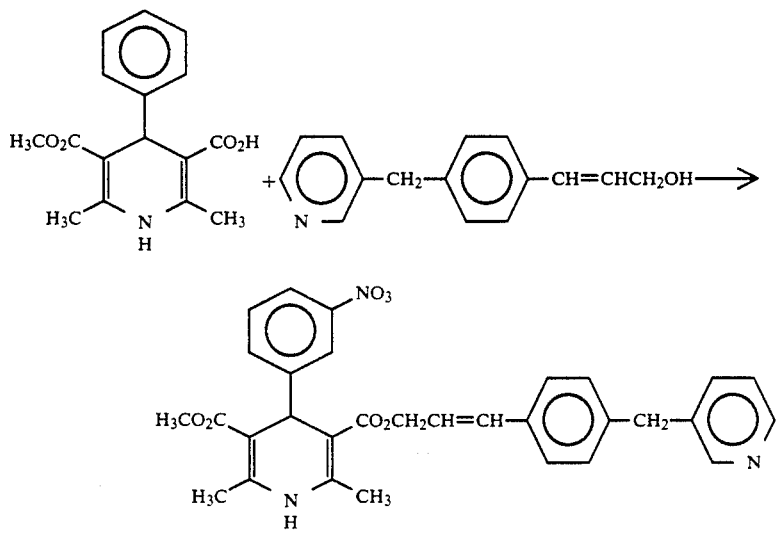

332 mg (1 mM) of 1,4-dihydro-2,6-dimethyl-5-methoxycarbonyl-4-(3-nitrophenyl)pyridine-3-carboxylic acid together with 225 mg (1 mM) of (E)-3-{4-(3-pyridylmethyl)phenyl]-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate.

After the solvent was distilled off, the residue was purified by chromatography on a silica gel column, whereby the captioned compound was obtained. The yield was 481 mg (89%).

Melting point (°C) 140.9–142.2.

NMR δCDCl₃: 2.37 (s, 3H), 2.38 (s, 3H), 3.63 (s, 3H), 3.97 (s, 2H, 4.67 (ddd, 1H, J=13Hz, 6Hz, 1 Hz), 4.74 (ddd, 1H, J=13Hz, 6Hz, 1 Hz), 5.13 (s, 1H, 5.76 (bs, 1H, 6.20 (dt, 1H, J=16 Hz, 6 Hz), 6.51 (d, 1H, J=16 Hz), 7.14 (d, 2H, J=8 Hz), 7.21 (dd, 1H, J=8 Hz, 5 Hz), 7.29 (d, 2H, J=8 Hz), 7.34 (t, 1H, J=8 Hz), 7.46 (d, 1H, J=8 Hz), 7.63 (d, 1H, J=8 Hz), 7.98 (ddd, 1H, J=8 Hz, 3 Hz, 2 Hz), 8.12 (t, 1H, J=2 Hz), 8.47 (dd, 1H, J=5 Hz, 2 Hz), 8.50 (d, 1H, J=2 Hz).

| IR (cm⁻¹) | νCO | 1700 |
| --- | --- | --- |
| | νNO₂ | 1525, 1350 |
| Mass Spectrometric Analysis | Molecular formula C₃₁H₂₉N₃O₆ | |
| | Found | 539.20623 |
| | Calcd. | 539.20560 |

EXAMPLE 3

(E)-3-[4-(1-imidazolyl)phenyl]-2-propen-1-yl methyl 1,4-dihydro-2,6-dimethyl-4-(3-nitrophenyl)pyridine-3,5dicarboxylate:

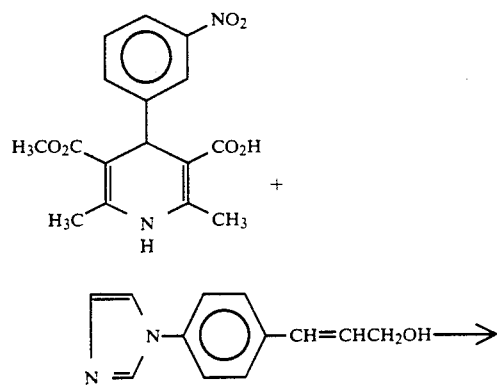

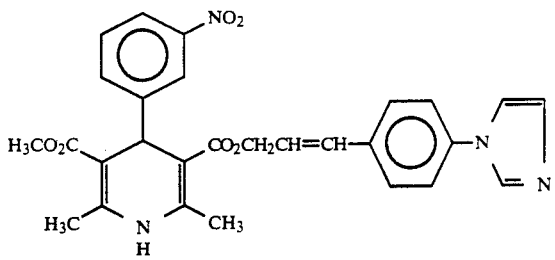

332 mg (1 mM) of 1,4-dihydro-2,6-dimethyl-5-methoxycarbonyl-4-(3-nitrophenyl)pyridine-3-carboxylic acid together with 200 mg (1 mM) of (E)-3-{4-(1-imidazolyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced was filtered off. The filtrate was washed with water and dried over anhydrous sodium sulfate. After the solvent was distilled off, the residue was purified by chromatography on a silica gel column, whereby the captioned compound was obtained. The yield was 494 mg (96%).

Melting point (° C.) 220.2–221.7.

NMR δCDCl₃: 2.38 (s, 3H), 2.41 (s, 3H), 3.65 (s, 3H), 4.69 (dd, 1H, J=13Hz, 6Hz), 4.78 (dd, 1H, J=13Hz, 6Hz), 5.15 (s, 1H), 5.81 (s, 1H), 6.27 (dt, 1H, J=16Hz, 6Hz), 6.54 (d, 1H, J=16Hz), 7.22 (s, 1H), 7.30 (s, 1H), 7.36 ) d, 2H, J=8Hz), 7.37 (t, 1H, J=8Hz), 7.45 (d, 2H, J=8Hz), 7.65 (d, 1H, J=8Hz), 7.88 (s, 1H), 7.99 (dt, 1H, J=8Hz, 8Hz), 8.15 (t, 1H, J=2Hz).

| IR (cm⁻¹) | νCO | 1705 |
| --- | --- | --- |
| | νNO₂ | 1530, 1350 |
| Mass Spectrometric Analysis | Molecular formula C₂₈H₂₆N₄O₆ | |
| | Found | 514.18454 |
| | Calcd. | 514.18520 |

EXAMPLE 4

(E)-3-[5-(1-imidazolylmethyl)-2-furan]-2-propen-1-yl methyl 1,4-dihydro-2,6-dimethyl-4-(3-nitrophenyl)pyridine-3,5-dicarboxylate:

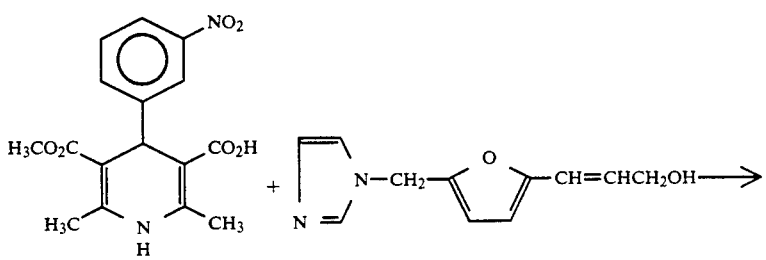

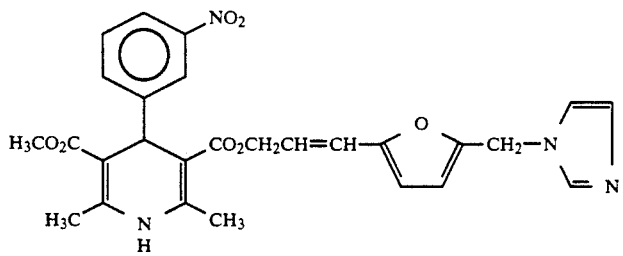

332 mg (1 mM) of 1,4-dihydro-2,6-dimethyl-5-methoxycarbonyl-4-(3-nitrophenyl)pyridine-3-carboxylic acid together with 204 mg (1 mM) of (E)-3-{5-(1-imidazolylmethyl)-2-furan}-2-propen-1-ol, 248 mg (1.2 mM) of dicyclohexylcarbodiimide and 134 mg (1.1 mM)

of 4-N,N-dimethylaminopyridine were dissolved in 5 ml of toluene, while heating, and refluxed for six hours. The solution was cooled to room temperature,, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 430 mg (83%)

Melting point (° C.) 169.1–170.0.

NMR δCDCl$_3$: 2.37 (s, 3H), 2.38 (s, 3H), 3.64 (s, 3H), 4.59 (dd, 1H, J=13Hz, 6Hz), 4.74 (dd, 1H, J=13Hz, 6Hz), 5.09 (s, 2H), 5.12 (s, 1H, 6.09 (dt, 1H, J=16Hz, 6Hz), 6.16 (1H, J=3Hz), 6.20 (d, 1H, J=16Hz), 6.24 (bs, 1H), 6.27 (d, 1H, J=3Hz), 6.99 (s, 1H), 7.08 (s, 1H), 7.34 (t, 1H, J=8Hz), 7.58 (s, 1H), 7.64 (d, 1H, J=8Hz), 7.97 (dd, 1H, J=8Hz, 2Hz), 8.13 (t, 1H, J=2Hz).

| IR (cm$^{-1}$) | νCO | 1695 |
| | νNO$_2$ | 1525, 1345 |
| Mass Spectrometric Analysis | Molecular formula C$_{27}$H$_{26}$N$_4$O$_7$ | |
| | Found | 518.18130 |
| | Calcd. | 518.18011 |

EXAMPLE 5

(E)-3-[5-(1-imidazolylmethyl)-2-thiophene]-2-propen-1yl methyl 1,4-dihydro-2,6-dimethyl-4-(3-nitrophenyl) pyridine-3,5-dicarboxylate:

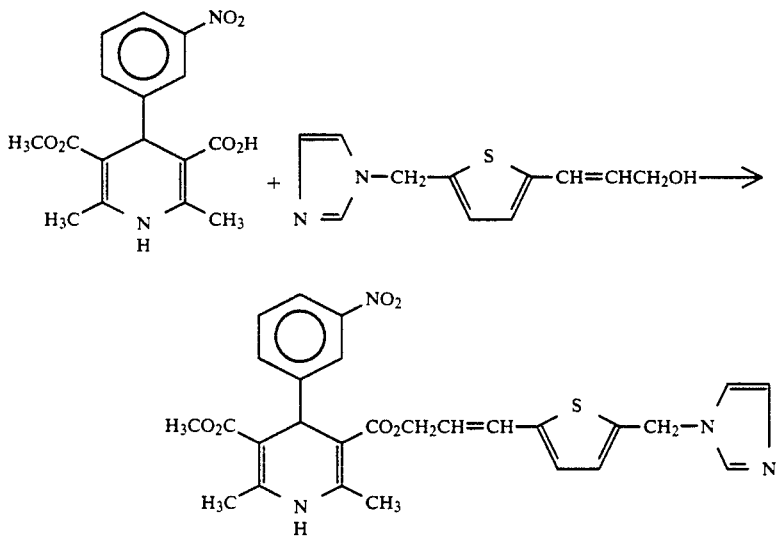

332 mg (1 mM) of 1,4-dihydro-2,6-dimethyl-5-methoxycarbonyl-4-(3-nitrophenyl)pyridine-3-carboxylic acid together with 220 mg (1 mM) of (E)-3-{5-(1-imidazolylmethyl)-2-thiophene}-2-propen-1-ol, 248 mg (1.2 mM) of dicyclohexyl-carbodiimide and 134 mg (1.1 mM) of 4-N,N-dimethylamino-pyridine were dissolved in 5 ml of toluene, while heating, and refluxed for six hours. The solution was cooled to room temperture, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 514 mg (96.1%)

Melting point (° C.) 169.5–172.3.

NMR δCDCl$_3$: 2.37 (s, 3H), 2.38 (s, 3H), 3.64 (s, 3H), 4.58 (ddd, 1H, J=13Hz, 6Hz, 1Hz), 4.71 (ddd, 1H, J=13Hz, 6Hz.1Hz), 5.11 (s, 1H), 5.22 (s, 1H), 5.95 (dt, 1H, J=16Hz, 6Hz), 6.08 (bs, 1H), 6.53 (d, 1H, J=4Hz), 6.83 (d, 1H, J=4Hz), 6.97 (s, 1H), 7.09 (s, 1H), 7.35 (t, 1H, J=8 Hz), 7.57 (s, 1H), 7.63 (d, 1H, J=8Hz), 7.97 (dt, 1H, J=8Hz, 2Hz), 8.11 (t, 1H, J=2Hz).

| IR (cm$^{-1}$) | νCO | 1695 |
| | νNO$_2$ | 1525, 1350 |
| Mass Spectrometric Analysis | Molecular formula C$_{27}$H$_{26}$N$_4$O$_6$S | |

| | |
|---|---|
| Found | 534.15771 |
| Calcd. | 534.15727 |

EXAMPLE 6

(E)-3-[4-(1-imidazolylmethyl)phenyl]-2-buten-1yl methyl 1,4-dihydro-2,6-dimethyl-4-(3-nitrophenyl)pyridine-3,5-dicarboxylate:

whereby the captioned compound was obtained. The yield was 539 mg (100%).

Melting point (° C.) 201.9–202.9.

NMR δCDCl₃: 2.03 (s, 3H), 2.37 (s, 3H), 2.39 (s, 3H), 3.64 (s, 3H), 4.71 (dd, 1H, J=13Hz, 6Hz), 4.78 (dd, 1H, J=13Hz, 6Hz), 5.11 (s, 1H), 5.12 (s, 2H), 5.77 (s, 1H), 5.82 (t, 1H, J=6Hz), 6.92 (s, 1H), 7.11 (s, 1H), 7.12 (d, 2H, J=8Hz), 7.34 (t, 1H, J=8Hz), 7.34 (d, 2H, J=8Hz), 7.56 (s, 1H), 7.63 (d, 1H, J=8Hz), 7.98 (dt, 1, J=8Hz, 2Hz), 8.12 (t, 1H, J=8Hz).

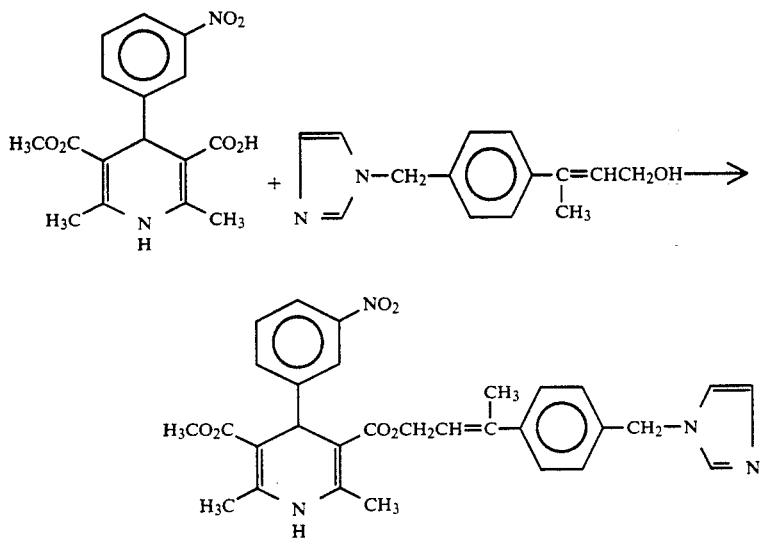

332 mg (1 mM) of 1,4-dihydro-2,6-dimethyl-5-methoxycarbonyl-4-(3-nitrophenyl)pyridine-3-carboxylic acid together with 228 mg (1 mM) of (E)-3-[4-(1-imidazolylmethyl)-phenyl]-2-buten-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled off, the residue was purified by chromatography on a silica gel column,

| IR (cm⁻¹) | νCO | 1700 |
|---|---|---|
| | νNO₂ | 1530, 1350 |
| Mass Spectrometric Analysis | Molecular formula C₃₀H₃₀N₄O₆ | |
| | Found | 542.21719 |
| | Calcd. | 542.21650 |

EXAMPLE 7

Ethyl (E)-3-[4-(1-imidazolylmethyl)phenyl]-2-propen-1-yl 1,4-dihydro-2,6-dimethyl-4-(3-nitrophenyl)-pyridine-3,5-dicarboxylate:

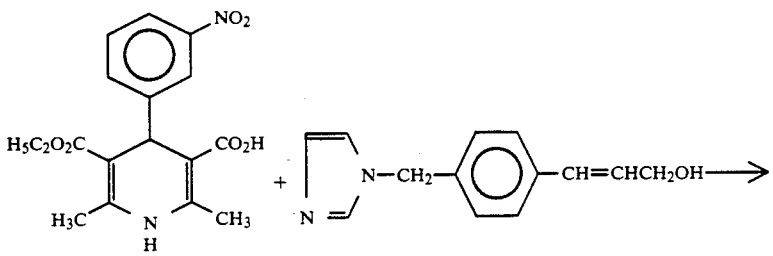

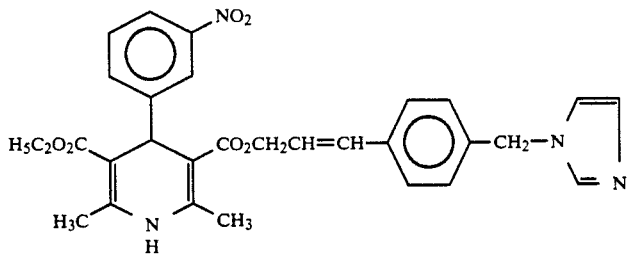

346 mg (1 mM) of 1,4-dihydro-2,6-dimethyl-5-ethoxycarbonyl-4-(3-nitrophenyl)pyridine-3-caboxylic acid together with 215 mg (1 mM) of (E)-3-{4-(1-imidazolylmethyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 474 mg (87.4%).

Melting point (° C.) 171.8–172.5.

NMR $\delta CDCl_3$ : 1.21 (t, 3H, J=6Hz), 2.40 (s, 3H), 2.39 (s, 3H), 4.01-4.17 (m, 2H), 4.65 (ddd, 1H, J=13Hz, 6Hz, 1Hz), 4.75 (ddd, 1H, J=13Hz, 6Hz, 1Hz), 5.11 (s, 2H), 5.13 (s, 1H), 5.74 (s, 1H), 6.21 (dt, 1H, J=16Hz, 6Hz), 6.49 (d, 1H, J=16Hz), 6.91 (s, 1H), 7.10 (s, 1H), 7.11 (d, 2H, J=8Hz), 7.31 (d, 2H, J=8Hz), 7.35 (t, 1H, J=8Hz), 7.55 (s, 1H), 7.64 (d, 1H, J=8Hz), 7.98 (dd, 1H, J=8Hz, 2Hz), 8.14 (t, 1H, J=2Hz).

| IR (cm$^{-1}$) | $\nu$CO | 1695 |
| --- | --- | --- |
| | $\nu NO_2$ | 1525, 1350 |
| Mass Spectrometric Analysis | Molecular formula $C_{30}H_{30}N_4O_6$ | |
| | Found | 542.21698 |
| | Calcd. | 542.21650 |

EXAMPLE 8

(E)-3-[4-(1-imidazolylmethyl)phenyl]-2-methyl-2-propen-1-yl methyl 1,4-dihydro-2,6-dimethyl-4-(3-nitrophenyl)-pyridine-3,5-dicarboxylate:

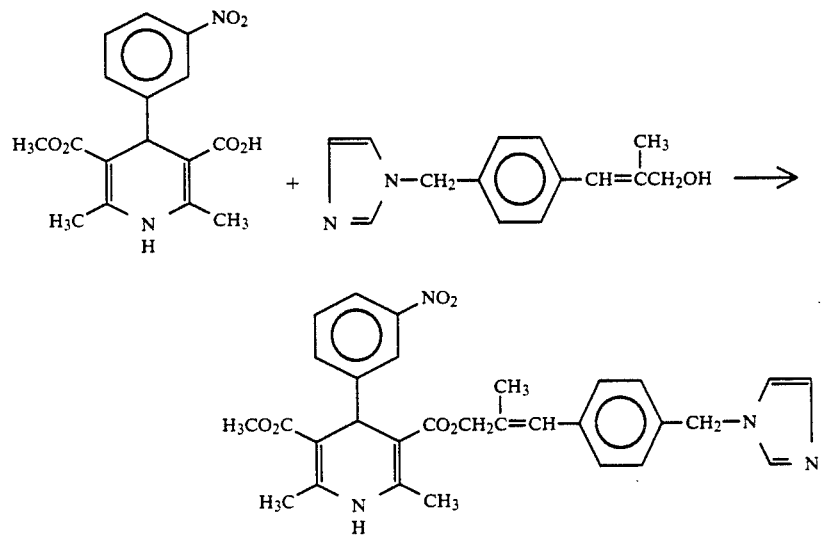

332 mg (1 mM) of 1,4-dihydro-2,6-dimethyl-5-methoxycabonyl-4-(3-nitrophenyl)pyridine-3-carboxylic acid together with 228 mg (1 mM) of (E)-3-{4-(1-imidazolylmethyl)-phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled in room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 523 mg (96.3%).

Melting point (° C.) 166.1–167.1.

NMR $\delta CDCl_3$: 1.75 (s, 3H), 2.36 (s, 3H), 2.41 (s, 3H), 3.65 (s, 3H), 4.55 (d, 1H, J=13Hz), 4.66 (d, 1H, J=13Hz), 5.11 (s, 2H), 5.15 (s, 1H), 5.98 (s, 1H), 6.33 (s, 1H), 6.92 (s, 1H), 7.10 (s, 1H), 7.12 (d, 2H, J=8Hz), 7.19 (d, 2H, J=8Hz), 7.35 (t, 1H, J=8Hz), 7.56 (s, 1H), 7.65 (d, 1H, J=8Hz), 7.98 (dd, 1H, J=8Hz, 2Hz), 8.12 (t, 1H, J=2Hz).

| IR (cm$^{-1}$) | $\nu$CO | 1695 |
| --- | --- | --- |
| | $\nu NO_2$ | 1530, 1350 |
| Mass Spectrometric Analysis | Molecular formula $C_{30}H_{30}N_4O_6$ | |

| | |
|---|---|
| Found | 542.21735 |
| Calcd. | 542.21650 |

EXAMPLE 9

Methyl (E)-3-[4-(1,3,4-triazol-1-ylmethyl)phenyl]-2-propen-1-yl 1,4-dihydro-2,6-dimethyl-4-(3-nitrophenyl)pyridine-3,5-dicarboxylate:

whereby the captioned compound was obtained. The yield was 522 mg (98.6%).

Melting point (° C.) 226.2–227.8.

NMR 67 CDCl$_3$ 2.37 (s, 3H), 2.39 (s, 3H), 3.64 (s, 3H), 4.66 (dd, 1H, J=13Hz, 6Hz), 4.77 (dd, 1H, J=13Hz, 6HZ), 5.13 (s, 1H), 5.17 (s, 2H), 5.86 (s, 1H), 6.24 (dt, 1H, J=16Hz), 6Hz), 6.49 (d, 1H, J=16Hz), 7.15 (d, 2H, J=8Hz), 7.35 (t, 1H, J=8Hz,), 7.97 (dd, 1H, J=8Hz, 2Hz), 8.13 (t, 1H, J=2H), 8.19 (s, 2H).

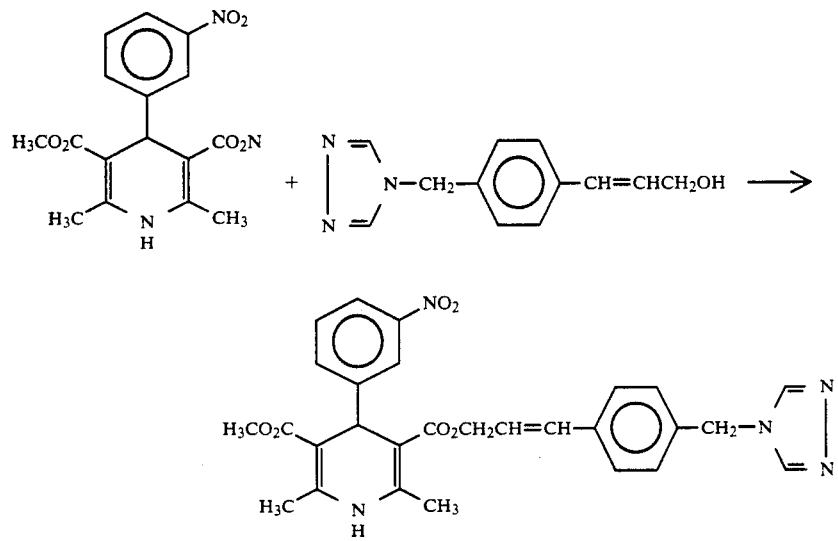

332 mg (1 mM) of 1,4-dihydro-2,6-dimethyl-5-methoxycarbonyl-4-(3-nitrophenyl)pyridine-3-caboxylic acid together with 215 mg (1 mM) of (E)-3-{4-(1,3,4-triazol-1-yl methyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column,

| IR (cm$^{-1}$) | $\nu$CO | 1695 |
|---|---|---|
| | $\nu$NO$_2$ | 1530, 1350 |
| Mass Spectrometric Analysis | Molecular formula C$_{28}$H$_{27}$N$_5$O$_6$ | |
| | Found | 529.19689 |
| | Calcd. | 529.19610 |

EXAMPLE 10

Methyl (E)-3-[4-(1,2,4-triazol-1-ylmethyl)-phenyl]-2-propen-1-yl 1,4-dihydro-2,6-dimethyl-4-(3-nitrophenyl)pyridine-3,5-dicarboxylate:

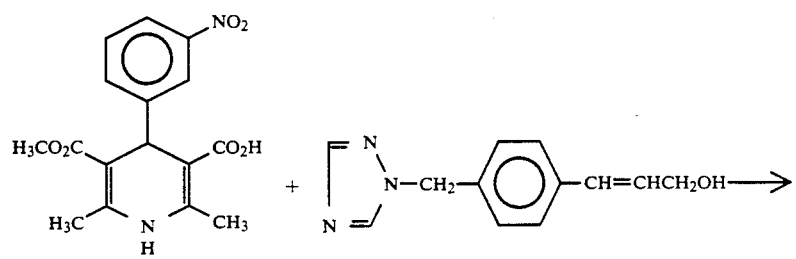

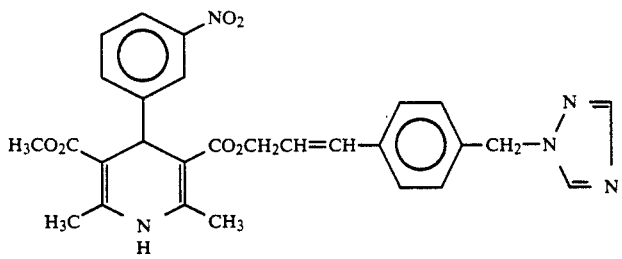

332 mg (1 mM) of 1,4-dihydro-2,6-dimethyl-5-methoxycarbonyl-4-(3-nitrophenyl)pyridine-3-carboxylic acid together with 215 mg (1 mM) of (E)-3-{4-(1,2,4-triazol-1-yl-methyl)phenyl}-2-propen-1-ol, 248 mg (1.2 mM) of dicyclohexylcarbodiimide and 134 mg (1.1 MM) of 4-N,N-dimethylaminopyridine were dissolved in 5 ml of toluene, while heating, and refluxed for six hours. The solution was cooled to room temperatures, and the crystals produced were filtered off. The filtrate was washed with water and dried over anhydrous sodium sulfate. After the solvent was distilled away, the residue was purified by chromatography on a silica gel column, the captioned compound was obtained. The yield was 522 mg (98.6%).

Melting point (° C.) 140.6–142.3.

NMR δCDCl₃: 2.37 (s, 3H), 2.39 (s, 3H), 3.64 (s, 3H), 4.66 (dd, 1H, J=13Hz, 6Hz), 4.75 (dd, 1H, J=13H, 6Hz), 5.13 (s, 1H), 5.34 (s, 2H), 5.73 (s, 1H), 6.23 (dt, 1H, J=16H, 6H), 6.51 (d, 1H, J=16Hz), 7.23 (d, 2H, J=8Hz), 7.34 (d, 2H, J=8Hz), 7.34 (t, 1H, J=7Hz), 7.63 (d, 1H, J=7HZ), 7.98 (dd, 1H, J=7Hz, 2Hz), 7.99 (s, 1H), 8.07 (s, 1H), 8.12 (t, 1H, J=2Hz).

| IR (cm⁻¹) | νCO | 1695 |
|---|---|---|
|  | νNO₂ | 1530, 1350 |
| Mass Spectrometric Analysis | Molecular formula C₂₈H₂₇N₅O₆ | |
|  | Found | 529.19641 |
|  | Calcd. | 529.19610 |

EXAMPLE 11

Methyl (E)-3-[4-(1,2,3,4-tetrazol-1-ylmethyl)phenyl]-2-propen-1yl 1,4-dihydro-2,6-dimethyl-4-(3-nitrophenyl)pyridine-3,5-dicarboxylate:

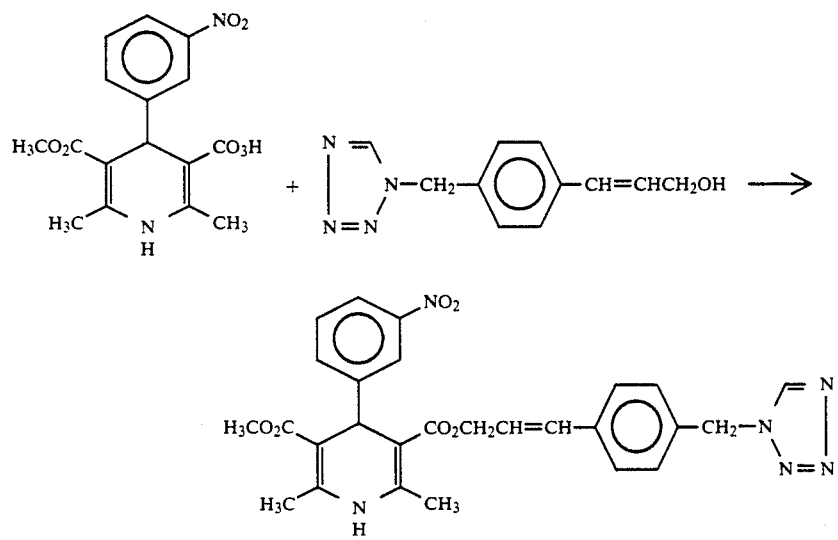

332 mg (1 mM) of 1,4-dihydro-2,6-dimethyl-5-methoxycarbonyl-4-(3-nitrophenyl)pyridine-3-carboxylic acid together with 217 mg (1 mM) of (E)-3-{4-(1,2,3,4-tetrazol-1-ylmethyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 442 mg (83.4%).

Melting point (° C.) 108.2–109.9.

NMR δCDCl₃: 2.37 (s, 3H), 2.39 (s, 3H), 3.64 (s, 3H), 4.65 (dd, 1H, J=13Hz, 6Hz), 4.77 (dd, 1H, J=13Hz, 6Hz), 5.13 (s, 1H), 5.58 (s, 2H), 5.77 (s, 1H), 6.24 (dt, 1H, J=16Hz, 6Hz), 6.50 (d, 1H, J=16Hz), 7.26 (d, 2H, J=8Hz), 7.35 (t, 1H, J=8Hz), 7.37 (d, 2H, J=8Hz), 7.63 (d, 1H, J=8Hz), 7.97 (dd, 1H, J=8Hz, 2Hz), 8.12 (t, 1H, J=2Hz), 8.52 (s, 1H).

| IR (cm⁻¹) | νCO | 1700 |
|---|---|---|
|  | νNO₂ | 1530, 1355 | mass (m/e). 530 (M⁺), 499, 408, 331, 287.

EXAMPLE 12

(E)-3-[4-(1-imidazolylmethyl)phenyl]-2-propen-1-yl methyl 1,4-dihydro-2,6-dimethyl-4-(2,3-dichlorophenyl)pyridine-3,5-dicarboxylate:

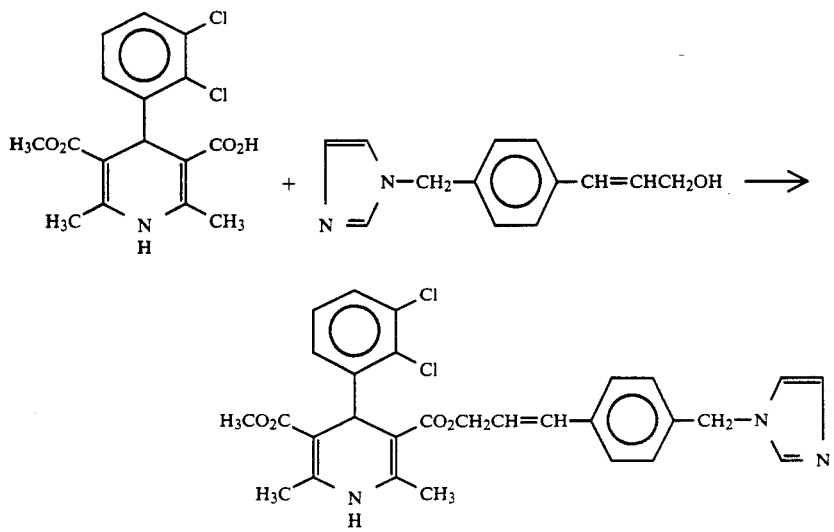

356 mg (1 mM) of 1,4-dihydro-2,6-dimethyl-5-methoxycarbonyl-4-(2,3-dichlorophenyl)pyridine-3-carboxylic acid together with 215 mg (1 mM) of (E)-3-[4-(1-imidazolylmethyl)phenyl]-2-propen-1-ol, 248 mg (1.2 mM) of dicyclohexyl-carbodiimide and 134 mg (1.1 mM) of 4-N,N-dimethylamino-pyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 481 mg (87%).

Melting point (° C.) 121.1–122.5.

NMR $\delta$CDCl$_3$: 2.32 (s, 3H), 2.34 (s, 3H), 3.60 (s, 3H), 4.63 (ddd, 1H, J=13Hz, 6Hz, 2Hz), 4.72 (ddd, 1H, J=13Hz, 6Hz, 2Hz), 5.10 (s, 2H, 5.49 (s, 1H), 5.70 (s, 1H), 6.18 (dt, 1H, J=16Hz, 6Hz), 6.41 (d, 1H, J=16Hz), 6.90 (s, 1H), 7.05 (t, 1H, J=8Hz), 7.09 (d, 2H, J=8Hz), 7.10 (s, 1H), 7.21 (dd, 1H, J=8Hz, 2Hz), 7.30 (d, 3H, J=8Hz), 7.55 (s, 1H).

IR (cm$^{-1}$). $\nu$CO 1695.

| Mass Spectrometric Analysis | Molecular formula $C_{29}H_{27}Cl_2N_3O_4$ |
|---|---|
| Found | 551.13765 |
| Calcd. | 551.13783 |

EXAMPLE 13

(Z)-3-{4-(1-imidazolylmethyl)phenyl}-2-fluoro-2-propen-1-yl methyl 1,4-dihydro-2,6-dimethyl-4-(3-nitrophenyl)pyridine-3,5-dicarboxylate:

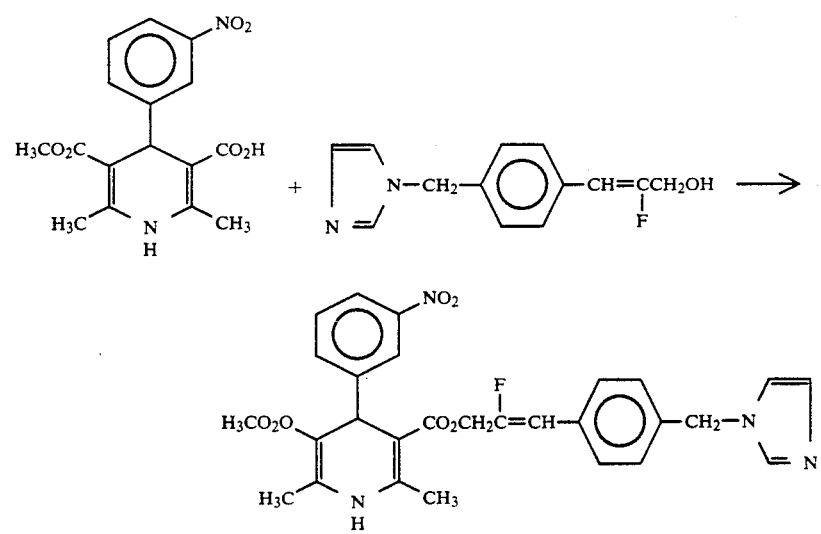

332 mg (1 mM) of 1,4-dihydro-2,6-dimethyl-5-methyoxycarbonyl-4-(3-nitrophenyl)pyridine-3-carboxylic acid together with 219 mg (1 mM) of (Z)-3-[4-(1-imidazolylmethyl)phenyl]-2-fluoro-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 506 mg (92.5%).

Melting point (° C.) 186.2–188.3.

NMR $\delta CDCl_3$: 2.38 (s, 3H), 2.39 (s, 3H), 3.63 (s, 3H), 4.63 (dd, 1H, J=13Hz, 18Hz), 4.75 (dd, 1H, J=13Hz, 18Hz), 5.12 (s, 3H), 5.71 (s, 1H, 37Hz), 5.86 (s, 1H), 6.91 (s, 1H), 7.10 (s, 1H), 7.13 (d, 2H, J=8Hz), 7.34 (t, 1H, J=8Hz), 7.45 (d, 2H, J=8Hz), 7.56 (s, 1H), 7.64 (d, 1H, J=8Hz), 7.97 (dd, 1H, J=8HZ, 2Hz), 8.11 (t, 1H, J=2Hz).

| IR (cm$^{-1}$) | $\nu$CO | 1700 |
| --- | --- | --- |
| | $\nu$NO$_2$ | 1530, 1350 |
| Mass Spectrometric Analysis | Molecular formula $C_{29}H_{27}FN_4O_6$ | |
| | Found | 546.19285 |
| | Calcd. | 546.19143 |

EXAMPLE 14

(E)-cinnamyl (E)-3-[4-(1-imidazolylmethyl)phenyl]-2-propen-1-yl 1,4-dihydro-2,6-dimethyl-4-(3-nitrophenyl) pyridine-3,5-dicarboxylate:

boxylic acid together with 215 mg (1 mM) of (E)-3-{4-(1-imidazolylmethyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 588 mg (93.2%).

Melting point (° C.) 96.8–98.5.

NMR $\delta CDCl_3$: 2.39 (s, 6H), 4.61 - 4.78 (m, 4H), 5.09 (s, 2H), 5.18 (s, 1H), 5.79 (s, 1H), 6.14–6.26 (m, 2H), 6.48 (d, 1H, J=16Hz), 6.53 (d, 1H, J=16Hz), 6.90 (s, 1H), 7.07 (d, 2H, J=8Hz), 7.11 (s, 1H), 7.24–7.34 (m, 8H), 7.56 (s, 1H), 7.65 (d, 1H, J=8Hz), 9.95 (dd, 1H, J=8Hz, 2Hz), 8.16 (t, 1H, J=2HZ).

| IR (cm$^{-1}$) | $\nu$CO | 1695 |
| --- | --- | --- |
| | $\nu$NO$_2$ | 1530, 1345 |
| Mass Spectrometric Analysis | Molecular formula $C_{37}H_{34}N_4O_6$ | |
| | Found | 630.24661 |
| | Calcd. | 630.24779 |

EXAMPLE 15

(E)-2,(E)-4-hexadien-1-yl (E)-3-[4-(1-imidazolylmethyl)phenyl] 2-propen-1-yl 1,4-dihydro-2,6-dimethyl-4-

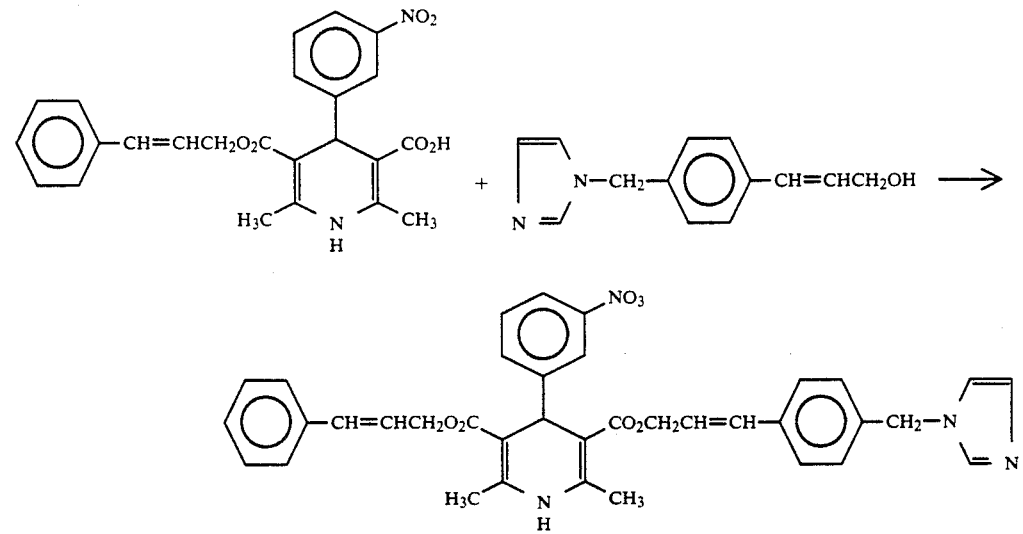

434 mg (1 mM) of 5-(E)-cinnamyloxycarbonyl-1,4-dihydro-2,6-dimethyl-4-(3-nitrophenyl)pyridine-3-carboxylic acid together with 215 mg (1 mM) of (E)-3-{4-(1-imidazolylmethyl)phenyl}-2-propen-1-ol, 248 mg (3-nitrophenyl)pyridine-3,5-dicarboxylate:

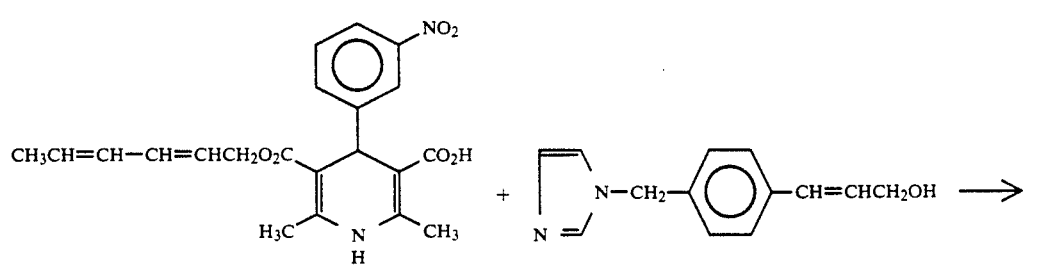

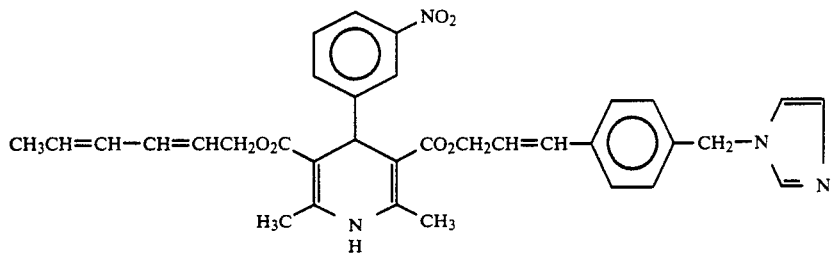

398 mg (1 mM) of 1,4-dihydro-2,6-dimethyl-5-{(E)-2,(E)-4-hexadien-1-yl}oxycarbonyl -4-(3-nitrophenyl)-pyridine-3-carboxylic acid together with 215 mg (1 mM) of (E)-3-{4-(1-imidazolylmethyl)phenyl}-2-propen-1-ol, 248 mg (1,2 mM) of dicyclohexylcarbodiimide

EXAMPLE 16

(E)-3-[4-(1-imidazolylmethyl)phenyl]-2-propen-1-yl 2-methoxyethyl 1,4-dihydro-2,6-dimethyl-4-(3-nitrophenyl)pyridine-3,5-dicarboxylate:

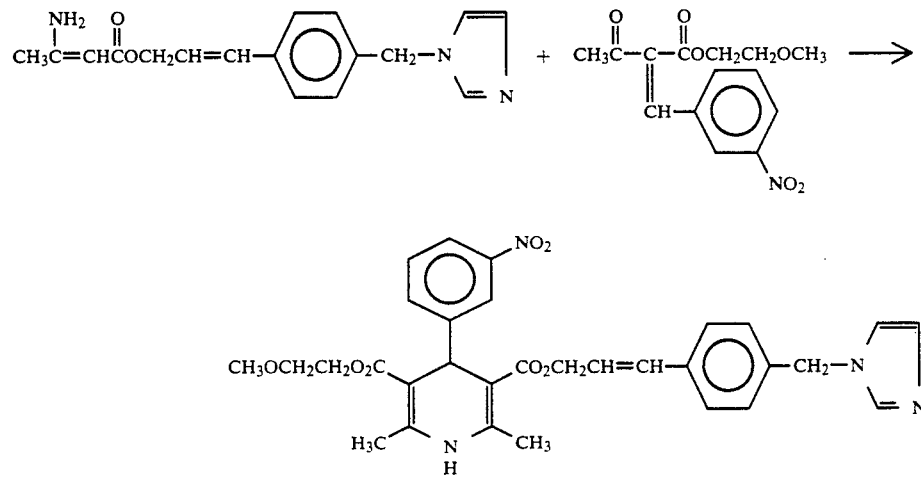

and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 544 mg (91.4%).

Melting point (° C.) 138.6–140.2.

NMR $\delta$CDCl$_3$ : 1.73 (d, 3H, J=7Hz), 2.37 (s, 3H), 2.39 (s, 3H), 4.50 (dd, 1H, J=13Hz, 7Hz), 4.58 (dd, 1H, J=13Hz, 7Hz), 4.65 (dd, 1H, J=13Hz, 6Hz), 4.75 (dd, 1H, J=13Hz, 6Hz), 5.11 (s, 2H), 5.14 (s, 1H), 5.55 (dt, 1H, J=15Hz, 7Hz), 5.67 (dq, 1H, J=15Hz, 7Hz), 5.82 (bs, 1H), 5.99 (dd, 1H, J=15Hz, 11Hz), 6.12 (dd, 1H, J=15Hz, 11Hz), 6.20 (dt, 1H, J=16Hz, 6Hz), 6.49 (d, 1H, J=16Hz), 6.90 (s, 1H), 7.10 (s, 1H), 7.11 (d, 2H, J=8Hz), 7.31 (d, 2H, J=8Hz), 7.34 (t, 1H, J=8Hz), 7.56 (s, 1H), 7.64 (d, 1H, J=8Hz), 7.97 (dd, 1H, J=8Hz, 2Hz), 8.13 (s, 1H).

297 mg (1 mM) of 3-[4-(1-imidazolylmethyl)phenyl]-2-propen-1-yl 3-aminocrotonate and 293 mg (1 mM) of 2-methoxyethyl 2-(3-nitrobenzylidene)acetoacetate were dissolved in 5 ml of toluene and refluxed for six hours. After cooling, the crystals produced were filtered off and recrystallized from methanol whereby the captioned compound was obtained. The yield was 502 mg (87.6%).

Melting point (° C.) 115.1–116.9.

NMR $\delta$CDCl$_3$ :2.37 (s, 3H), 2.39 (s, 3H), 3.29 (s, 3H), 3.46–3.58 (m, 2H), 4.09–4.24 (m, 2H), 4.64 (dd, 1H, J=13Hz, 6Hz), 4.73 (dd, 1H, J=13Hz, 6Hz), 5.11 (s, 2H), 5.15 (s, 1H), 5.85 (s, 1H), 6.21 (dt, 1H, J=15Hz, 6Hz), 6.49 (d, 1H, J=15Hz), 6.91 (s, 1H), 7.11 (d, 2H, J=8Hz), 7.32 (d, 2H, J=8HZ), 7.35 (t, 1H, J=8Hz), 7.55 (s, 1H), 7.67 (d, 1H, J=8Hz), 7.97 (dd, 1H, J=8Hz, 2Hz), 8.14 (t, 1H, J=2Hz).

| IR (cm$^{-1}$) | $\nu$CO | 1700 |
|---|---|---|
| | $\nu$NO$_2$ | 1530, 1350 |
| Mass Spectrometric Analysis | Molecular formula C$_{34}$H$_{34}$N$_4$O$_6$ | |
| | Found | 594.24765 |
| | Calcd. | 594.24779 |

| IR (cm$^{-1}$) | $\nu$CO | 1700 |
|---|---|---|
| | $\nu$NO$_2$ | 1530, 1350 |
| Mass Spectrometric Analysis | Molecular formula C$_{31}$H$_{32}$N$_4$O$_7$ | |
| | Found | 572.22791 |
| | Calcd. | 572.22706 |

EXAMPLE 17

(E)-3-[4-(1-imidazolylmethyl)phenyl]-2-propen-1-yl methyl 1,4-dihydro-2,6-dimethyl-4-(3-trifluoromethylphenyl)pyridine-3,5-dicarboxylate:

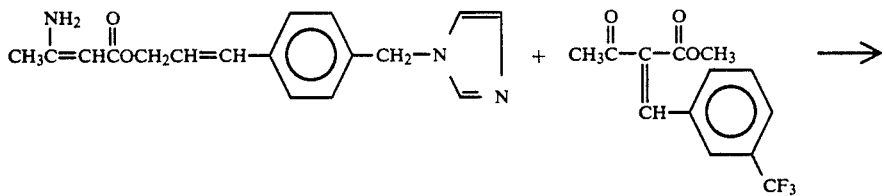

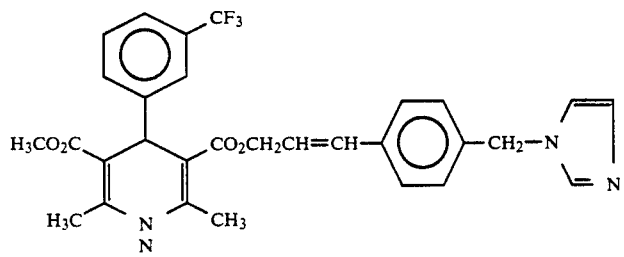

297 mg (1 mM) of 3-{4-(1-imidazolylmethyl)phenyl}-2-propen-1-yl 3-aminocrotonate and 272 mg (1mM) of methyl 2-(3-trifluoromethylbenzylidene)acetoacetate were dissolved in 5 ml of toluene and refluxed for six hours. After cooling, the crystals produced were filtered off and recrystallized from methanol, whereby the captioned compound was obtained. The yield was 394 mg (71.5%).

Melting point (20° C. 170.9–171.5.

NMR δCDCl$_3$: 2.36 (s, 3H), 2.38 (s, 3H), 3.63 (s, 3H), 4.65 (dd, 1H, J=13Hz, 6Hz), 4.74 (dd, 1H, J=13 Hz, 6Hz), 5.08 (s, 1H), 5.10 (s, 2H), 5.71 (s, 1H), 6.20 (dt, 1H, J=16Hz, 6Hz), 6.47 (d, 1H, J=16Hz), 6.90 (s, 1H), 7.09 (s, 1H), 7.10 (d, 2H, J=8Hz), 7.30 (t, 1H, J=8Hz), 7.31 (d, 2H, J=8Hz), 7.38 (d, 1H, J=8Hz), 7.46 (d, 1H, J=8Hz), 7.53 (s, 1H), 7.55 (s, 1H).

IR (cm$^{-1}$): νCO 1695.

| Mass Spectrometric Analysis | Molecular formula C$_{30}$H$_{28}$N$_3$O$_4$ | |
|---|---|---|
| | Found | 551.20243 |
| | Calcd. | 551.20315 |

EXAMPLE 18

(E)-3-[4-(1-imidazolylmethyl)phenyl]-2-propen-1-yl methyl 1,4-dihydro-2,6-dimethyl-4-(2-cyanophenyl)pyridine-3,5-dicarboxylate:

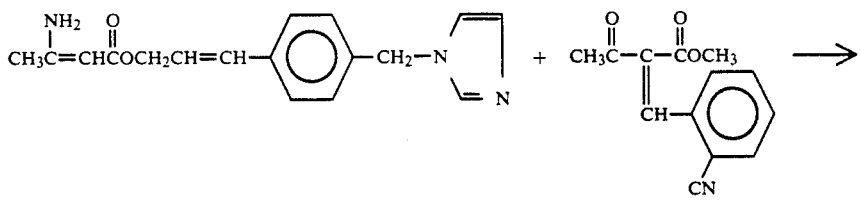

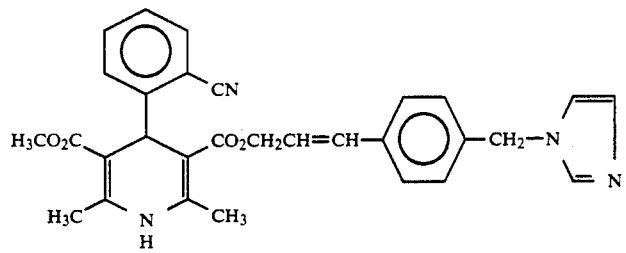

297 mg (1 mM) of 3-[4-(1-imidazolylmethyl)phenyl]-2-propen-1-yl 3-aminocrotonate and 229 mg (1 mM) of methyl 2-(2-cyanobenzylidene)acetoacetate were dissolved in 5 ml of toluene and refluxed for six hours. After cooling, the crystals produced were filtered off and recrystallized from methanol whereby the captioned compound was obtained. The yield was 402 mg (79.1%).

Melting point (° C.) 166.9–169.5.

NMR δCDCl$_3$: 2.35 (s, 3H), 2.37 (s, 3H), 3.64 (s, 3H), 4.67 (dd, 1H, J=13Hz, 6Hz), 4.73 (dd, 1H, J=13Hz, 6Hz), 5.10 (s, 2H), 5.35 (s, 1H), 5.77 (s, 1H), 6.26 (dt, 1H, J=16Hz, 6Hz), 6.38 (d, 1H, J=16Hz), 6.90 (s, 1H), 7.08 (d, 2H, J=8Hz), 7.10 (s, 1H), 7.17 (td, 1H, J=8Hz,

2Hz), 7.30 (d, 2H, J=8Hz), 7.41–7.50 (m, 3H), 7.54 (s, 1H).

| IR (cm$^{-1}$) | $\nu$CN | 2230 |
| | $\nu$CO$_2$ | 1700 |

| Mass Spectrometric Analysis | Molecular formula C$_{30}$H$_{28}$N$_4$O$_4$ | |
| --- | --- | --- |
| | Found | 508.21187 |
| | Calcd. | 508.21102 |

EXAMPLE 19

5-[4-(1-imidazolylmethyl)phenyl]-(E)-2,(E)-4-pentadien-1-yl methyl 1,4-dihydro-2,6-dimethyl-4-(3-nitrophenyl)pyridine-3,5-dicarboxylate:

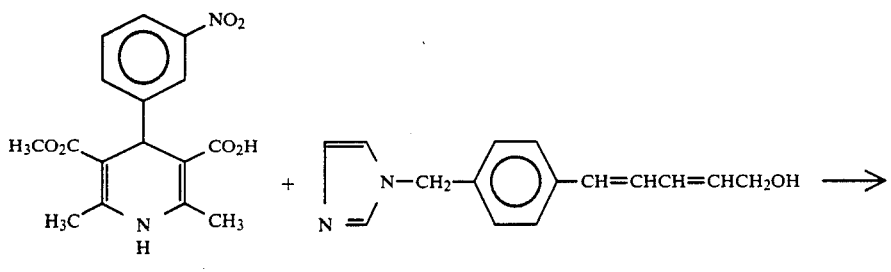

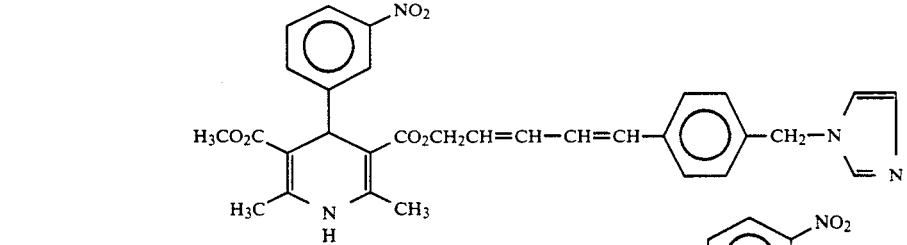

332 mg (1 mM) of 1,4-dihydro-2,6-dimethyl-5-methoxycarbonyl-4-(3-nitrophenyl)pyridine-3-carboxylic acid together with 240 mg (1 mM) of 5-[4-(1-imidazolylmethyl)phenyl]-(E)-2,(E)-4-pentadien-1-ol, 248 mg (1,2 mM) of dicyclohexyl-carbodiimide and 134 mg (1.1 mM) of 4-N,N-dimethylamino-pyridine were dissolved in 5 ml of toluene, while heating and refluxed for six hours. The solution was cooled to room temperatures, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 378 mg (68.4%).

Melting point (° C.) 179 (dec.).

NMR $\delta$CDCl$_3$: 2.377 (s, 3H), 2.388 (s, 3H), 3.644 (s, 3H), 4.580 (dd, 1H, J=14Hz, 7Hz), 4.700 (dd, 1H, J=14Hz, 7Hz), 5.129 (s, 1H), 5.155 (s, 2H), 5.825 (s, 1H), 5.850 (dt, 1H, J=15Hz, 7Hz), 6.280 (dd, 1H, J=15Hz, 13Hz), 6.470 (d, 1H, J=16Hz), 6.735 (dd, 1H, J=16Hz, 13Hz), 6.955 (s, 1H), 7.142 (d, 2H, J=8.4Hz), 7.167 (s, 1H), 7.377 (t, 1H, J=7.5Hz), 7.396 (d, 2H, J=8.4Hz), 7.635 (dt, 1H, J=7.5Hz, 2Hz), 7.820 (s, 1H), 8.000 (ddd, 1H, J=7.5Hz, 2Hz, 1Hz), 8.130 (dd, 1H, J=2Hz, 1Hz).

| IR (cm$^{-1}$) | $\nu$CO | 1700 |
| | $\nu$NO$_2$ | 1528, 1350 |

| Mass Spectrometric Analysis | Molecular formula C$_{31}$H$_{30}$N$_4$O$_6$ | |
| --- | --- | --- |
| | Found | 554.21709 |
| | Calcd. | 554.21650 |

EXAMPLE 20

(E)-3-[2-(1-imidazolylmethyl)phenyl]-2-propen-1-yl methyl 1,4-dihydro-2,6-dimethyl-4-(3-nitrophenyl)pyridine-3,5-dicarboxylate:

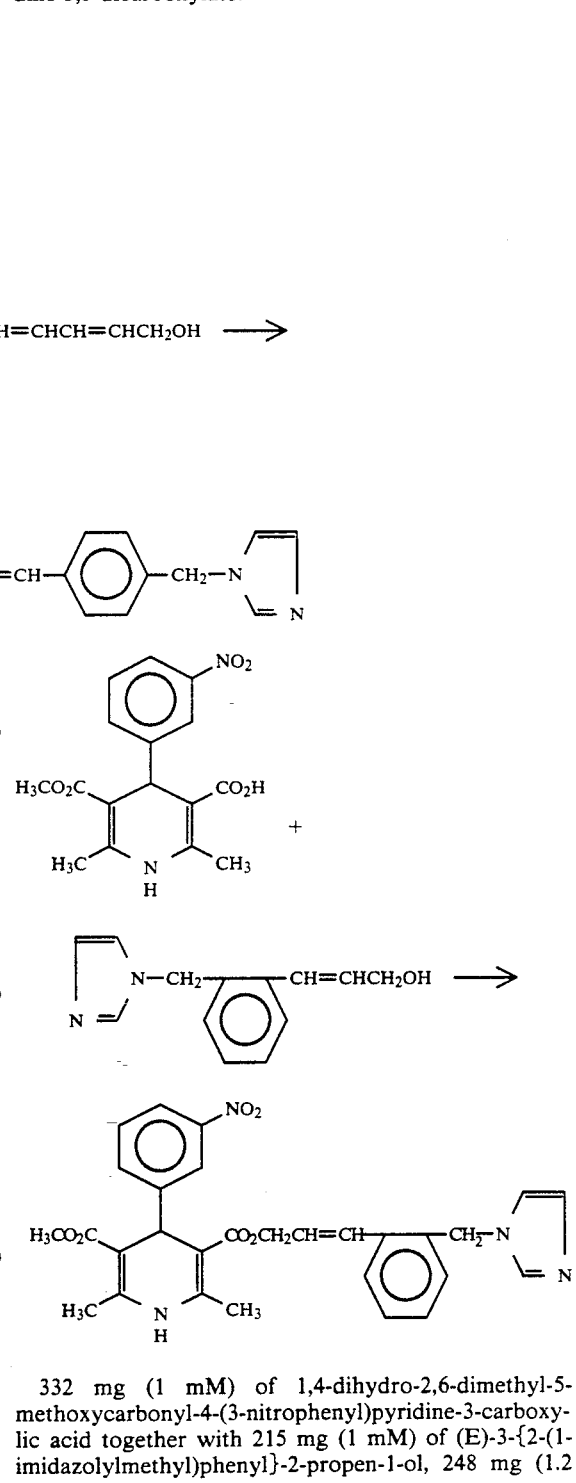

332 mg (1 mM) of 1,4-dihydro-2,6-dimethyl-5-methoxycarbonyl-4-(3-nitrophenyl)pyridine-3-carboxylic acid together with 215 mg (1 mM) of (E)-3-{2-(1-imidazolylmethyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 528 mg (100%).

Melting point (° C.) 182–182.5.

NMR δCDCl$_3$: 2.38 (s, 3H), 2.39 (s, 3H), 3.64 (s, 3H), 4.72 (d, 2H, J=6Hz), 5.16 (s, 2H), 5.16 (s, 1H), 6.07 (s, 1H), 6.13 (dt, 1H, J=16Hz, 6Hz), 6.66 (d, 1H, J=16Hz), 6.90 (s, 1H), 7.03 (dd, 1H, J=8Hz, 1Hz), 7.13 (s, 1H), 7.26–7.40 (m, 2H), 7.35 (t, 1H, J=7Hz), 7.45 (dd, 1H, J=8Hz, 1Hz), 7.64 (dt, 1H, J=7Hz, 2Hz), 7.65 (s, 1H), 7.96 (ddd, 1H, J=7Hz, 2Hz, 1Hz), 8.13 (dd, 1H, J=2Hz, 1Hz).

| IR (cm$^{-1}$) | νCO | 1702 |
|---|---|---|
| | νNO$_2$ | 1530, 1348 |
| Mass Spectrometric Analysis | Molecular formula C$_{29}$H$_{28}$N$_4$O$_6$ | |
| | Found | 528.20097 |
| | Calcd. | 528.20085 |

EXAMPLE 21

(E)-3-[3-(1-imidazolylmethyl)phenyl]-2-propen-1-yl methyl 1,4-dihydra-2,6-dimethyl-4-(3-nitrophenyl)pyridine-3,5-dicarboxylate:

methyl)phenyl]-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled off, the residue was purified by chromatography on a silica gel column, whereby the captioned compound was obtained. The yield was 528 mg (100%).

Melting point (° C.) 190–191.5.

NMR δCDCl$_3$: 2.38 (s, 3H), 2.40 (s, 3H), 3.64 (s, 3H), 4.63 (dd, 1H, J=13.2Hz, 7Hz), 4.79 (dd, 1H, J=13.2Hz, 7Hz), 5.13 (s, 1H), 5.19 (s, 1H), 5.84 (s, 1H), 6.22 (dt, 1H, J=16Hz, 7Hz), 6.45 (d, 1H, J=16Hz), 7.03 (s, 1H), 7.08 (dt, 1H, J=7Hz, 3Hz), 7.16 (s, 1H), 7.21 (s, 1H), 7.31 (dt, 1H, J=7Hz, 3Hz), 7.34 (t, 1H, J=7Hz), 7.35 (t, 1H, J=7.8Hz), 7.63 (dt, 1H, J=7.8Hz, 2Hz), 7.91 (s, 1H), 7.98 (ddd, 1H, J=7.8Hz, 2Hz, 1Hz), 8.15 (dd, 1H, J=2Hz, 1Hz).

| IR (cm$^{-1}$) | νCO | 1702 |
|---|---|---|
| | νNO$_2$ | 1532, 1352 |
| Mass Spectrometric Analysis | Molecular formula C$_{29}$H$_{28}$N$_4$O$_6$ | |
| | Found | 528.20191 |
| | Calcd. | 528.20085 |

EXAMPLE 22

(E)-3-[4-(1-imidazolylmethyl)phenyl]-2-propen-1-yl methyl 1,4-dihydro-2,6-dimethyl-4-(3-pyridyl)pyridine-3,5-dicarboxylate:

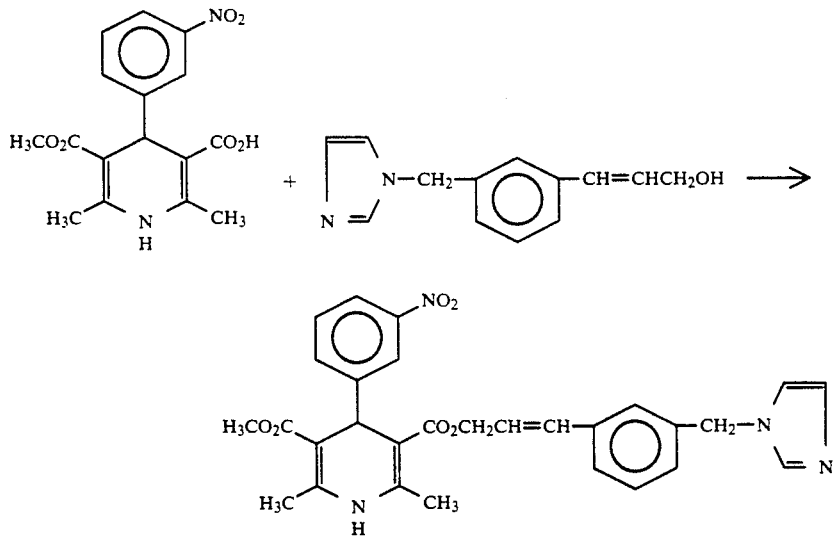

332 mg (1 mM) 1,4-dihydro-2,6-dimethyl-5-methoxycarbonyl-4-(3-nitrophenyl)pyridine-3-carboxylic acid together with 215 mg (1 mM) of (E)-3-{3-(1-imidazolyl-

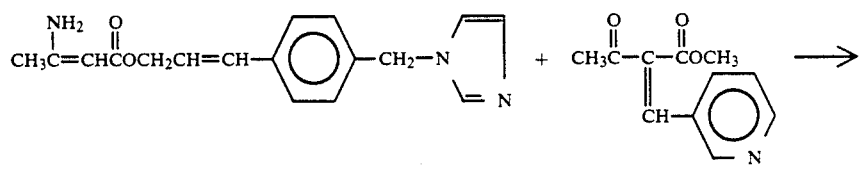

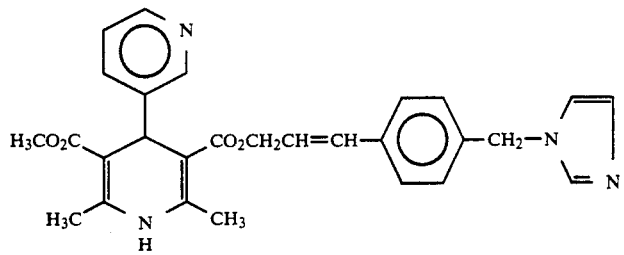

297 mg (1 mM) of 3-[4-(1-imidazolylmethyl)phenyl]-2-propen-1-yl 3-aminocrotonate and 205 mg (1 mM) of methyl 2-(3-pyridylidene)acetoacetate were dissolved in 5 ml of toluene and refluxed for six hours. After cooling, the crystals produced were filtered off and recrystallized from methanol, whereby the captioned compound was obtained. The yield was 378 mg (78%).

Melting point (° C.) 146 (dec.).

NMR δCDCl$_3$: 2.35 (.s, 3H), 2.37 (s, 3H), 3.64 (s, 3H), 4.68 (dd, 1H, J=15HZ, 6Hz), 4.74 (dd, 1H, J=15HZ, 6Hz), 5.03 (s, 1H), 5.12 (s, 2H), 6.22 (dt, 1H, J=16Hz, 6Hz), 6.31 (s, 1H), 6.48 (d, 1H, J=16Hz), 6.92 (s, 1H), 7.11 (s, 1H), 7.11 (d, 2H, J=8.7HZ), 7.16 (dd, 1H, J=7.5HZ, 4.5Hz), 7.33 (d, 2H, J=8.7Hz), 7.62 (s, 1H), 7.63 (dt, 1H, J=7.5HZ, 1.8HZ), 8.37 (dd, 1H, J=4.5Hz, 1.8Hz), 8.55 (d, 1H, J=1.8Hz).

IR (cm$^{-1}$). νCO 1694.

| Mass Spectrometric Analysis | Molecular formula | C$_{28}$H$_{28}$N$_4$O$_4$ |
|---|---|---|
| | Found | 484.21145 |
| | Calcd. | 484.21102 |

EXAMPLE 23

(E)-3-[4-(1-imdazolylmethyl)phenyl]-2-propen-1-yl methyl 1,4-dihydro-2,6-dimethyl-4-(4-quinolyl)pyridine-3,5-dicarboxylate:

297 mg (1 mM) of 3-[4-(1-imidazolylmethyl)phenyl]-2-propen-1-yl 3-aminocrotonate and 255 mg (1 mM) of 2-(4-quinolylidene)acetoacetate were dissolved in 5 ml of toluene and refluxed for 15 hours. After cooling, the crystals produced were filtered off and recrystallized from methanol, whereby the captioned compound was obtained. The yield was 371 mg (69%).

Melting point (° C.) 122.5 (dec.).

NMR δCDCl$_3$: 2.40 (s, 3H), 2.43 (s, 3H), 3.41 (s, 3H), 4.47 (dd, 1H, J=13.5Hz, 6Hz), 4.48 (dd, 1H, J=13.5Hz, 6Hz), 5.16 (s, 2H), 5.78 (dt, 1H, J=15.6Hz, 6Hz), 5.87 (s, 1H), 6.09 (s, 1H), 6.19 (d, 1H, J=15.6Hz), 6.97 (s, 1H), 7.11 (d, 2H, J=8.7Hz), 7.15 (d, 2H, J=8.7Hz), 7.17 (s, 1H), 7.51 (dt, 1H, J=7.8Hz, 1.8Hz), 7.52 (d, 1H, J=3.9Hz), 7.63 (dt, 1H, J=7.8Hz, 1.8Hz), 7.77 (s, 1H), 8.12 (dd, 1H, J=7.8Hz, 1Hz), 8.60 (dd, 1H, J=7.8Hz), 8.81 (d, 1H, J=3.9Hz).

IR(cm$^{-1}$): νCO 1700.

| Mass Spectrometric Analysis | Molecular formula | C$_{32}$H$_{30}$N$_4$O$_4$ |
|---|---|---|
| | Found | 534.22834 |
| | Calcd. | 534.22667 |

EXAMPLE 24

(E)-3-[4-{1-(1-imidazolyl)ethyl}phenyl]-2-propen-1-yl methyl 1,4-dihydro-2,6-dimethyl-4-(3-nitrophenyl)-pyridine-3,5-dicarboxylate:

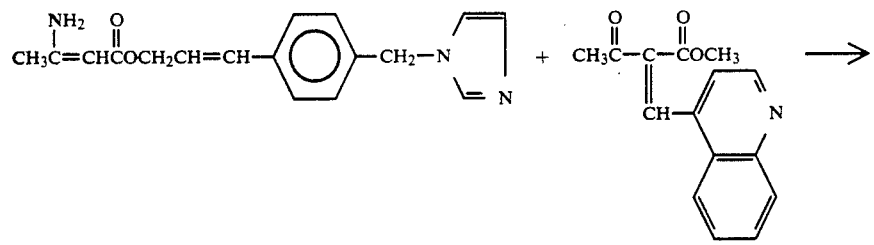

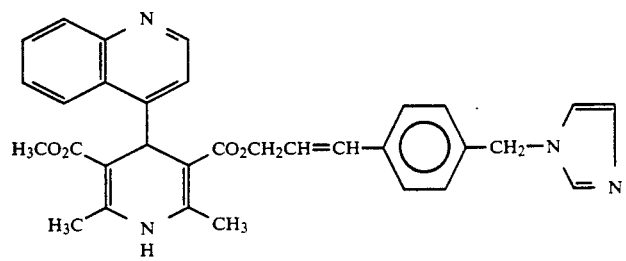

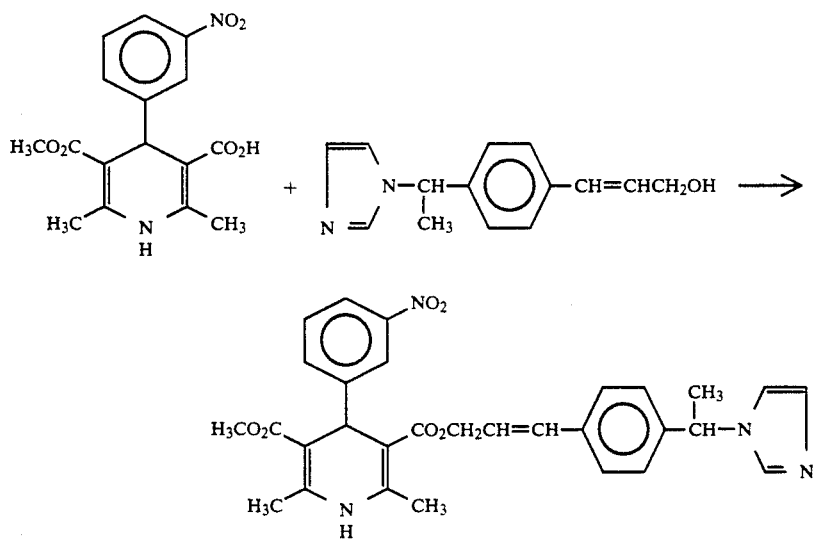

332 mg (1 mM) of 1,4-dihydro-2,6-dimethyl-5-methoxycarbonyl-4-(3-nitrophenyl)pyridine-3-carboxylic acid together with 228 mg (1 mM) of (E)-3-[4{-1-(1-imidazolyl)ethyl)phenyl]-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled off, the residue was purified by chromatography on a silica gel column, whereby the captioned compound was obtained. The yield was 519 mg (95.7%).

Melting point (° C.) 107–109.
NMR $\delta CDCl_3$ : 1.87 (d, 3H, J=7.8Hz), 2.37 (s, 3H), 2.39 (s, 3H), 3.63 (s, 3H), 4.65 (dd, 1H, J=13Hz, 6Hz), 4.75 (dd, 1H, J=13Hz, 6Hz), 5.13 (s, 1H), 5.30 (s, 1H), 5.35 (q, 1H, J=7.8Hz), 6.22 (dt, 1H, J=15Hz, 6Hz), 6.50 (d, 1H, J=15Hz), 6.95 (s, 1H), 7.09 (s, 1H), 7.11 (d, 2H, J=8.4Hz), 7.31 (d, 2H, J=8.4Hz), 7.34 (t, 1H, J=8.8Hz), 7.63 (s, 1H), 7.64 (dt, 1H, J=8.8Hz, 2Hz), 7.98 (ddd, 1H, J=8.8Hz, 2Hz, 1Hz), 8.13 (dd, 1H, J=2Hz, 1Hz).

| IR (cm$^{-1}$) | $\nu$CO | 1698 |
| --- | --- | --- |
|  | $\nu$NO$_2$ | 1528, 1350 |
| Mass Spectrometric Analysis | Molecular formula | C$_{30}$H$_{30}$N$_4$O$_6$ |
|  | Found | 542.21549 |
|  | Calcd. | 542.21650 |

EXAMPLE 25

(E)-3-[6-(1-imidazolylmethyl)pyridine-2-yl]-2-propen-1-yl methyl 1,4-dihydro-2,6-dimethyl-4-(3-nitrophenyl)pyridine-3,5-dicarboxylate:

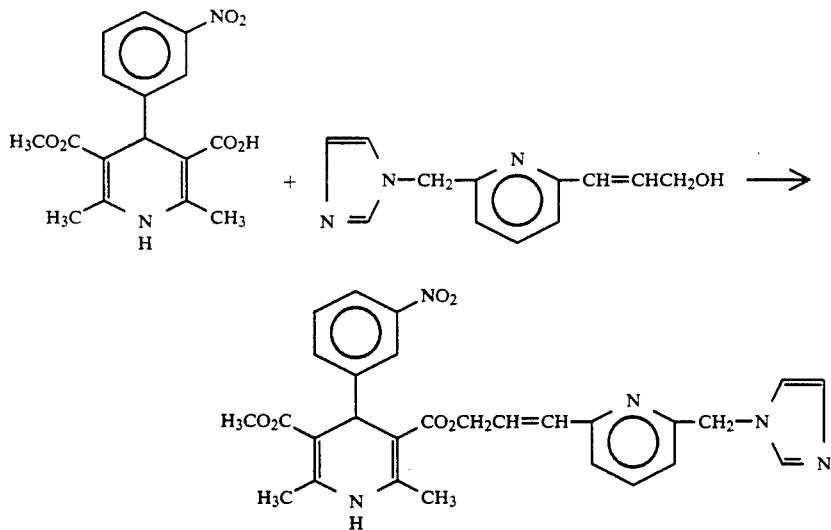

332 mg (1 mM) of 1,4-dihydro-2,6-dimethyl-5-methoxycarbonyl-4-(3-nitrophenyl)pyridine-3-carboxylic acid together with 215 mg (1 mM) of (E)-3-{6-(1-imidazolylmethyl)pyridine-2-yl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 506 mg (95.7%).

Melting point (° C.) 198.5–199.1.

NMR δCDCl$_3$: 2.38 (s, 3H), 2.42 (s, 3H), 3.65 (s, 3H), 4.72 (dd, 1H, J=14Hz, 6Hz), 4.84 (dd, 1H, J=14Hz, 6Hz), 5.16 (s, 1H), 5.26 (s, 1H), 6.10 (s, 1H), 6.50 (d, 1H, J=15.6Hz), 6.74 (dt, 1H, J=15.6Hz, 6Hz), 6.84 (d, 1H, J=8Hz), 7.06 (s, 1H), 7.14 (d, 1H, J=8Hz), 7.16 (s, 1H), 7.37 (t, 1H, J=8Hz), 7.61 (t, 1H, J=8Hz), 7.66 (dt, 1H, J=8Hz, 1Hz), 7.80 (s, 1H), 7.98 (ddd, 1H, J=8.1Hz, 2Hz, 1Hz), 8.15 (dd, 1H, J=2Hz, 1H).

| IR (cm$^{-1}$) | νCO | 1706 |
|---|---|---|
| | νNO$_2$ | 1534, 1354 |
| Mass Spectrometric | Molecular formula | C$_{28}$H$_{27}$N$_5$O$_6$ |
| Analysis | Found | 529.19715 |
| | Calcd. | 529.19610 |

EXAMPLE 26

2-[{4-(1-imidazolylmethyl)benzylideneamino}oxy]ethyl methyl 1,4-dihydro-2,6-dimethyl-4-(3-nitrophenyl)pyridine-3,5-dicarboxylate:

thyl)benzaldoxime were dissolved in 5 ml of dried acetonitrile, and then to the solution 58 mg (0.42 mM) of anhydrous potassium carbonate was added. After the mixture was heated under reflux for 15 hours, acetonitrile was distilled away and dichloromethane was added to the residue. After washing with water, the residue was dried over anhydrous sodium sulfate and dichloromethane was distilled away, and then the crystals were recrystallized from methanol, whereby the captioned compound was obtained. The yield was 400 mg (94%).

Melting point (° C.) 149–151.

NMR δCDCl$_3$: 2.35 (s, 3H), 2.37 (s, 3H), 3.61 (s, 3H), 4.26–4.40 (m, 4H), 5.10 (s, 1H), 5.18 (s, 2H), 6.00 (s, 1H), 6.95 (s, 1H), 7.15 (s, 1H), 7.16 (d, 2H, J=8.4Hz), 7.33 (t, 1H, J=7.8Hz), 7.55 (d, 2H, J=8.4Hz), 7.66 (dt, 1H, J=7.8Hz, 2Hz), 7.78 (s, 1H), 7.96 (ddd, 1H, J=7.8Hz, 2Hz, 1Hz), 8.00 (s, 1H), 8.10 (dd, 1H, J=2Hz, 1Hz).

| IR (cm$^{-1}$) | νCO | 1690 |
|---|---|---|
| | νNO$_2$ | 1532, 1354 |
| Mass Spectrometric | Molecular formula | C$_{29}$H$_{29}$N$_5$O$_7$ |
| Analysis | Found | 559.20644 |
| | Calcd. | 559.20666 |

EXAMPLE 27 di-(E)-3-[4-(1-imidazolylmethyl)phenyl]-2-propen-

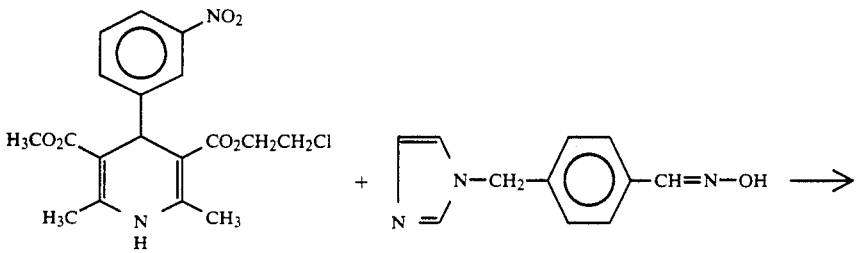

301 mg (0.763 mM) of 2-chloroethyl methyl 1,4-dihydro2,6-dimethyl-4-(3-nitrophenyl)pyridine-3,5-dicarboxylate and 155 mg (0.763 mM) of 4-(1-imidazolylme- 1-yl 1,4-dihydro-2,6-dimethyl-4-(3-nitrophenyl)pyridine-3,5-dicarboxylate:

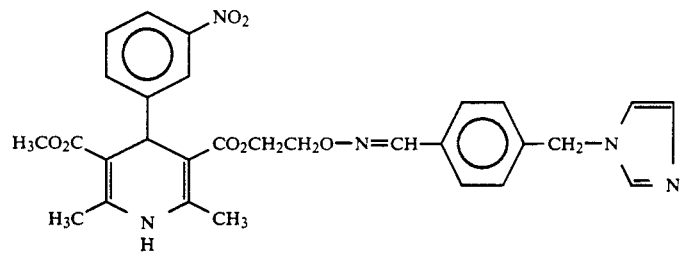

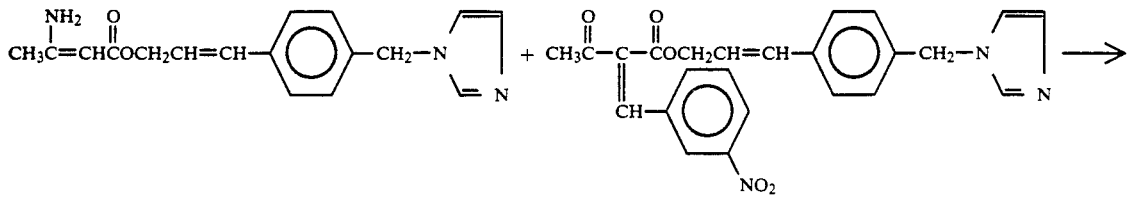

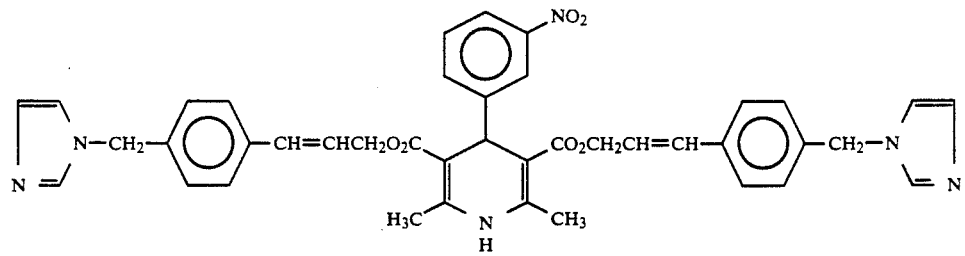

297 mg (1 mM) of 3-[4-(1-imidazolylmethyl)phenyl]-2-propen-1-yl 3-aminocrotonate and 431 mg (1 mM) of 3-[4-(1-imidazolylmethyl)phenyl]-propen-1-yl 2-(3-nitrobenzylidene)acetoacetate were dissolved in 5 ml of toluene and refluxed for six hours. After cooling, the crystals produced were filtered off and recrystallized from methanol., whereby the captioned compound was obtained. The yield was 571 mg (80.4%).

Melting point (° C.) 124.4–125.9.

NMR δCDCl$_3$ :2.39 (s, 6H), 4.65 (ddd, 2H, J=13Hz, 6Hz, 2Hz), 4.75 (ddd, 2H, J=13Hz, 6Hz, 2Hz), 5.10 (s, 4H), 5.17 (s, 1H), 6.08 (bs, 1H), 6.20 (dt, 2H, J=16Hz, 6Hz), 6.48 (d, 2H, J=16Hz), 6.90 (s, 2H), 7.08 (d, 4H, J=8Hz), 7.10 (s, 2H), 7.29 (d, 4H, J=8Hz), 7.32 (t, 1H, J=8Hz), 7.54 (s, 2H), 7.65 (d, 1H, J=8Hz), 7.95 (dd, 1H, J=8Hz, 2Hz), 8.16 (t, 1H, J=2Hz).

| IR (cm$^{-1}$) | νCO | 1695 |
|---|---|---|
| | νNO$_2$ | 1530, 1350 |

FAB mass. 711 (M+1).

EXAMPLE 28

6-(1-imidazolylmethyl)benzoxazol-2-yl-methyl methyl 1,4-dihydro-2,6-dimethyl-4-(3-nitrophenyl)pyridine-3,5-dicarboxylate:

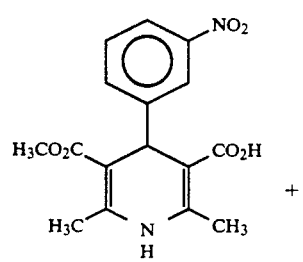

+

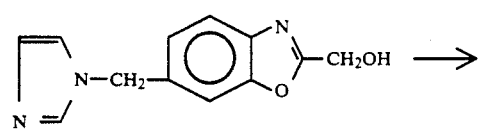

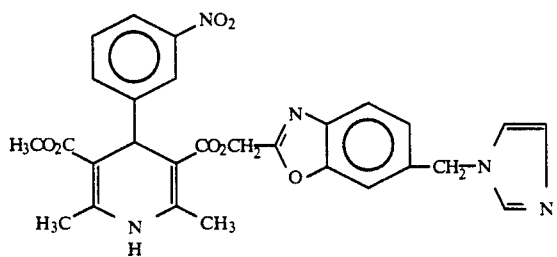

332 mg (1 mM) of 1,4-dihydro-2,6-dimethyl-5-methoxycarbonyl-4-(3-nitrophenyl)pyridine-3-carboxylic acid together with 229 mg (1 mM) of 2-hydroxymethyl-6-(1-imidazolylmethyl)benzoxazole 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled off, the residue was purified by chromatography on a silica gel column, whereby the captioned compound was obtained. The yield was 542 mg (99.9%).

NMR δCDCl$_3$ : 2.37 (s, 3H), 2.41 (s, 3H), 3.62 (s, 3H), 5.13 (s, 1H), 5.20 (d, 1H, J=14Hz), 5.26 (s, 2H), 5.40 (d, 1H, J=14Hz), 6.59 (s, 1H), 6.97 (s, 1H), 7.14 (s, 1H), 7.19 (d, 1H, J=8Hz), 7.20 (s, 1H), 7.25 (t, 1H, J=8Hz), 7.60 (d, 1H, J=8Hz), 7.62 (s, 1H), 7.68 (d, 1H, J=,8Hz), 7.89 (dd, 1H, J=8Hz, 2Hz), 8.08 (t, 1H, J=2Hz).

| IR (cm$^{-1}$) | | νCO | 1705 |
|---|---|---|---|
| | | νNO$_2$ | 1525, 1345 |
| Mass Spectrometric | | Molecular formula | C$_{28}$H$_{25}$N$_5$O$_7$ |
| Analysis | | Found | 543.17657 |
| | | Calcd. | 543.17536 |

EXAMPLE 29

(E)-4-[4-(1-imidazolylmethyl)phenyl]-3-buten-1-yl methyl 1,4-dihydro-2,6-dimethyl-4-(3-nitrophenyl)pyridine-3,5-dicarboxylate:

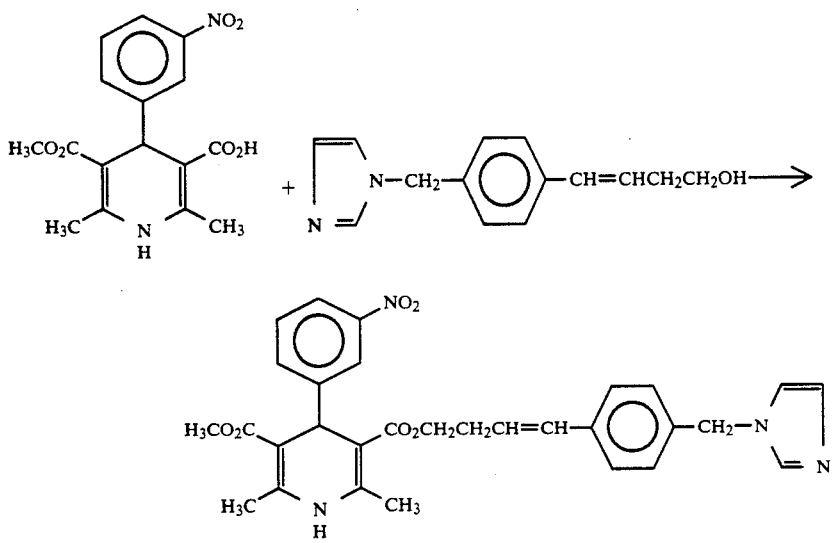

332 mg (1 mM) of 1,4-dihydro-2,6-dimethyl-5-methoxycarbonyl-4-(3-nitrophenyl)pyridine-3-carboxylic acid together with 228 mg (1 mM) of (E)-4{-4-(1-imidazolylmethyl)phenyl}-3-buten-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 400 mg (73.8%).

Melting point (° C.) 178.9–180.1.

NMR δCDCl$_3$: 2.35 (s, 3H), 2.36 (s, 3H), 2.51 (dt, 2H, J=6Hz, 6Hz), 3.59 (s, 3H), 4.14 (dt, 1H, J=12Hz, 6Hz), 4.21 (dt, 1H, J=12Hz, 6Hz), 5.09 (s, 3H), 5.84 (s, 1H), 6.07 (dt, 1H, J=16Hz, 6Hz), 6.36 (d, 1H, J=16Hz), 6.91 (s, 1H), 7.08 (d, 2H, J=8Hz), 7.09 (s, 1H), 7.25 (d, 2H, J=8Hz), 7.29 (t, 1H, J=8Hz), 7.55 (s, 1H), 7.61 (d, 1H, J=8Hz), 7.93 (dd, 1H, J=8Hz, 2Hz), 8.09 (t, 1H, J=2Hz).

| IR (cm$^{-1}$) | νCO | 1700 |
|---|---|---|
|  | νNO$_2$ | 1530, 1345 |
| Mass Spectrometric Analysis | Molecular formula | C$_{30}$H$_{30}$N$_4$O$_6$ |
|  | Found | 542.21571 |
|  | Calcd. | 542.21650 |

EXAMPLE 30

Isopropyl (E)-3-[4-(1-imidazolylmethyl)phenyl]-2-propen-1-yl 1,4-dihydro-2,6-dimethyl-4-(3-nitrophenyl)pyridine-3,5-dicarboxylate:

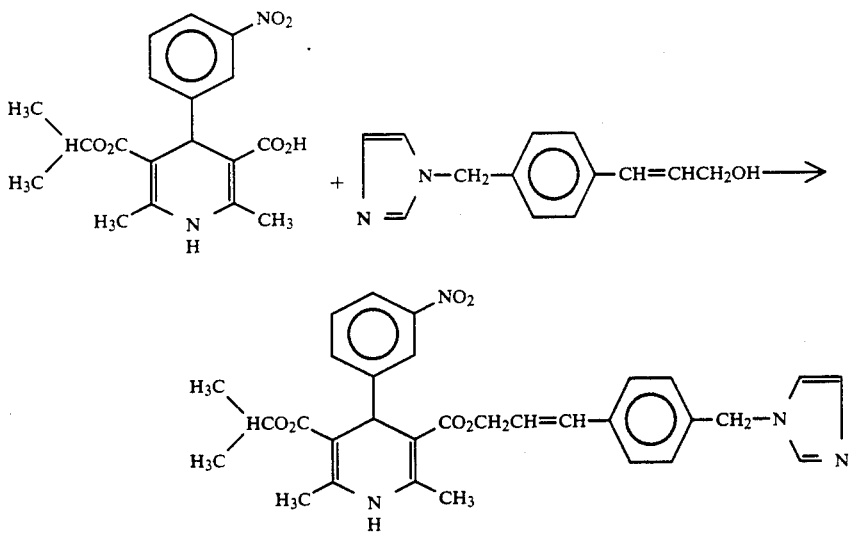

360 mg (1 mM) of 1,4-dihydro-2,6-dimethyl-5-isopropyloxycarbonyl-4-(3-nitrophenyl)pyridine -3carboxylic acid together with 215 mg (1 mM) of (E)-3-{4-(1-imidazolylmethyl)phenyl}-2-propen-1-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 541 mg (97.2%).

NMR δCDCl₃ : 1.09 (d, 3H, J=6Hz), 1.25 (d, 3H, J=6Hz), 2.36 (s, 3H), 2.39 (s, 3H), 4.65 (dd, 1H, J=13Hz, 6Hz), 4.75 (dd, 1H, 13Hz, 6Hz), 4.95 (qq, 1H, J=6Hz, 6Hz), 5.11 (s, 3H), 5.80 (s, 1H), 6.20 (dt, 1H, J=16hz, 6Hz), 6.49 (d, 1H, J=16Hz), 6.91 (s, 1H), 7.09 (s, 1H), 7.11 (d, 2H, J=8Hz), 7.30 (d, 2H, J=8Hz), 7.34 (t, 1H, J=8Hz), 7.55 (s, 1H), 7.64 (d, 1H, J=8Hz), 7.97 (dd, 1H, J=8hz, 2Hz), 8.14 (t, 1H, J=2Hz).

| IR (cm⁻¹) | νCO | 1700 |
|---|---|---|
| | νNO₂ | 1530, 1350 |
| Mass Spectrometric Analysis | Molecular formula | C₃₁H₃₂N₄O₆ |
| | Found | 556.23184 |
| | Calcd. | 556.23214 |

EXAMPLE 31

(E)-4-[4-(1-imidazolylmethyl)phenyl]-3-buten-2-yl methyl 1,4-dihydro-2,6-dimethyl-4-(3-nitrophenyl)pyridine-3,5-dicarboxylate:

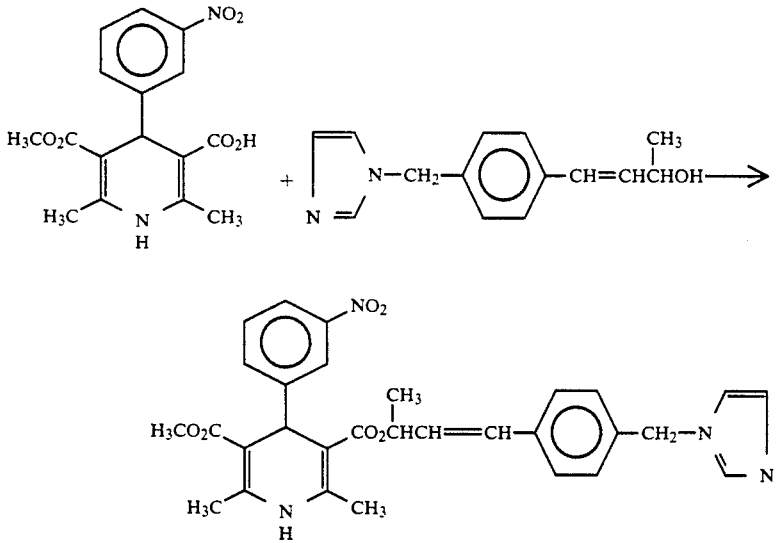

332 mg (1 mM) of 1,4-dihydro-2,6-dimethyl-5-methoxycarbonyl-4-(3-nitrophenyl)pyridine-3-carboxylic acid together with 228 mg (1 mM) of (E)-4-{4-(1-imidazolylmethyl)phenyl)-3-buten-2-ol, 248 mg (1.2 mM) of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled off, the residue was purified by chromatography on a silica gel column. Two kinds of diastereomers were eluted by silica gel column chromatography with a eluate consisting of a mixture of hexane, ethyl acetate and methanol in a ratio of 5:5:1. The first eluted moiety is referred to as "Compound a", and the later eluted moiety is referred to as "Compound b".

| Yield: | "Compound a" | 220 mg |
|---|---|---|
| | "Compound b" | 180 mg |

Compounds a and b have characteristics as shown below.

Compound a
Melting point (° C.) 179.1–180.9.

NMR δCDCl₃ :1.43 (d, 3H, J=6Hz), 2.36 (s, 3H), 2.38 (s, 3H), 3.65 (s, 3H), 5.09 (s, 2H), 5.11 (s, 1H), 5.48 (dq, 1H, J=6Hz, 6Hz), 5.85 (s, 1H), 5.99 (dd, 1H, J=16Hz, 6Hz), 6.25 (d, 1H, J=16Hz), 6.90 (s, 1H), 7.07 (d, 2H, J=8Hz), 7.08 (s, 1H), 7.18 (d, 2H, J=8Hz), 7.31 (t, 1H, J=8Hz), 7.55 (s, 1H), 7.64 (d, 1H, J=8Hz), 7.94 (dd, 1H, J=8Hz, 2Hz), 8.13 (t, 1H, J=2Hz).

| IR (cm⁻¹) | νCO | 1695 |
|---|---|---|
| | νNO₂ | 1530, 1350 |
| Mass Spectrometric Analysis | Molecular formula | C₃₀H₃₀N₄O₆ |
| | Found | 542.21648 |
| | Calcd. | 542.21650 |

Compound b
NMR δCDCl₃ :1.27 (d, 3H, J=6Hz), 2.36 (s, 3H), 2.37 (s, 3H), 3.64 (s, 3H), 5.11 (s, 2H), 5.12 (s, 1H), 5.48 (dq, 1H, J=6Hz, 6Hz), 5.89 (s, 1H), 6.22 (dd, 1H, J=16Hz, 6Hz), 6.55 (d, 1H, J=16Hz), 6.90 (s, 1H), 7.10 (s, 1H), 7.11 (d, 2H, J=8Hz), 7.36 (d, 2H, J=8Hz), 7.38 (t, 1H, J=8Hz), 7.56 (s, 1H), 7.64 (d, 1H, J=8Hz), 8.00 (dd, 1H, J=8Hz, 2Hz), 8.14 (t, 1H, J=2Hz).

| IR (cm⁻¹) | νCO | 1695 |
|---|---|---|
| | νNO₂ | 1535, 1350 |
| Mass Spectrometric Analysis | Molecular formula | C₃₀H₃₀N₄O₆ |
| | Found | 542.21708 |
| | Calcd. | 542.21650 |

EXAMPLE 32

3-[4-(1-imidazolylmethyl)phenyl]-2-propyne-1-yl methyl 1,4-dihydro-2,6-dimethyl-4-(3-nitrophenyl)pyridine-3,5-dicarboxylate:

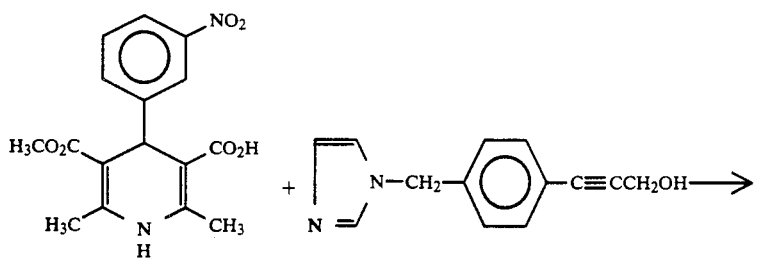

332 mg (1 mM) of 1,4-dihydro-2,6-dimethyl-5-methoxycarbonyl-4-(3-nitrophenyl)pyridine-3-carboxylic acid together with 212 mg (1 mM) of 3-[4-(1-imidazolylmethyl)phenyl]-2-propyn-1-ol, 248 mg (1.2 mM of dicyclohexylcarbodiimide and 134 mg (1.1 mM) of 4-N,N-dimethylaminopyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 421 mg (80%).

Melting point (° C.) 143–144.

NMR δCDCl$_3$: 2.38 (s, 3H), 2.40 (s, 3H), 3.64 (s, 3H), 4.82 (d, 1H, J=16Hz), 4.91 (d, 1H, J=16Hz), 5.14 (s, 1H), 5.18 (s, 2H), 5.96 (s, 1H), 6.94 (s, 1H), 7.12 (d, 2H, J=8Hz), 7.16 (s, 1H), 7.32 (t, 1H), 7.40 (d, 2H, J=8Hz), 7.68 (dt, 1H, J=8Hz, 2Hz), 7.82 (s, 1H), 7.97 (ddd, 1H, J=8Hz, 2Hz, 1Hz), 8.13 (dd, 1H, J=2Hz, 1Hz).

| IR (cm$^{-1}$) | νCO | 1700 |
| | νNO$_2$ | 1530, 1352 |
| Mass Spectrometric Analysis | Molecular formula | C$_{29}$H$_{26}$N$_4$O$_6$ |
| | Found | 526.18449 |
| | Calcd. | 526.18520 |

EXAMPLE 33

(E)-5-[4-(1-imidazolylmethyl)phenyl]-pent-2-en-4-yne-1yl methyl 1,4-dihydro-2,6-dimethyl-4-(3-nitrophenyl)pyridine-3,5-dicarboxylate:

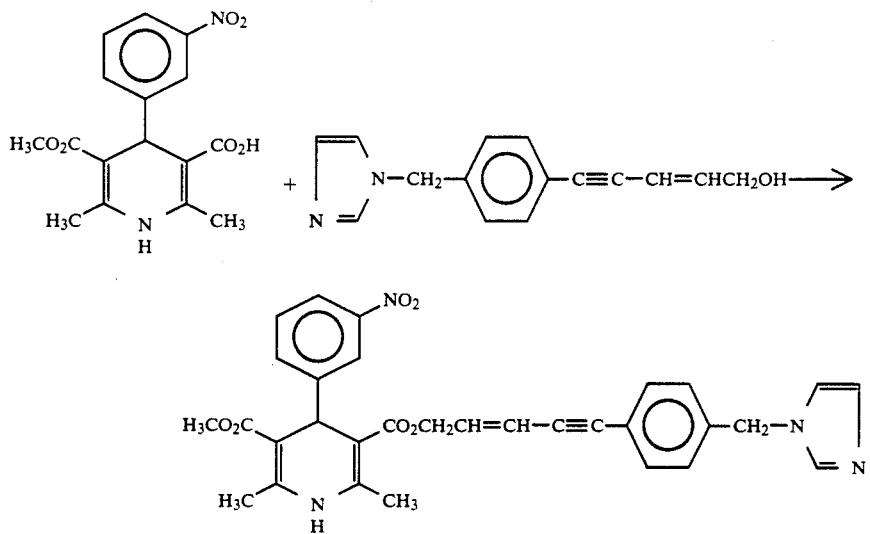

30 mg (0.089 mM) of 1,4-dihydro-2,6-dimethyl-5-methoxycarbonyl-4-(3-nitrophenyl)pyridine-3-carboxylic acid together with 21 mg (0.089 mM) of (E)-5-[4-(1-imidazolylmethyl)phenyl)-pent-2-en-4-yn-1-ol, 22 mg (0.107 mM) of dicyclohexylcarbodiimide and 12 mg (0.098 mM) of 4-N,N-dimethylaminopyridine were dissolved in 3 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 49 mg (87%).

Melting point (° C.) 177–178.

NMR δCDCl$_3$:41 2.38 (s, 3H), 2.40 (s, 3H), 3.66 (s, 3H), 4.61 (dd, 1H, J=15Hz, 6Hz), 4.68 (dd, 1H, J=15Hz, 6Hz), 5.12 (s, 1H), 5.23 (s, 2H), 5.78 (d, 1H, J=16Hz), 5.85 (s, 1H), 6.21 (dt, 1H, J=16Hz, 6Hz), 6.97 (s, 1H), 7.17 (d, 2H, J=8Hz), 7.22 (s, 1H), 7.39 (t, 1H, J=8Hz), 7.45 (d, 2H, J=8Hz), 7.64 (dt, 1H, J=8Hz, 2Hz), 8.01 (ddd, 1H, J=8Hz, 2Hz, 1Hz), 8.09–8.14 (m, 2H).

| IR (cm$^{-1}$) | νCO | 1690 |
|---|---|---|
| | νNO$_2$ | 1530, 1350 |
| Mass Spectrometric Analysis | Molecular formula | C$_{31}$H$_{28}$N$_4$O$_6$ |
| | Found | 552.20148 |
| | Calcd. | 552.20085 |

EXAMPLE 34

(Z)-3-[4-(1-imidazolylmethyl)phenyl]-2-propen-1-yl methyl 1,4-dihydro-2,6-dimethyl-4-(3-nitrophenyl)pyridine-3,5-dicarboxylate:

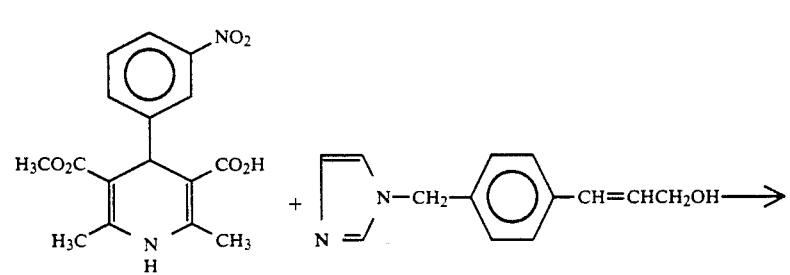

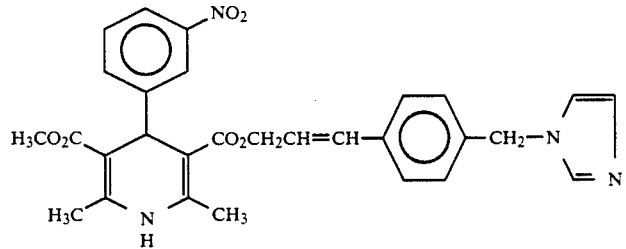

332 mg (1 mM) of 1,4-dihydro-2,6-dimethyl-5-methoxycarbonyl-4-(3-nitrophenyl)pyridine-3-carboxylic acid together with 215 mg (1 mM) of (Z)-3-[4-(1-imidazolylmethyl)phenyl]-2-propen-1-ol, 248 mg (1.2 mM) of dicyclohexylcarbodiimide and 134 mg (1.1 mM) of 4-N,N-dimethylamino-pyridine were dissolved in 5 ml of toluene, while heating, and refluxed for six hours. The solution was cooled to room temperature, and the crystals produced were filtered off. The filtrate was washed with water and dried over anhydrous sodium sulfate. After the solvent was distilled away, the residue was purified by chromatography on a silica gel column, whereby the captioned compound was obtained. The yield was 528 mg (100%).

Melting point (° C.) 75–77.

NMR δCDCl$_3$: 2.37 (s, 6H), 3.64 (s, 3H), 4.77 (d, 2H, J=7Hz), 5.10 (s, 1H), 5.13 (s, 2H), 5.81 (dt, 1H, J=12Hz, 7Hz), 6.21 (s, 1H), 6.60 (d, 1H, J=12Hz), 6.93 (s, 1H), 7.10 (d, 2H, J=9Hz), 7.13 (s, 1H), 7.15 (d, 2H, J=9Hz), 7.35 (t, 1H, J=8.4Hz), 7.63 (ddd, 1H, J=8.4Hz, 2Hz, 1Hz), 7.66 (s, 1H), 7.97 (ddd, 1H, J=8.4Hz, 2Hz, 1Hz), 8.11 (t, 1H, J=2Hz).

| IR (cm$^{-1}$) | νCO | 1698 |
|---|---|---|
| | νNO$_2$ | 1530, 1350 |
| Mass Spectrometric Analysis | Molecular formula | C$_{29}$H$_{28}$N$_4$O$_6$ |
| | Found | 528.20189 |
| | Calcd. | 528.20085 |

EXAMPLE 35

2-[4-(1-imidazolylmethyl)benzylideneamino]ethyl methyl 1,4-dihydro-2,6-dimethyl-4-(3-nitrophenyl)pyridine-3,5-dicarboxylate:

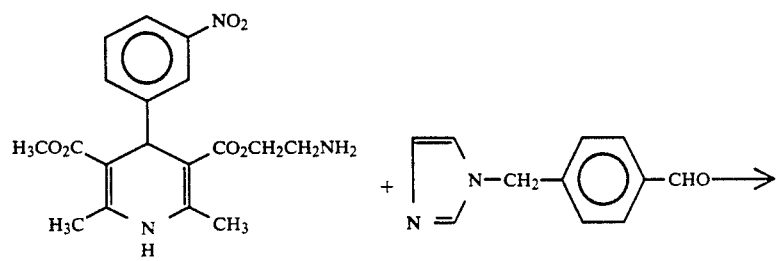

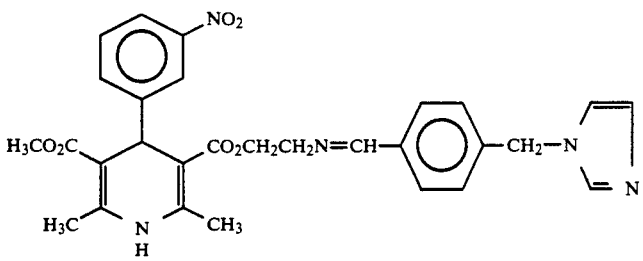

506 mg (1.35 mM) of 2-aminoethyl methyl 1,4-dihydro-2,6-dimethyl-4-(3-nitrophenyl)pyridine -3,5-dicarboxylate was mixed with 251 mg (1.35 mM) of 4-(1-imidazolylmethyl)benzaldehyde and the mixture was stirred for 15 hours at room temperature, whereby the captioned compound was obtained. The yield was 544 mg (100%).

Melting point (° C.) 153 (dec.).

NMR δCDCl$_3$:2.32 (s, 3H), 2.33 (s, 3H), 3.55 (s, 3H), 3.80 (t, 2H, J=5Hz), 4.32–4.47 (m, 2H), 5.05 (s, 1H), 5.11 (s, 2H), 5.93 (s, 1H), 6.93 (s, 1H), 7.11 (s, 1H), 7.18 (d, 2H, J=9Hz), 7.24 (t, 1H, J=9Hz), 7.57 (dt, 1H, J=9Hz, 2Hz), 7.66 (d, 2H, J=9Hz), 7.88 (dt, 1H, J=9Hz, 2Hz), 8.23 (t, 1H, J=2Hz), 8.20 (s, 1H).

| IR (cm$^{-1}$) | νCO | 1698 |
|---|---|---|
| | νNO$_2$ | 1530, 1348 |
| Mass Spectrometric Analysis | Molecular formula | C$_{29}$H$_{29}$N$_5$O$_6$ |
| | Found | 543.21105 |
| | Calcd. | 543.21175 |

Control experiments of the derivatives of the invention were carried out as follows:

1. Experiment for hypotensive activity:

Male spontaneously hypertensive rats (SHR) were used. An arterial blood pressure in conscious SHR was measured through the catheterized abdominal aorta by a pressure transducer (sold by Nihon Kohden K. K. under the tradename of MPU-0.5). Test compounds and reference compounds were injected into the caudal vein. NIFEDIPINE and NICARDIPINE were used as controls. The results are shown in Table 1.

2. Experiment for inhibitory activity on KCl-induced contraction of aorta:

Thoracic aortas were isolated from male rabbits and cut into helical strips. The preparations were mounted vertically in organ baths containing 30 ml of a Krebs-Henseleit solution. The tissue solution was maintained at 37° C. and bubbled with a mixture of 95% O$_2$ and 5% CO$_2$. After 90-minute equilibration, the contraction induced by the application of 30 mM KCl was measured isometrically. Test and reference compounds were added to the bath 30 minutes after KCl treatment. The inhibitory effects of test and reference compounds were determined 60 minutes later. The results are shown in Table 1.

TABLE 1

| Derivatives of the Invention Example No. | Hypotensive effect - Max 100 μg (mm Hg) | Inhibitory effect on KCl-induced contraction 60 min 10$^{-6}$M (%) |
|---|---|---|
| 1 | 28.8 | 41.1 |
| 2 | 50.0 | 39.7 |
| 3 | 27.5 | 35.3 |
| 4 | 62.5 | 76.4 |
| 5 | 37.5 | 69.4 |
| 6 | 20.8 | 50.0 |
| 7 | 32.5 | 39.5 |
| 8 | 30.0 | 64.0 |
| 9 | 5.0 | 48.2 |
| 10 | 41 | 30.0 |
| 11 | 20 | 30.0 |
| 12 | 40 | 64.5 |
| 13 | 25.7 | 86.7 |
| 14 | 36.0 | 25.6 |
| 15 | 25.0 | 21.6 |
| 16 | 34.0 | 27.3 |
| 17 | 30.0 | 55.1 |
| 18 | 22.5 | 88.2 |
| 19 | 25.0 | 68.8 |
| 20 | 37.5 | 68.8 |
| 21 | 15.0 | 37.8 |
| 22 | 38.0 | 11.0 |
| 23 | 44.0 | 21.6 |
| 24 | 35.0 | 74.3 |
| 25 | 12.5 | 88.3 |
| 26 | 30.0 | 74.8 |
| NIFEDIPINE | 55 (30 μg) | 87.6 |
| NICARDIPINE | 100 (30 μg) | 91.1 |

3. Experiment for inhibitory activity on platelet aggregation in rabbit:

Rabbit platelet rich plasma PRP) was prepared by centrifugation of the citrated blood at 380 g for 10 minutes at 20° C. A test solution (10 μl) containing the compound to be tested with a concentration (mol/l) as shown in Table 2 was added to PRP (200 μl) 30 minutes before treatment of aggregation agents (10 μl). The extend of aggregation was expressed with the maximum change in light transmission for PRP and platelet poor plasma was taken as a value of 100%.

Aggregating agents (final concentration):

| Arachidonic acid (AA) | 1 mM |
|---|---|
| Adenosine diphosphate (ADP) | 5 mM |
| Platelet activating factor (PAF) | 10 mg/ml |

The results are shown in Table 2.

TABLE 2

| Derivatives of the Invention Example No. | Collagen 10$^{-4}$ (mol/l) | AA 10$^{-4}$ (mol/l) | ADP 10$^{-4}$ (mol/l) | PAF 10$^{-4}$ (mol/l) |
|---|---|---|---|---|
| 1 | 19.5% | 26.2% | 7.3% | 35.4% |
| 2 | 23.5 | 12.6 | 5.5 | 0 |
| 3 | 33.2 | 19.3 | 2.2 | 0 |
| 4 | 30.5 | 30.8 | −2.2 | 95.6 |
| 5 | 32.3 | 33.4 | 12.0 | 100 |
| 6 | 27.2 | 15.6 | 6.5 | 0 |
| 7 | 30.9 | 17.8 | 4.3 | 0 |
| 8 | 18.9 | 18.8 | 10.8 | 28.9 |
| 9 | 11.1 | 5.9 | 6.5 | 78.8 |
| 10 | 5.5 | 5.0 | 2.1 | 24.4 |
| 11 | 7.1 | 2.9 | 1.3 | 31.1 |

TABLE 2-continued

| Derivatives of the Invention Example No. | Collagen $10^{-4}$ (mol/l) | AA $10^{-4}$ (mol/l) | ADP $10^{-4}$ (mol/l) | PAF $10^{-4}$ (mol/l) |
|---|---|---|---|---|
| 12 | 10.3 | 11.4 | 7.3 | 51.8 |
| 13 | 6.3 | 17.4 | 10.9 | 49.6 |
| 14 | 69.6 | 42.0 | 4.3 | 44.7 |
| 15 | 10.5 | 30.2 | 8.8 | 74.1 |
| 16 | 24.7 | 33.7 | 7.1 | 42.4 |
| 17 | 55.0 | 37.8 | 10.5 | 39.7 |
| 18 | 61.8 | 30.4 | 8.8 | 48.6 |
| 19 | 66.3 | 35.5 | 17.2 | 41.5 |
| 20 | 32.3 | 30.4 | 9.5 | 0 |
| 21 | 29.5 | 37.6 | 17.3 | 25.4 |
| 22 | 24.7 | 23.2 | 14.7 | 0 |
| 23 | 29.5 | 25.7 | 2.6 | 0 |
| 24 | 27.5 | 28.2 | 7.8 | 18.3 |
| 25 | 22.5 | 27.8 | 0 | 28.5 |
| 26 | 13.5 | 27.6 | 6.0 | 30.0 |
| NIFEDIPINE | 5.1 | 0.2 | 0 | |
| NICARDIPINE | 3.6 | | | 6.9 |

The Optical active 1,4-dihydropyridine derivatives having the following formula (II) can also be employed in the present invention, each leaving a geometrical isomerism E or Z and an optical rotation (+) or (−).

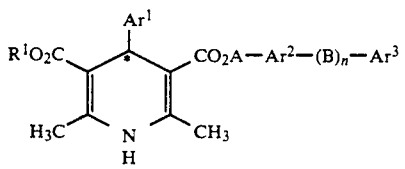

\* optically active site

Specific examples of the optical active 1,4-dihydropyridine derivative are as follows:

(+) or (−)-3-[4-(1-imidazolylmethyl)phenyl]-2-propen-1-yl methyl 1,4 dihydro-2,6-dimethyl-4-phenylpyridine-3,5-dicarboxylate, (+) or (−)-3-[4-(1-imidazolylmethyl)phenyl]-2-propen-1-yl methyl 4-(3-azidophenyl)-1,4-dihydro-2,6-dimethylpyridine-3,-5-dicarboxylate, (+) or (−)-3-[4-(1-imidazolylmethyl)phenyl]-2-propen-1-yl methyl 1,4-dihydro-2,6-dimethyl-4-(3-trichloromethylphenyl)pyridine 3,5-dicarboxylate, (+) or (−)-3-[4-(1-imidazolylmethyl)phenyl]-2-propen-1-yl methyl 4-(3-cyanophenyl)-1,4-dihydro-2,6-dimethylpyridine-3,-5-dicarboxylate, (+) or (−)-3-[4-(1-imidazolylmethyl)phenyl]-2-propen-1-yl methyl 1,4-dihydro-2,6-dimethyl-4-(3-methylphenyl)pyridine-3,-5-dicarboxylate, (+) or (−)-3-[4-(1-imidazolylmethyl)phenyl]-2-propen-1-yl methyl 1,4-dihydro-2,6-dimethyl-4-(3-methoxyphenyl)pyridine-3,5-dicarboxylate, (+) or (−)-3-[4-(1-imidazolylmethyl)phenyl]-2-propen-1-yl methyl 1,4-dihydro-2,6-dimethyl-4-(4-methythiophenyl)pyridine-3,5-dicarboxylate, (+) or (−)-3-[4-(1-imidazolylmethyl)phenyl]-2-propen-1-yl methyl 1,4-dihydro-2,6-dimethyl-4-(3-hydroxyphenyl)pyridine-3,5-dicarboxylate, (+) or (−)-3-[4-(1-imidazolylmethyl)phenyl]-2-propen-1-yl methyl 4-(3-benzyloxyphenyl)-1,4-dihydro-2,6-dimethylpyridine3,5-dicarboxylate, (+) or (−)-3-[4-(1-imidazolylmethyl)phenyl]-2-propen-1-yl methyl 4-(3-cinnamyloxyphenyl)-1,4-dihydro-2,6-dimethylpyridine-3,5-dicarboxylate, (+) or (−)-3-[4-(1-imidazolylmethyl)phenyl]-2-propen-1-yl methyl 4-(3-benzoylphenyl)-l,4-dihydro-2,6-dimethylpyridine-3,5-dicarboxylate, (+) or (−)-3-[4-(1-imidazolylmethyl)phenyl]-2-propen-1-yl methyl 4-(3-chlorophenyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(3-fluorophenyl)pyridine-3,5-dicarboxylate, (+) or (−)-3-[4-(1-imidazolylmethyl)phenyl]-2-propen-1-yl methyl 1,4-dihydro-2,6-dimethyl-4-(2-nitrophenyl)pyridine-3,5-dicarboxylate, (+) or (−)-3-[4-(1-imidazolylmethyl)phenyl]-2-propen-1-yl methyl 1,4-dihydro-2,6-dimethyl-4-(3-nitrophenyl)pyridine-3,5-dicarboxylate, (+) or (−)-3-[4-(1-imidazolylmethyl)phenyl]-2-propen-1-yl methyl 1,4-dihydro-2,6-dimethyl-4-(4-nitrophenyl)pyridine-3,5-dicarboxylate, (+) or (−)-3-[4-(1-imidazolylmethyl)phenyl]-2-propen-1-yl methyl 4-(3-bromophenyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(3-iodophenyl)pyridine-3,5-dicarboxylate, (+) or (−)-3-[4-(1-imidazolylmethyl)phenyl]-2-propen-1-yl methyl 4-(2-chloro-3-nitrophenyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(2-fluoro-3-nitrophenyl)pyridine-3,5-dicarboxylate, (+) or (−)-3-[4-(1-imidazolylmethyl)phenyl]-2-propen-1-yl methyl 4-(3-chloro-2-fluorophenyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(2,3-difluorophenyl)pyridine-3,5-dicarboxylate, (+) or (−)-3-[4-(1-imidazolylmethyl)phenyl]-2-propen-1-yl methyl 1,4-dihydro-2,6-dimethyl-4-(2-furyl)pyridine-3,5-dicarboxylate, (+) or (−)-3-[4-(1-imidazolylmethyl)phenyl]-2-propen-1-yl methyl 1,4-dihydro-2,6-dimethyl-4-(3-furyl)pyridine-3,5-dicarboxylate, (+) or (−)-3-[4-(1-imidazolylmethyl)phenyl]-2-propen-1-yl methyl 1,4-dihydro-2,6-dimethyl-4-(2-thienyl)pyridine-3,5-dicarboxylate, (+) or (−)-3-[4-(1-imidazolylmethyl)phenyl]-2-propen-1-yl methyl 1,4-dihydro-2,6-dimethyl-4-(3-thienyl)pyridine-3,5-dicarboxylate, (+) or (−)-3-[4-(1-imidazolylmethyl)phenyl]-2-propen-1-yl methyl 1,4-dihydro-2,6-dimethyl-4-(1-naphthyl)pyridine-3,5-dicarboxylate, +) or (−)-3-[4-(1-imidazolylmethyl)phenyl3-2-propen-1-yl methyl 1,4-dihydro-2,6-dimethyl-4-(1-isoquinolyl)pyridine-3,-5-dicarboxylate, (+) or (−)-3- 4-(1-imidazolylmethyl)phenyl]-2-propen-1-yl methyl 1,4-dihydro-2,6-dimethyl-4-(2-quinoxalyl)pyridine-3,-5-dicarboxylate, (+) or (−)-3-14-(1-imidazolylmethyl)phenyl)-2-propen-1-yl methyl 4-(2-chloropyridyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(2-methylpyridyl)pyridine-3,5-dicarboxylate, (+) or (−)-3-[4-(1-imidazolylmethyl)phenyl]-2-propen-1-yl methyl 1,4-dihydro-2,6-dimethyl-4-(2-methoxypyridyl)pyridine-3,5-dicarboxylate, (+) or (−)-3-[4-(1-imidazolylmetbyl)phenyl)-2-propen-1-yl methyl 4-(5-bromopyridyl)-1,4-dihydro-2,6-dimethylpyridine-3,5-dicarboxylate, (+) or (−)-3-[4-(1-imidazolylmethyl)phenyl]-2-propen-1-yl methyl 4-(2-aminopyridyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(2-mercaptopyridyl)pyridine-3,5-dicarboxylate, (+) or (−)-3-[4-(1-imidazolylmethyl)phenyl]-2-propen-1-yl methyl 1,4-dihydro-2,6-dimethyl-4-(3-pyridazinyl)pyridine-3,5-dicarboxylate, (+) or (−)-3-[4-(1-imidazolylmethyl)phenyl]-2-propen-1-yl methyl 1,4-dihydro-2,6-dimethyl-4-pyrazinyl-pyridine-3,5-dicarboxylate, (+) or (−)-3-[4-(1-imidazolylmethyl)phenyl]-2-propen-1-yl methyl 1,4-dihydro-2,6-dimethyl-4-(2-pyrimidyl)pyridine-3,5-dicarboxylate, (+) or (−)-3-[4-(1-imidazolylmethyl)phenyl]-2-propen-1-yl methyl 4-(7-benzoxazolyl)-1,4-dihydro-2,6-dimethylpyridine-3,5-dicarboxylate, (+) or (−)-3-[4-(1-imidazolylmethyl)phenyl]-2-propen-1-yl methyl 4-(7-benzothiazolyl)-1,4-dihydro-2,6-dimethylpyridine-3,5-dicarboxylate, (+) or (−)-3-[4-(1-imidazolylmethyl)phenyl]-2-propen-1-yl methyl-4-(2,1,3-benzoxadiazole-3-yl)-1,4-dihydro-2,6-dimethylpyridine-3,5-dicarboxylate, (+) or (−)-3-[4-(1-imidazolylmethyl)phenyl]-2-propen-1-yl methyl 4-(2,1,3-benzothiadiazole-3-yl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(3-indolyl)-pyridine-3,5-dicarboxylate, (+) or (−)-3-[4-(1-imidazolylmethyl)phenyl]-2-propen-1-yl methyl 1,4-dihydro-2,6-dimethyl-4-(2,3,4-trimethoxyphenyl)pyridine-3,5-dicarboxylate, (+) or (−)-3-14-(1-imidazolylmethyl)phenyl]-2-propen-1-yl methyl 1,4-dihydro-2,6-dimethyl-4-(2,3,4-trifluorophenyl)pyridine-3,5-dicarboxylate, (+) or (−)-3-[4-(1-imidazolylmethyl)phenyl]-2-propen-1-yl methyl 1,4-dihydro-2,6-dimethyl-4-(2,3,6-trichlorophenyl)pyridine-3,5-dicarboxylate, (+) or (−)-3-[4-(1-imidazolylmethyl)phenyl]-2-propen-1-yl methyl 1,4-dihydro-2,6-dimethyl-4-(2,4,6-trimethylphenyl)pyridine-3,5-dicarboxylate, (+) or (−)-3-[4-(1-imidazolylmethyl)phenyl]-2-propen-1-yl methyl 1,4-dihydro-2,6-dimethyl-4-(3,4,5-triethoxyphenyl)pyridine-3,5-dicarboxylate, (+) or (−)-3-[4-(1-imidazolylmethyl)phenyl]-2-propen-1-yl methyl 4-(2-chloro-3,5-dinitrophenyl)-1,4-dihydro-2,6-dimethylpyridine-3,5-dicarboxylate, (+) or (−)-3-[4-(1-imidazolylmethyl)phenyl]-2-propen-1-yl methyl 1,4-dihydro-2,6-dimethyl-4-(2-cyanophenyl)pyridine-3,5-dicarboxylate, (+) or (−)-3-[4-(1-imidazolylmethyl)phynyl]-2-propen-1-yl methyl 1,4-dihydro-2,6-dimethyl-4-(3-trifluoromethylphenyl) pyridine-3,5-dicarboxylate, (+) or (−)-3-[4-(1-imidazolylmethyl)phenyl]-2-propen-1-yl methyl 1,4-dihydro-2,6-dimethyl-4-(2,3-dichlorophenyl) pyridine-3,5-dicarboxylate, (+) or (−)-3-[4-(1-imdazolylmethyl)phenyl]-2-propen-1-yl methyl 1,4-dihydro-2,6-dimethyl-4-(4-quinolyl)-pyridine-3,5-dicarboxylate, (+) or (−)-3- 4-(1-imidazolylmethyl)phenyl]-2 -propen-1-yl methyl 1,4-dihydro-2,6-dimethyl-4-(3-pyridyl)pyridine-3,5-dicarboxylate, (+) or (−) methyl 3-[4-(1,2,3,4-tetrazol-1-ylmethyl)-phenyl]-2-propen-1-yl 1,4-dihydro-2,6-dimethyl-4-(3-nitrophenyl) pyridine-3,5-dicarboxylate, (+) or (−) methyl 3-[4-(1,2,4-triazol-1-ylmethyl)-phenyl]-2-propen-1-yl 1,4-dihydro-2,6-dimethyl-4-(3-nitrophenyl) pyridine-3,5-dicarboxylate, (+) or (−)-3-[4-(1,3,4-triazol-1-ylmethyl)phenyl]-2-propen-1-yl 1,4-dihydro-2,6-dimethyl-4-(3-nitrophenyl)pyridine-3,5-dicarboxylate, (+) or (−) methyl 3-[4-(3-pyridylmethyl)phenyl]-2-propen-1-yl 1,4-dihydro-2,6-dimethyl-4-(3-nitrophenyl)pyridine-3,5-dicarboxylate, (+) or (−)-3-[4-(1-imidazolyl)phenyl]-2-propen-1-ylmethyl 1,4-dihydro-2,6-dimethyl -4-(3-nitrophenyl)pyridine-3,5-dicarboxylate, (+) or (−)-3- 6-(1-imidazolylmethyl)pyridine-2-yl]-2-propen-1-yl methyl 1,4-dihydro-2,6-dimethyl-4-(3-nitrophenyl)pyridine-3,5-dicarboxylate, (+) or (−)-3-[3-(1-imidazolylmethyl)phenyl]-2-propen-1-yl methyl 1,4-dihydro-2,6-dimethyl-4-(3-nitrophenyl)pyridine-3,5-dicarboxylate, (+) or (−)-3-[2-(1-imidzolylmethyl)phenyl]-2-propen-1-yl methyl 1,4-dihydro-2,6-dimethyl-4-(3-nitrophenyl)pyridine-3,5-dicarboxylate, (+) or (−)-3-[5-(1-imidazolylmethyl)-2-thiophenel-2-propen 1-yl methyl-1,4-dihydro-2,6-dimethyl-4-(3-nitrophenyl)pyridine-3,5-dicaboxylate, (+) or (−)-3-[5-(1-imidzolylmethyl)-2-furanj-2-propen-1-yl methyl 1,4-dihydro-2,6-dimethyl-4-(3-nitrophenyl)pyridine-3,5-dicarboxylate, (+) or (−)-6-(1-imidzolylmethyl)benzoxazol-2-yl-methyl methyl 1,4-dihydro-2,6-dimethyl-4(3-nitrophenyl)pyridine-3,5-dicarboxylate, (+) or (−)-isopropyl 3-[4-(1-imidazolylmethyl)-phenyl]-2-propen-1-yl 1,4-dihydro-2,6-dimethyl-4-(3-nitrophenyl) pyridine-3,5-di-carboxylate, (+) or (−)-di-3-[4-(l-imidazolylmethyl)phenyl]-2-propen-1-yl 1,4-dihydro-2,6-dimethyl-4-(3-nitrophenyl)-pyridine-3,5-dicarboxylate, (+) or (−)-5-[4-(1-imidazolylmethyl)phenyl]-2,4-pentadien-1-yl methyl-1,4-dihydro-2,6-dimethyl-4-(3-nitrophenyl)pyridine-3,5-dicarboxylate, (+) or (−)-3-[4-(1-imidazolylmethyl)phenyl]-2-propen-1-yl 2-methoxyethyl 1,4-dihydro-2,6-dimethyl-4-(3-nitrophenyl) pyridine-3,5-dicarboxylate, (+) or (−)-2,4-hexadien-1-yl 3-[4-(1-imidazolylmethyl)phenyl] 2-propen-1-yl 1,4-dihydro-2,6-dimethyl-4-(3-nitrophenyl) pyridine-3,5-dicarboxylate, (+) or (−) cinnamyl '-[4-(1-imidazolylmethyl)phenyl]-2-propen-1-yl 1,4-dihydro-2,6-dimethyl-4-(3-nitrophenyl)pyridine-3,5-dicarboxylate, (+) or (−) et 1 3-[4-(1-imidazolylmethyl)phenyl]-2-propen-1-yl 1,4-dihydro-2,6-dimethyl-4-(3-nitrophenyl)-pyridine-3,5-dicarboxylate, (+) or (−)-S-[4-(l-imidazolylmethyl)phenyl]-pent-3-en-4-yne-1-yl methyl 1,4-dihydro-2,6-dimethyl-4-(3-nitrophenyl)pyridine-3,5-dicarboxylate, (+) or (−)-3-[4-(1-imidazolylmethyl)phenyl]-2-propyne-1-yl methyl 1,4-dihydro-2,6-dimethyl-4-(3-nitrophenyl)pyridine-3,5-dicarboxylate, (+) or (−)-4-[4-(1-imidazolylmethyl)phenyl]-3-buten-2-yl methyl 1,4-dihydro-2,6-dimethyl-4-(3-nitrophenyl)pyridine-3,5-dicarboxylate, (+) or (−)-4-[4-(1-imidazolylmethyl)phenyl]-3-buten-1-yl methyl 1,4-dihydro-2,6-dimethyl-4-(3-nitrophenyl)pyridine-3,5-dicarboxylate, (+) or (−)-3-[4-fl-(1-imidazolyl)ethyl)phenyl -2-propen-1-yl methyl 1,4-dihydro-2,6-dimethyl-4-(3-nitrophenyl)pyridine 3,5-dicarboxylate, (+) or (−)-3-14-(1-imidazolylmethyl)phenyl)-2-fluoro-2-propen-1-yl methyl 1,4-dihydro-2,6-dimethyl-4-(3-nitrophenyl) pyridine-3,5-dicarboxylate, (+) or (−)-3-[4-(1-imidazolylmethyl)phenyl]-2-methyl-2-propen-1-yl methyl 1,4-dihydro-2,6-dimethyl-4-(3-nitrophenyl)pyridine-3,5-dicarboxylate, (+) or (−)-3-[4-(1-imidazolylmethyl)pbenyl)-2-buten-1-yl methyl 1,4-dihydro-2,6-dimethyl-4-(3-nitrophenyl)pyridine-3,5-dicarboxylate, (+) or (−)-2-[4-(1-imidazolylmethyl)benzylideneamino)ethyl methyl 1,4-dihydro-2,6-dimethyl-4-(3-nitrophenyl)pyridine-3,5-dicarboxylate, and (+) or (−)-2-[{4-(1-imidazolylmethyl)benylideneamino}oxy]ethylmethyl-1,4-dihydro-2,6-dimethyl -4-(3-nitrophenyl)pyridine-3,5-dicarboxylate.

The optical active 1,4-dihydropyridine derivative of formula (II) can be prepared by either Process A or Process B as shown below:

Process A

In this process, the optical active 1,4-dihydropyridine derivative of formula (II) is prepared by allowing an optical active carboxylic acid derivative having formula (II-1) to react with an alcohol derivative having formula (II-2):

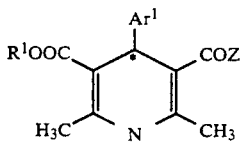

* indicates an optically active cite.

wherein $Ar^1$ represents an aromatic hydrocarbon group or an aromatic heteromonocyclic or heterobicyclic group containing therein 1 to 3 atoms selected from the group consisting of oxygen, sulfur and nitrogen; $R^1$ represents a hydrocarbon group which may have one or more substituents, including $—A—Ar^2—B—Ar^3$, in which A, B, $Ar^2$, and $Ar^3$ respectively the same as defined previously in formula (1), and Z represents a hydroxyl group, a halogen atom, a methyl-sulfonyloxy group or a benzotriazole-1-oxy group.

wherein $R^2$ represents $—A—Ar^2—B—Ar^3$ as represented by $R^1$ when $R^1$ is a hydrocarbon group other than $—A—Ar^2—B—Ar^3$; or when $R^1$ is $—A—Ar^2—B—Ar^3$, $R^2$ is a hydrocarbon group other than $—A—Ar^2—B—Ar^3$.

In this process, optical active carboxylic acid derivatives of formula (II-1) in which Z is a hydroxyl group (hereinafter referred to as the carboxylic acid compounds) can be prepared by the methods as described in Japanese Laid-Open Patent Applications No. 63-20857 and No. 55-6457.

Optical active carboxylic acid derivatives of formula (II-1) in which Z is a halogen (hereinafter referred to as the halogen-substituted carboxylic acid compounds) can be prepared by the halogenation of the above-mentioned carboxylic acid compounds by use of a thionyl halide such as thionyl chloride, or a phosphorous halide such as phosphorous trichlorid phoshorous pentachloride, or phosphorous tribromide.

Optical active carboxylic acid derivatives of formula (II-1) in which Z is an active ester radical (hereinafter referred to as the active ester compounds) can be prepared by allowing the carboxylic acid compounds to react with N-hydroxysuccinimide, N-hydroxyphthalimide, or p-nitrophenol in the presence of a condensing agent such as "DCC"(N,N'-dicyclo-hexylcarbodiimide). The active ester radical in the present invention means, for example, a succinimidoxy group, a phthalimidoxy group, and a p-nitrophenoxy group employed in the field of the so-called peptide synthesis.

Specific examples of the optical active carboxylic acid derivative having formula (II-1) for use in the present invention are as follows:

(+)-1,4-dihydro-2,6-dimethyl-4-(3-nitrophenyl)pyridine-3,5-dicarboxylic acid monomethyl ester, (−)-1,4-dihydro-2,6-dimethyl-4-(3-nitrophenyl)pyridine-3,5-dicarboxylic acid monomethyl ester, (+)-1,4-dihydro-2,6-dimethyl-4-(3-nitrophenyl)pyridine-3,5-dicarboxylic acid mono(E)-3-[4-(1-imidazolylmethyl) phenyl]-2-propen-1-yl ester, (−)-1,4-dihydro-2,6-dimethyl-4-(3-nitrophenyl)pyridine-3,5-dicarboxylic acid mono(E)-3-[4-(1-imidazolylmethyl) phenyl]-2-propen-1-yl ester, (+)-1,4-dihydro-2,6-dimethyl-4-(3-nitrophenyl)pyridine-3,5-dicarboxylic acid mono(Z)-3-[4-(1-imidazolylmethyl) phenyl]-2-propen-1-yl ester, (−)-1,4-dihydro-2,6-dimethyl-4-(3-nitrophenyl)pyridine-3,5-dicarboxylic acid mono(Z)-3-[4-(1-imidazolylmethyl) phenyl]-2-propen-1-yl ester, (+)-1,4-dihydro-2,6-dimethyl-4-(3-nitrophenyl)pyridine-3,5-dicarboxylic acid monochloride monomethyl ester, (−)-1,4-dihydro-2,6-dimethyl-4-(3-nitrophenyl)pyridine-3,5-dicarboxylic acid monochloride monomethyl ester, (+)-1,4-dihydro-2,6-dimethyl-4-(3-nitrophenyl)pyridine-3,5-dicarboxylic acid monochloride mono(E)-3-[4-(1-imidazolylmethyl)phenyl)-2-propen-1-yl ester, (−)-1,4-dihydro-2,6-dimethyl-4-(3-nitrophenyl)pyridine-3,5-dicarboxylic acid monochloride mono(E)-3-[4-(1-imidazolylmethyl)phenyl]-2-propen-1-yl ester, (+)-1,4-dihydro-2,6-dimethyl-4-(3-nitrophenyl)pyridine-3,5-dicarboxylic acid monochloride mono(Z)-3-[4-(1-imidazolylmethyl)phenyl]-2-propen-1-yl ester, (−)-1,4-dihydro-2,6-dimethyl-4-(3-nitrophenyl)pyridine-3,5-dicarboxylic acid monochloride mono(Z)-3-14-(1-imidazolylmethyl)phenyl]-2-propen-1-yl ester, (+)-methyl succinimide-N-yl 1,4-dihydro-2,6-dimethyl-4-(3-nitrophenyl)pyridine-3,5-dicarboxylate, (−)-methyl succinimide-N-yl 1,4-dihydro-2,6-dimethyl-4-(3-nitrophenyl)pyridine-3,5-dicarboxylate, (+)-(E)-3-[4-(1-imidazolylmethyl)phenyl)-2-propen-1-yl succinimide-N-yl 1,4-dihydro-2,6-dimethyl-4-(3-nitrophenyl)pyridine-3,5-dicarboxylate, (−)-(E)-3-[4-(l-imidazolylmethyl)phenyl]-2-propen-1-yl succinimide-N-yl 1,4-dihydro-2,6-dimethyl-4-(3-nitrophenyl)pyridine-3,5-dicarboxylate, (+)-(Z)-3-[4-(I-imidazolylmethyl)phenyl]-2-propen-1-yl succinimide-N-yl 1,4-diphydro-2,6-dimethyl-4-(3-nitrophenyl)pyridine-3,5-dicarboxylate, (−)-(Z)-3-[4-(l-imidazolylmethyl)phenyl3-2-propen-1-yl succinimide-N-yl 1,4-diphydro-2,6-dimethyl-4-(3-nitrophenyl)pyridine-3,5-dicarboxylate, (+)-1,4-dihydro-2,6-dimethyl-4-(3-nitrophenyl)pyridine-3,5-dicarboxylic acid monoethyl ester, (−)-1,4-dihydro-2,6-dimethyl-4-(3-nitrophenyl)pyridine-3,5-dicarboxylic acid monoethyl ester, (+)-1,4-dihydro-2,6-dimethyl-4-(3-nitrophenyl)pyridine-3,5-dicarboxylic acid mono-n-propyl ester,
(−)-1,4-dihydro-2,6-dimethyl-4-(3-nitrophenyl)pyridine-3,5-dicarboxylic acid mono-n-propyl ester,
(+)-1,4-dihydro-2,6-dimethyl-4-(3-nitrophenyl)pyridine-3,5-dicarboxylic acid mono-isopropyl ester,
(−)-1,4-dihydro-2,6-dimethyl-4-(3-nitrophenyl)pyridine-3,5-dicarboxylic acid mono-isopropyl ester,
(+)-1,4-dihydro-2,6-dimethyl-4-(3-nitrophenyl)pyridine-3,5-dicarboxylic acid mono-2-methoxyethyl ester,
(−)-1,4-dihydro-2,6-dimethyl-4-(3-nitrophenyl)pyridine-3,5-dicarboxylic acid mono-2-methoxyethyl ester,
(+)-1,4-dihydro-2,6-dimethyl-4-(3-nitrophenyl)pyridine-3,5-dicarboxylic acid mono-2,4-hexadienyl ester,
(−)-1,4-dihydro-2,6-dimethyl-4-(3-nitrophenyl)pyridine-3,5-dicarboxylic acid mono-2,4-hexadienyl ester,
(+)-1,4-dihydro-2,6-dimethyl-4-(3-nitrophenyl)pyridine-3,5-dicarboxylic acid mono-3-phenyl-2-propen-1-yl ester,
(−)-1,4-dihydro-2,6-dimethyl-4-(3-nitrophenyl)pyridine-3,5-dicarboxylic acid mono-3-phenyl-2-propen-1-yl ester,
(+)-1,4-dihydro-2,6-dimethyl-4-(2-nitrophenyl)pyridine-3,5-dicarboxylic acid monomethyl ester,
(−)-1,4-dihydro-2,6-dimethyl-4-(2-nitrophenyl)pyridine-3,5-dicarboxylic acid monomethyl ester,
(+)-1,4-dihydro-2,6-dimethyl-4-(4-nitrophenyl)pyridine-3,5-dicarboxylic acid monomethyl ester,
(−)-1,4-dihydro-2,6-dimethyl-4-(4-nitrophenyl)pyridine-3,5-dicarboxylic acid monomethyl ester,
(+)-1,4-dihydro-2,6-dimethyl-4-(3-trifluorophenyl)-pyridine-3,5-dicarboxylic acid monomethyl ester,
(−)-1,4-dihydro-2,6-dimethyl-4-(3-trifluorophenyl)-pyridine-3,5-dicarboxylic acid monomethyl ester,
(+)-1,4-dihydro-2,6-dimethyl-4-(4-methoxyphenyl)-pyridine-3,5-dicarboxylic acid monomethyl ester,
(−)-1,4-dihydro-2,6-dimethyl-4-(4-methoxyphenyl)-pyridine-3,5-dicarboxylic acid monomethyl ester,
(+)-I,4-dihydro-2,6-dimethyl-4-pyridylpyridine-3,5-dicarboxylic acid monomethyl ester,
(−)-1,4-dihydro-2,6-dimethyl-4-pyridiylpyridine-3,5-dicarboxylic acid monomethyl ester,
(+)-1,4-dihydro-2,6-dimethyl-4-furylpyridine-3,5-dicarboxylic acid monomethyl ester,
(−)-1,4-dihydro-2,6-dimethyl-4-furylpyridine-3,5-dicarboxylic acid monomethyl ester,
(+)-1,4-dihydro-2,6-dimethyl-4-thienylpyridine-3,5-dicarboxylic acid monomethyl ester,
(−)-1,4-dihydro-2,6-dimethyl-4-thienylpyridine-3,5-dicarboxylic acid monomethyl ester,
(+)-1,4-dihydro-2,6-dimethyl-4-(2-thienyl)pyridine-3,5-dicarboxylic acid monomethyl ester,
(−)-1,4-dihydro-2,6-dimethyl-4-(2-thienyl)pyridine-3,5-dicarboxylic acid monomethyl ester,
(+)-1,4-dihydro-2,6-dimethyl-4-(1-naphthyl)pyridine-3,5-dicarboxylic acid monomethyl ester,
(−)-1,4-dihydro-2,6-dimethyl-4-(1-naphthyl)pyridine-3,5-dicarboxylic acid monomethyl ester,
(+)-1,4-dihydro-2,6-dimethyl-4-(4-quinolyl)pyridine-3,5-dicarboxylic acid monomethyl ester,
(−)-1,4-dihydro-2,6-dimethyl-4-(4-quinolyl)pyridine-3,5-dicarboxylic acid monomethyl ester,
(+)-4-(2-cyanophenyl)-1,4-dihydro-2,6-dimethylpyridine-3,5-dicarboxylic acid monomethyl ester,
(−)-4-(2-cyanophenyl)-1,4-dihydro-2,6-dimethylpyridine-3,5-dicarboxylic acid monomethyl ester,
(+)-4-(2,3-dichlorophenyl)-1,4-dihydro-2,6-dimethyl-pyridine-3,5-dicarboxylic acid monomethyl ester,
(−)-4-(2,3-dichlorophenyl)-1,4-dihydro-2,6-dimethyl-pyridine-3,5-dicarboxylic acid monomethyl ester,
(+)-1,4-dihydro-2,6-dimethyl-4-(3-trichloromethylphenyl) pyridine-3,5-dicarboxylic acid monomethyl ester,
(−)-1,4-dihydro-2,6-dimethyl-4-(3-trichloromethylphenyl) pyridine-3,5-dicarboxylic acid monomethyl ester,
(+)-1,4-dihydro-2,6-dimethyl-4-(4-methylphenyl)pyridine-3,5-dicarboxylic acid monomethyl ester,
(−)-1,4-dihydro-2,6-dimethyl-4-(4-methylphenyl)pyridine-3,5-dicarboxylic acid monomethyl ester,
(+)-1,4-dihydro-2,6-dimethyl-4-(4-methylthiophenyl)-pyridine-3,5-dicarboxylic acid monomethyl ester,
(−)-1,4-dihydro-2,6-dimethyl-4-(4-methylthiophenyl)-pyridine-3,5-dicarboxylic acid monomethyl ester,
(+)-4-(3-azidophenyl)-1,4-dihydro-2,6-dimethylpyridine-3,5-dicarboxylic acid monomethyl ester, and
(−)-4-(3-azidophenyl)-I,4-dihydro-2,6-dimethylpyridine-3,5-dicarboxylic acid monomethyl ester.

Specific examples of the alcohol derivative of formula (II-2) for use in the present invention are methanol, ethanol, n-propanol, isopropanol, 2-methoxyethanol, cinnamyl alcohol, 3-[4-(I-imidazolylmethyl)-phenyl]-2-propen-1-ol, 3-[4-(3-pyridylmethyl)phenyl]-2-propen-1-ol, 3-[4-(1,2,4-triazole-1-yl-methyl) phenyl]-2-propen-1-ol, 3-[4-(1,2,3,4-tetrazole-1-yl-methyl)-phenyl]-2-propen-1-ol, 3-[5-(1-imidazolylmethyl)furan]-2-propen-1-ol, and 5-[4-(1-imidazolylmethyl)furan]-2,4-pentadiene-1-ol.

It is preferable that the previously mentioned carboxylic acid compounds of formula (II-1) be allowed to react with the above-mentioned alcohol derivative of formula (II-2) in the presence of an acid or a condensing agent.

Examples of the acid are an inorganic acid such as HCl and $H_2SO_4$, and a Lewis acid such as $BF_3$. It is preferable that such acids be employed in an amount of 0.1 to 10 equivalents to the carboxylic acid derivative of formula (II-1).

As the condensing agent, for example, "DCC" can be employed. When such a condensing agent is employed, it is preferable that the amount of the condensing agent be 1 to 2 equivalents for the carboxylic acid derivative of fromula (II-1). When "DCC" is used as a condensing agent, a base such as N,N-dimethylaminopyridine may also be used, preferably in an amount of 0.1 to 1 equivalent to the "DCC".

The above reaction can be carried out in an inactive solvents such as benzene, toluene, dichloromethane, chloroform, acetonitrile, dichloroethane or acetone. In order to carry out the reaction smoothly, it is preferable that the reaction temperature be in the range of 0°–120° C.

The reaction of the halogen-substituted carboxylic acid compounds or the active ester compounds with the alcohol derivative of formula (II-2) can be carried out in inactive solvents, for example, aromatic hydrocarbons such as benzene and toluene, halogenated hydrocarbon such as chloroform and dichloromethane, amides such as dimethylformamide, and nitriles such as acetonitrile.

In order to carry out the above reaction smoothly, it is preferable that a base such as N,N-dimethylaminopyridine and trimethylamine be added to the reaction mixture, in an amount of 0.1 to 2 equivalents to the carboxylic acid derivative. The reaction is usually carried out at −70° C. to 100° C., preferably at −20° C. to 50° C.

Process B

In this process, the optical active 1,4-dihydropyridine derivative of formula (II) is prepared by allowing a β-ketocarboxylic acid ester derivative of formula (II-3) to react with an optical active β-aminoacrylic acid ester derivative of formula (II-4) and then by allowing the reaction product to react with an amine or an acid-added salt thereof.

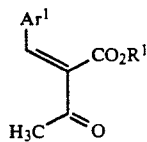
(II-3)

wherein $Ar^1$ and $R^1$ are respectively the same as those defined in formula (II-1).

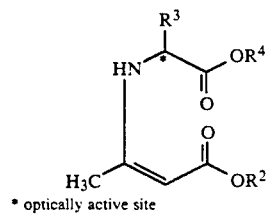
(II-4)

* optically active site wherein $R^2$ is the same as defined in formula (II-1), and $R^3$ and $R^4$ each represents an alkyl group having 1 to 6 carbon atoms, a phenyl group or a benzyl group.

The β-ketocarboxylic acid ester derivative of formula (II-3) can be obtained by reacting an aromatic aldehyde derivative and a counterpart acetoacetic ester.

Specific example of the β ketocarboxylic acid ester derivative of formula (II-3) are:
methyl 2-(2-nitrobenzylidene)acetoacetate,
methyl 2-(3-nitrobenzylidene)acetoacetate,
methyl 2-(4-nitrobenzylidene)acetoacetate,
ethyl 2-(3-nitrobenzylidene)acetoacetate,
n-propyl 2-(3-nitrobenzylidene)acetoacetate,
isopropyl 2-(3-nitrobenzylidene)acetoacetate,
2-methoxyethyl 2-(3-nitrobenzylidene)acetoacetate,
2,4-hexadienyl 2-(3-nitrobenzylidene)acetoacetate,
3-pbenyl-2-propen-1-yl 2-(3-nitrobenzylidene)acetoacetate,
3-[4-(1-imidazolylmethyl)phenyl3-2-propen-1-yl 2-(3-nitrobenzylidene)acetoacetate.
methyl 2-benzylideneacetate,
methyl 2-(2-cyanobenzylidene)acetoacetate,
methyl 2-(2,3-dicyclobenzylidene)acetoacetate,
methyl 2-(furylmethylene)acetoacetate,
methyl 2-(thienylmethylene)acetoacetate,
methyl 2-(naphthylmethylene)acetoacetate,
methyl 2-(quinolylmethylene)acetoacetate,
methyl 2-(3-azidobenzylidene)acetoacetate,
methyl 2-(3-trifuroromethylbenzylidene)acetoacetate,
methyl 2-(4-methoxybenzylidene)acetoacetate,
methyl 2-(4-methylbenzylidene)acetoacetate,
methyl 2-(4-methylthiobenzylidene)acetoacetate, and
methyl 2-(pyridylmethylene)acetoacetate.

In order to carry out the reaction smoothly, it is preferable to employ a catalyst. Examples of the catalyst include piperidine salts such as piperidine acetate. It is preferable that this reaction be carried out in solvents, for example, aromatic hydrocarbons such as benzene and toluene, nitriles such as acetonitrile, halogenated hydrocarbons such as dichloromethane and dichloroethane, alcohols such as methanol, ethanol and isopropyl alcohol, and ethers such as diisopropyl ether. The reaction is usually carried out at 0°–100° C., preferably at 10°–70° C.

The optical active β-aminoacrylic acid ester derivative of formula (II-4) can be obtained by mixing the corresponding acetoacetic ester and amino acid ester.

Specific examples of the optical active β-aminoacrylic acid ester derivative of formula (II-4) for use in the present invention are as follows:
methyl (S)-(+)-N-[(1-t-butoxycarbonyl-2-methyl)propyl]aminocrotonate,
methyl (R)-(−)-N-[(1-t-butoxycarbonyl-2-methyl)propyl]aminocrotonate,
methyl (S)-(+)-N-[(1-ethoxycarbonyl-2-methyl)propyl]aminocrotonate,
methyl (R)-(−)-N-[(1-ethoxycarbonyl-2-methyl)propyl]aminocrotonate,
methyl (S)-(+)-N-[(1-methoxycarbonyl-2-methyl)propyl]aminocrotonate,
methyl (R)-(−)-N- [1-methoxycarbonyl-2-methyl)propyl]aminocrotonate,
methyl (S)-(+)-N-[(1-cyclohexyloxycarbonyl-2-methyl)propyl]aminocrotonate,
methyl (R)-(−)-N-[(1-cyclohexyloxycarbonyl-2-methyl)propyl]aminocrotonate,
methyl (S)-(+)-N-[(1-isopropyloxycarbonyl-2-methyl)propyl]aminocrotonate,
methyl (R)-(−)-N-[(1-isopropyloxycarbonyl-2-methyl)propyl]aminocrotonate,
methyl (S)-(+)-N-(1-t-butoxycarbonylethyl)aminocrotonate,
methyl (R)-(−)-N-(1-t-butoxycarbonylethyl)aminocrotonate,
methyl (S)-(+)-N-[(1-t-butoxycarbonyl-2,2-dimethyl)propyl]aminocrotonate,
methyl (R)-(−)-N-[(1-t-butoxycarbonyl-2,2-dimethyl)propyl]aminocrotonate,
methyl (S)-(+)-N-[(1-t-butoxycarbonylmethyl)butyl]aminocrotonate,
methyl (R)-(−)-N-[(1-t-butoxycarbonyl-3-methyl)butyl]aminocrotonate,
methyl (S)-(+)-N-[(1-t-butoxycarbonyl-1-phenyl)methyl]aminocrotonate,
methyl (R)-(−)-N-[(1-t-butoxycarbonyl-1-phenyl)methyl]aminocrotonate,@
methyl (S)-(+)-N-[(1-t-butoxycarbonyl-2-phenyl)ethyl]aminocrotonate,
methyl (R)-(−)-N-[(1-t-butoxycarbonyl-2-phenyl)ethyl]aminocrotonate,
ethyl (S)-(+)-N-1(1-t-butoxycarbonyl-2-methyl)propyl]aminocrotonate,
ethyl (R)-(−)-N-[(1-t-butoxycarbonyl-2-methyl)propyl]aminocrotonate,
n-propyl (S)-(+)-N-[(1-t-butoxycarbonyl-2-methyl)propyl]aminocrotonate,
n-propyl (R)-(−)-N-[(1-t-butoxycarbonyl-2-methyl)propyl]aminocrotonate,
isopropyl (S)-(+)-N-[(1-t-butoxycarbonyl-2-methyl)propyl]aminocrotonate,
isopropyl (R)-(−)-N-[(1-t-butoxycarbonyl-2-methyl)propyl]aminocrotonate,
2-methoxyethyl (S)-(+)-N-[(1-t-butoxycarbonyl-2-methyl)propyl]aminocrotonate, 2-methoxyethyl (R)-(−)-N-[(1-t-butoxycarbonyl-2-methyl)propyl]aminocrotonate,
3-phenyl-2-propen-1-yl (S)-(+)-N-[(1-t-butoxycarbonyl-2-methyl)propyl]aminocrotonate,
3-phenyl-2-propen-1-yl (R)-(−)-N-[(1-t-butoxycarbonyl-2-methyl)propyl]aminocrotonate,
(E)-3-[4-(1-imidazolylmethyl)phenyl]-2-propen-1-yl -(S)-(+)-N-[(1-t-butoxycarbonyl-2-methyl)propyl-]aminocrotonate,
(E)-3-[4-(1-imidazolylmethyl)phenyl]-2-propen-1-yl (R)-(−)-N-[(1-t-butoxycarbonyl-2-methyl)propyl-]aminocrotonate,
(Z)-3-[4-(1-imidazolylmethyl)phenyl]-2-propen-1-yl (S)-(+)-N-[(1-t-butoxycarbonyl-2-methyl)propyl-]aminocrotonate,
(Z)-3-[4-(1-imidazolylmethyl)phenyl]-2-propen-1-yl (R)-(−)-N-[(1-t-butoxycarbonyl-2-methyl)propyl-]aminocrotonate,
3-[4-(1-imidazolylmethyl)phenyl]-2-propen-1-yl (S)-(+)-N-[(1-ethoxycarbonyl-2-methyl) propyl]aminocrotonate,
3-[4-(1-imidazolylmethyl)phenyl]-2-propen-1-yl (R)-(−)-N-[(1-ethoxycarbonyl-2-methyl) propyl]aminocrotonate,
3-[4-(1-imidazolylmethyl)phenyl]-2-propen-1-yl (S)-(+)-N-[(1-cyclohexyloxycarbonyl-2-methyl)-propyl]aminocrotonate,
3-[4-(1-imidazolylmethyl)phenyl]-2-propen-1yl (S)-(+)-N-[4-(1-cyclohexyloxycarbonyl -2-methyl)propyl-]aminocrotonate,
3-[4-(1-imidazolylmethyl)phenyl]2propen-1-yl (R)-(−)-N-[(1-cyclohexyloxycarbonyl-2-methyl)propyl-]aminocrotonate,
3-[4-(1-imidazolylmethyl)phenyl]-2-propen-1-yl (S)-(+)-N-[(1-isopropyloxycarbonyl-2-methyl)-propyl]aminocrotonate,
3-[4-(1-imidazolylmethyl)phenyl]-2-propen-1-yl (R)-(−)-N-[(1-isopropyloxycarbonyl-2-methyl)propyl-]aminocrotonate,
3-[4-(1-imidazolylmethyl)phenyl]-2-propen-1-yl (S)-(+)-N-([(1-t-butoxycarbonylethyl) aminocrotonate,
3[-4-(1-imidazolylmethyl)phenyl]-2-propen-1-yl (R)-(−)-N-(1-t-butoxycarbonylethyl) aminocrotonate,
3[-4-(1-imidazolylmethyl)phenyl]-2-propen-1-yl (S)-(+)-N-[(1-t-butoxycarbonyl-2,2-dimethyl)-propyl]aminocrotonate,
3-[4-(1-imidazolylmethyl)phenyl]-2-propen-1-yl (R)-(−)-N-[(1-t-butoxycarbonyl-2,2-dimethyl)propyl-]aminocrotonate,
3-[4-(1-imidazolylmethyl)phenyl]-2-propen-1-yl (S)-(+)-N-[(1-t-butoxycarbonyl-3-methyl) butyl-]aminocrotonate,
3-[4-(1-imidazolylmethyl)phenyl]-2-propen-1-yl (R)-(−)-N-[(1-t-butoxycarbonyl-3-methyl) butyl]aminocrotonate,
3-[4-(1-imidazolylmethyl)phenyl]-2-propen-1-yl (S)-(+)-N-[(1-t-butoxycarbonyl-1-phenyl) methyl-]aminocrotonate,
3-[-4-(1-imidazolylmethyl)phenyl]-2-propen-1-yl (R)-(−)-N-[1(1-t-butoxycarbonyl-1-phenyl)methyl-]aminocrotonate,
3-[4-(1-imidazolylmethyl)phenyl]-2-propen-1-yl (S)-(+)-N-[1(1-t-butoxycarbonyl-2-phenyl)ethyl-]aminocrotonate,
3-[4-(1-imidazolylmethyl)phenyl]-2-propen-1-yl (R)-(−)-N-[(1-t-butoxycarbonyl-2-phenyl) ethyl]aminocrotonate,
3-[4-(3-pyridylmethyl)phenyl]-2-propen-1-yl (S)-(+)-N-[(1-t-butoxycarbonyl-2-methyl) propyl]aminocrotonate,
3-[4-(3-pyridylmethyl)phenyl]-2-propen-1-yl (R)-(−)-N-[(1-t-butoxycarbonyl-2-methyl) propyl]aminocrotonate,
3-[4-(1,2,4-triazole-1-yl-methyl)phenyl]-2-propen-1-yl (S)-(+)-N-[(1-t-butoxycarbonyl-2-methyl)propyl-]aminocrotonate,
3-[4-(1,2,4-triazole-1-yl-methyl)phenyl]-2-propen-1-yl (R)-(−)-N-[(1-t-butoxycarbonyl-2-methyl)propyl-]aminocrotonate,
3-[4-(1,2,3,4-tetrazole-1-yl-methyl)phenyl]-2-propen-1-yl (S)-(+)-N-[(1-t-butoxycarbonyl-2-methyl)-propyl]aminocrotonate,
3-[4-(1,2,3,4-tetrazole-1-yl-methyl)phenyl]-2-propen-1-yl (R)-(−)-N-[(1-t-butoxycarbonyl-2-methyl)-propyl]aminocrotonate,
3-[3-(1-imidazolylmethyl)phenyl]-2-propen-1-yl (S)-(+)-N-[(1-t-butoxycarbonyl-2-methyl)propyl-]aminocrotonate,
3-[3-(1-imidazolylmethyl)phenyl]-2-propen-1-yl (R)-(−)-N-[(1-t-butoxycarbonyl-2-methyl) propyl-]aminocrotonate,
3-[2-(1-imidazolylmethyl)phenyl]-2-propen-1-yl (S)-(+)-N-[(1-t-butoxycarbonyl-2-methyl) propyl-]aminocrotonate,
3-[2-(1-imidazolylmethyl)phenyl]-2-propen-1-yl (R)-(−)-N-[(1-t-butoxycarbonyl-2-methyl) propyl-]aminocrotonate,
3-[5-(1-imidazolylmethyl)furan]-2-propen-1-yl (S)-(+)-N-[(1-t-butoxycarbonyl-2-methyl) propyl]aminocrotonate,
3[-5-(1-imidazolylmethyl)furan)-2-propen-1-yl (R)-(−)-N-[(1-t-butoxycarbonyl-2-methyl) propyl]aminocrotonate,
3-[5-(1-imidazolylmethyl)thiophenel-2-propen-1-yl (S)-(+)-N-[(1-t-butoxycarbonyl-2-methyl) propyl-]aminocrotonate,
3[5-(1-imidazolylmethyl)thiophenel-2-propen-1-yl (R)-(−)-N-[(1-t-butoxycarbonyl-2-methyl) propyl-]aminocrotonate,
3[-2-(1-imidazolylmethyl)-1-methyl-pyrrole-5-yl]-2-propen-1-yl (S)-(+)-N-[(1-t-butoxycarbonyl-2-methyl)-propyl]aminocrotonate,
3-[2-(1-imidazolylmethyl)-1-methyl-pyrrole-5-yl]-2-propen-1-yl (R)-(−)-N-[(1-t-butoxycarbonyl-2-methyl)-propyl)aminocrotonate,
3-[4-[1-(1-imidazolyl)ethyl]phenyl]-2-propen-1-yl (S)-(+)-N-[(1-t-butoxycarbonyl -2-methyl)propyl-]aminocrotonate,
3-[4-[1-(1-imidazolyl)ethyl]ephenyl]-2-propen-1-yl (R)-(−)-N-[(1-t-butoxycarbonyl -2-methyl)propyl-]aminocrotonate,
3-[4-(1-imidazolyl)phenyl]-2-propen-1-yl (S)-(+)-N-[(1-t-butoxycarbonyl-2-methyl) propyl]aminocrotonate,
3[-4-(1-imidazolyl)phenyl]-2-propen-1-yl (R)-(−)-N-[(1-t-butoxycarbonyl-2-methyl) propyl]aminocrotonate,
3-[4-(1-imidazolylmethyl)phenyl)-2-propen-1-yl (S)-(+)-N-[(1-t-butoxycarbonyl-2-methyl) propyl-]aminocrotonate,
3-[4-(1-imidazolylmethyl)phenyl]-2-propen-1-yl (R)-(−)-N-[(1-t-butoxycarbonyl-2-methyl)propyl]aminocrotonate,
5[-4-(1-imidazolylmethyl)phenyl]-2,4-pentadiene-1-yl (S)-(+)-N-[(l-t-butoxycarbonyl-2-methyl)propyl-]aminocrotonate, 5-[4-(1-imidazolylmethyl)phenyl]-2,4-pentadiene-1-yl (R)-(−)-N-[(l-t-butoxycarbonyl-2-methyl)propyl]aminocrotonate, 4,5-dihydro-2-(1-imidazolylmethyl)thianaphthene-6-yl-methyl (S)-(+)-N-1(1-t-butoxycarbonyl-2-methyl)propyl]aminocrotonate, 4,5-dihydro-2-(1-imidazolylmethyl)thianaphthene-6-yl-methyl (R)-(−)-N-[(1-t-butoxycarbonyl-2-methyl)propyl]aminocrotonate, 4,5-dihydro-2-[α-(l-imidazolyl)benzyl]thianaphthene-6-yl-methyl (S)-(+)-N-[(1-t-butoxycarbonyl-2-methyl)propyl]aminocrotonate, 4,5-dihydro-2-[α-(1-imidazolyl)benzyl]thianaphthene-6-yl-methyl (R)-(−)-N-[(1-t-butoxycarbonyl-2-methyl)propyl]aminocrotonate, 3-[4-(imidazo-[1,2-a]pyridine-6-yl-methyl)phenyl]-2-propen-1-yl (S)-(+)-N-[(1-t-butoxycarbonyl-2-methyl)propyl]aminocrotonate, and 3-[4-(imidazo-[1,2-a]pyridine-6-yl-methyl)phenyl]-2-propen-1-yl (R)-(−)-N-[(1-t-butoxycarbonyl-2-methyl)propyl]aminocrotonate.

It is preferable that the reaction of the acetoacetic ester and amio acid ester for obtaining the optical active β-aminoacrylic acid ester derivative of formula (II-4) be carried out without solvents or in inactive solvents. Examples of the inactive solvents are aromatic hydrocarbons such as benzene and toluene, nitriles such as acetonitrile, halogenated hydrocarbons such as chloroform, and ethers such as tetrahydrofuran. The reaction is usually carried out at 0°-100° C., preferably at 10°-70° C.

The reaction of the 3-ketocarboxylic acid ester derivative of formula (II-3) with the optical active β-aminoacrylic acid ester derivative of formula (II-4) for obtaining the optical active 1,4-dihydropyridine derivative of formula (II) can be carried out by reacting both components. In order to carry out the reaction smoothly, it is preferable to add a base to the reaction mixture. Examples of the base include n-butyl lithium, lithium diisoprolylamide, phenyl magnesium halide, metal sodium, and sodium hydride. It is preferable that the amount of the base be 0.5 to 1.5 equivalents to the optical active β-aminoacrylic acid ester derivative of formula (II-4).

Furthermore it is preferable that the above reaction be carried out in non-protonic solvents, for example, ether solvents such as diethyl ether and tetrahydrofuran, and aromatic solvents such as benzene and toluene. The reaction is usually carried out at −120° C. to 150° C., preferably −90° C. to −20° C.

In order to increase the yield of the reaction product, it is preferable that the reaction be carried out under an anhydrous condition and under an inert atmosphere by using an inert gas such as a nitrogen gas and an argon gas.

The reaction product obtained by the above reaction is so easily decomposed at room temperature that it is extremely difficult to identify the chemical structure. However, a mass spectrum of the reaction product indicates the chemical structure thereof is as shown below:

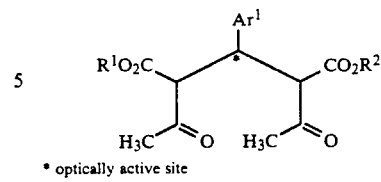

* optically active site wherein $Ar^1$, $R^1$ and $R^2$ are respectively the same as defined previously.

The above reaction product is allowed to react with an amine or an acid-added salt thereof, whereby an optical active 1,4-dihydropyridine derivative of formula (II) can be produced.

The amine and the acid-added salt thereof are, for example, ammonia, ammonium acetate, and ammonium chloride, which are industrially available.

In carrying out the reaction, the above mentioned amine can be used as a reaction solvent when used in an excessive amount. Alcohols such as ethanol, methanol and propanol, ethers such as diethyl ether and tetrahydrofuran, and hydrocarbons such as hexane, pentane, toulene and benzene, can also be employed as the reaction solvents.

The reaction is usually carried out at 0° C. to 60° C., preferably at room temperature because of the convenience for carrying out the reaction.

The product obtained by the above reaction is isolated and purified by extraction, recrystallization and chromatography in combination.

The optical active 1,4-dihydropyridine derivatives of formula (II) show a hypotensivie action in a test by using male spontaneously hypertensive rats (SHR), and an action of inhibiting KCl-induced contraction in aorta in a test by using thoracic aortas of rabbits.

Furthermore, the optical active 1,4-dihydropyridine derivatives of formula (II) show high inhibiting activities in a test of platelet aggregation-inhibiting activity in vitro by using rabbits.

EXAMPLE 36

(+)-3-[4-(1-imidazolylmethyl)phenyl]-2-propen-1-yl methyl-1,4-dihydro-2,6-dimethyl-4-(3-nitrophenyl)pyridine-3,5-dicarboxylate:

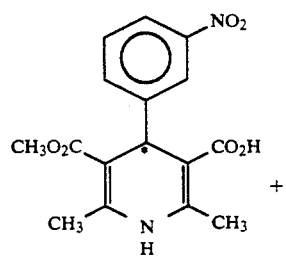
+
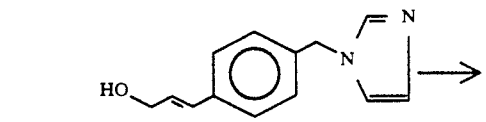

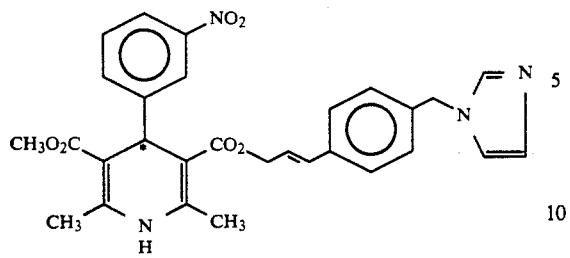

* optically active site 1.329 g (4 mM) of (−)-1,4-dihydro-2,6-dimethyl-5-methoxycarbonyl-4-(3-nitrophenyl)pyridine -3-carboxylic acid, 1.028 g (4.8 mM) of 3-[4-(1-imidazolylmethyl)phenyl]-2-propen-1-ol, 1.444 g (7 mM) of DCC, and 0.538 g (4.4 mM) of N,N-dimethylaminopyridine were mixed and refluxed in a dried dichloromethane for 5 hours. The solvent was distilled away, and the residue was purified by chromatography on a silica gel column, whereby the captioned compound was obtained. The yield was 1.898 g (89.8%).

Melting point (° C.): 175.0–176.6 (decomposed).

| Mass Spectrometric Analysis: | Molecular formula Calcd. Found | $C_{29}H_{28}N_4O_6$ 528.20085 528.19892 |
|---|---|---|
| $[\alpha]_D^{25} = +10.0°$ [c = 0.535, methanol] IR (cm$^{-1}$, KBr) | $\nu$CO $\nu NO_2$ | 1696 1528, 1350 |

NMR δCDCl$_3$: 2.37 (3H, s), 2.39 (3H, s), 3.64 (3H, s), 4.66 (1H, dd, J=14Hz), 4.76 (1H, dd, J=14Hz), 5.13 (2H, s), 5.13 (1H, s), 5.93 (1H, s), 6.23 (1H, dt. J=16Hz, 6 Hz), 6.50 (1H, d, J=16Hz), 6.93 (1H, s), 7.13 (2H, d, J=8Hz), 7.13 (1H, s), 7.33 (2H, d, J=8Hz), 7.35 (1H, t, J=8Hz), 7.64 (1Hz, d, J=8Hz), 7.69 (1H, s), 7.97 (1H, d, J=8Hz), 8.13 (1H, s).

EXAMPLE 37

(−)-3-14-(1-imidazolylmethyl)phenyl]-2-propen-1-yl methyl-1, 4-dihydro-2,6-dimethyl-4-(3-nitrophenyl)-pyridine-3,5-dicarboxylate:

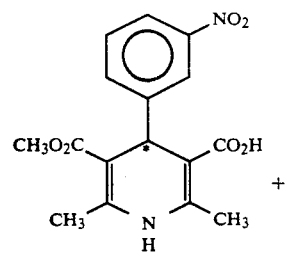

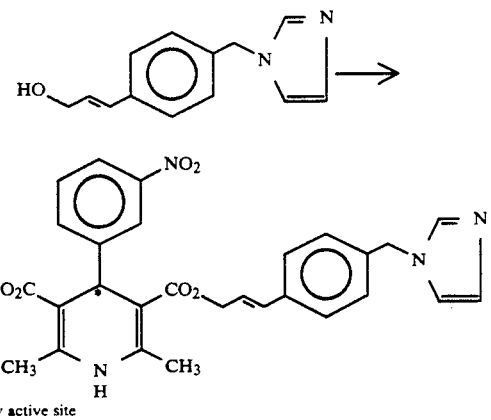

* optically active site 1.329 g (4 mM) of (+)-1,4-dihydro-2,6-dimethyl-5-methoxycarbonyl-4-(3-nitrophenyl)pyridine -3-carboxylic acid 1.028 g (4.8 mM) of 3-[4-(1-imidazolylmethyl)phenyl]-2-propen-1-ol, 1.444 (7 mM) of DCC, and 0.538 g (4.4 mM) of N,N-dimethylaminopyridine were mixed and refluxed in a dried dichloromethane for 5 hours. The solvent was distilled away, and the residue was purified by chromatography on a silica gel column, whereby the captioned compound was obtained. The yield was 1.860 g (88.0%).

Melting point (° C.): 175.8–176.3 (decomposed).

| Mass Spectrometric Analysis: | Molecular formula Calcd. Found | $C_{29}H_{28}N_4O_6$ 528.20085 528.19869 |
|---|---|---|
| $[\alpha]_D^{25} = -9.8°$ [c = 0.564, methanol] IR (cm$^{-1}$, KBr) | $\nu$CO $\nu NO_2$ | 1696 1528, 1350 |

NMR δCDCl$_3$: 2.37 (3H, s), 2.39 (3H, s), 3.64 (3H, s), 4.66 (1H, dd, J=14Hz, 7Hz), 4.76 (1H, dd, J=14Hz, 7Hz), 5.13 (2H, s), 5.13 (1H, s), 5.93 (1H, s), 6.23 (1H, dt. J=16Hz, 6 Hz), 6.50 (1H, d, J=16Hz), 6.93 (1H, s), 7.13 (2H, d, J=8Hz), 7.13 (1H, s), 7.33 (2H, d, J=8Hz), 7.35 (1H, t, J=8Hz), 7.64 (1Hz, d, J=8Hz), 7.69 (1H, s), 7.97 (1H, d, J=8Hz), 8.13 (1H, s).

EXAMPLE 38

(+)-3-[4-(1-imidazolylmethyl)phenyl]-2-propen-1-yl methyl-1,4-dihydro-2,6-dimethyl-4-(3-nitro-phenyl)-pyridine-3,5-dicarboxylate:

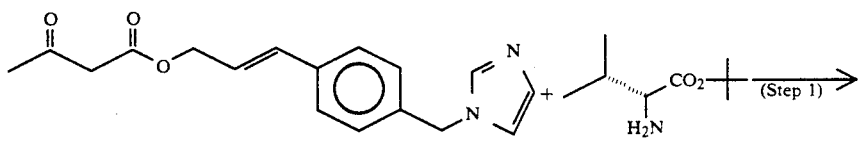

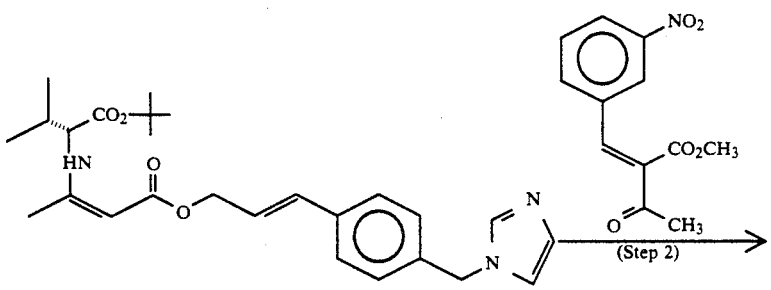

Step 1

0.416 g (2.4 mM) of D-valine-t-butyl ester was mixed with 0.597 g (2 mM) of 3-[4-(1-imidazolylmethyl)-phenyl]-2-propen-1-yl acetoacetate. The mixture was stirred for 24 hours. To this mixture, 10 ml of dried benzene was added.

The mixture was then dried over anhydrous sodium sulfurate. The benzene was then distilled away, whereby 3-[4-(1-imidazolylmethyl)phenyl]-2-propen-1-yl (−)-(R)-N-[(1-t-butoxycarbonyl-2-methyl) propyl]aminocrotonate was obtained. The yield was 0.898 g (99%).

$[\alpha]_D^{25} = -67.41$ [c=0.9595, CHCl$_3$].

NMR δCDCl$_3$ : 1.02 (6H, d, J=7Hz), 1.47 (9H, s), 1.88 (3H, s), 2.11–2.24 (1H, m), 3.79 (1H, dd, J=10Hz, 8Hz), 4.57 (1H, s), 4.73 (2H, d, J=7Hz), 5.11 (2H, s), 6.33 (1H, dt, J=17Hz, 7Hz), 6.61 (1H, d, J=17Hz), 6.90 (1H, s), 7.10 (2H, d, J=9Hz), 7.11 (1H, s), 7.37 (2H, d, J=9Hz), 7.61 (1H, s) 8.87 (1H, d, J=10Hz).

Step 2

0.898 g (1.98 mM) of 3-[4-(1-imidazolylmethyl)-phenyl]-2-propen-1-yl (−)-(R)-N-[(1-t-butoxycarbonyl-2-methyl)propyl]aminocrotonate was dissolved in 10 ml of dried tetrahydrofuran under an inert atmosphere using an Ar gas, and the solution was cooled to −75° C.

A tetrahydrofuran solution containing 1.2 equivalents of phenyl magnesium bromide, prepared from 77 mg (3.17 mg·atom), 75 mg (0.4 mM) of 1,2-dibromoethane, 374 mg (2.38 mM) of bromobenzene, and 5 ml of dried tetrahydrofuran, was added dropwise to the above solution. After the dropwise addition of the terahydrofuran solution, the mixture was stirred for 1 hour. To this mixture, a dried tetrahydrofuran solution containing 449 mg (1.8 mM) of 2-(3-nitrobenzylidene)acetoacetate was added dropwise.

After the above mixture was stirred at −75° C. for 20 hours, 5.4 ml of 1N HCl was added to the mixture and the temperature of the mixture was raised to room temperature. The mixture consisted of an organic layer and an aqueous layer.

The organic layer was separated from the mixture and the aqueous layer was extracted with tetrahydrofuran, and the tetrahydrofuran containing an extract was added to the organic layer. To this mixture, 5.4 ml of 1N HCl was added, and the mixture was stirred at room temperature for 3 hours. The mixture was extracted with chloroform. The chloroform containing an extract was dried over anhydrous sodium sulfate. The chloroform was distilled away from the mixture under reduced pressure, whereby an oily material was obtained.

The thus obtained oily material was dissolved in 10 ml of ethanol, and 700 mg (9 mM) of ammonium acetate was added thereto. The mixture was stirred at room temperature for 1 hour, and the ethanol was distilled away under reduced pressure to obtain a residue. The residue was dissolved in chloroform to form a solution. The solution was washed with a saturated aqueous solution of sodium hydrogen-carbonate, and then with water, and dried over anhydrous sodium sulfate. The chloroform was distilled away under reduced pressure. The residue was purified by chromatography on a silica gel column, and recrystallized from methanol, whereby the captioned compound was obtained. The yield was 713 mg (75%). The analysis data of this compound are exactly the same as those of the compound obtained in Example 36.

1. Test for hypotensive activity

The test was carried out by employing spontaneously hypertensive rats (aparalytic SHR; male) according to Nakao et al method.

300 μg/kg of the compound to be tested was administrated into the abdominal aorta of SHR through a canula (previously inserted). The blood pressures in the whole body of the rats were measured with a pressure transducer (MPU-0.5, made by Nihon Koden K. K.). The results are shown in Table 3.

TABLE 3

| Compounds | MaxΔMBP (mmHg) | Peak (min) | T½ (min) | HR (beats/min) |
|---|---|---|---|---|
| Example 36 | 51.4 | 0.9 | 3.4 | 49.0 |
| Example 37 | 10.8 | 0.6 | 0.4 | 3.7 |

2. Test for activity of inhibiting KCl-induced contraction Herical strips of thoracic aortas of rabbits (Japanese white rabbit; male) were mounted vertically in organ baths of Krebs-Henselit solution at 37° C. for 90 minutes, and then 30 mM of KCl was added to the baths. After 30 minutes, the compound to be tested was added to the baths, and the variations in the tension were recorded by an isometric kymograph, so that the inhibitory activity of the compound was determined in 60 minutes. The results of the test are shown in Table 4.

TABLE 4

| Compounds | Dosage (M) | N | Inhibitory Effect on KCl-induced contraction (%) |
|---|---|---|---|
| Example 36 | 3 × 10$^{-6}$ | 7 | 51.1 ± 11.6 |
| Example 37 | 3 × 10$^{-6}$ | 5 | 16.8 ± 9.8 |

*The dosage is determined in such a manner that the reaction mixture has the above molar concentration.

3. Test for platelet aggregation-inhibiting activity of rabbit

A blood of a rabbit (Japanese white; male; 2.5–3.0 kg) was exsanguinated from a carotid of the rabbit, and nine parts of the blood were mixed with one part of a 3.8% aqueous solution of sodium citrate. The mixture was centrifuged at 1100 rpm at 20° C. for 15 minutes. The upper layer is a platelet rich plasma (RRP), and the lower layer was centrifuged at 2500 rpm at 20° C. for 10 minutes, so that a platelet poor plasma (PPP) was obtained.

10 μl of a solution of the compound to be tested with a concentration of $10^{-4}$ mol/l was added to 200 μl of PRP, and the mixture was subjected to incubation for 30 minutes. To the mixture was added 10 μl of a platelet activating factor (PAF)(10 μg/ml), or arachidonic acid (AA)(1 mM at final concentration). The extent of the aggregation was measured by Agricometer (NKK, PAT-4A). The 50% Platelet aggregation-inhibiting concentration ($IC_{50}$ to each aggregation agent of each compound is shown in Table 5.

TABLE 5

| Compounds | $IC_{50}$ (M) | |
|---|---|---|
| | PAF (10 μg/ml) | AA (1 mM) |
| Example 36 | $1.1 \times 10^{-4}$ | $1.4 \times 10^{-4}$ |
| Example 37 | $3.2 \times 10^{-6}$ | $1.6 \times 10^{-4}$ |

What is claimed is:

1. A 1,4-Dihydropyridine derivative of formula (I):

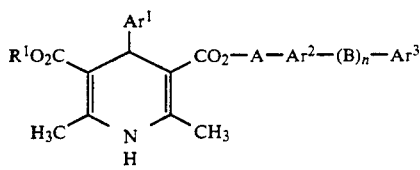

wherein $Ar^1$ is phenyl or naphthyl which may be substituted by one or more substituents selected from the group consisting of nitro, trihalomethyl, cyano, halo, phenoxy, azido, amido, alkoxy having 1 to 4 carbon atoms, alkyl having 1 to 4 carbon atoms, alkylthio, alkoxycarbonyl, and alkylcarbonyl; $R^1$ is (a) a straight, branched or cyclic saturated or unsaturated hydrocarbon which may be substituted by alkoxy having 1 to 6 carbon atoms, thioalkoxyl oralkylthio having 1 to 6 carbon atoms, amino or mono-or di-alkyl amino, halo, cyano, nitro, nitrato, hydroxyl, phenoxy, or phenylthio, or (b) alkenyl which may be substituted by an unsubstituted or substituted phenyl; A is a straight, branched or cyclic unsaturated hydrocarbon group, which may be substituted by halo, phenyl, cyano, alkylcarbonyl, or alkoxycarbonyl; $Ar^2$ is phenylene (o-,m- or p-); B is alkylene or alkenylene which may be substituted by alkyl having 1 to 4 carbon atoms, cycloalkyl, phenyl, naphthyl, or benzyl; $Ar^3$ is imidazolyl, which may be substituted by alkyl having 1 to 4 carbon atoms; and n is 1.

2. The 1,4 dihydropyridine derivative as claimed in claim 1, wherein said hydrocarbon represented by $R^1$ is alkyl having 1 to 6 carbon atoms.

3. The 1,4-dihydropyridine derivative as claimed in claim 1, wherein said straight or branched chain unsaturated hydrocarbon group represented by A is a straight chain or branched chain alkenylene or alkynylene.

4. The 1,4-dihydropyridine derivative as claimed in claim 1, wherein $Ar^1$ is phenyl which may have substituents selected from the group consisting of nitro, trihalomethyl, cyano, halo, phenoxy, azido, amido, alkoxy, having 1 to 4 carbon atoms, alkyl having 1 to 4 carbon atoms, alkylthio, alkoxycarbonyl, and alkylcarbonyl.

5. The 1,4-dihydropyridine derivative as claimed in claim 1, wherein $Ar^1$ is phenyl or naphthyl which may be substituted by one or more substituents selected from the group consisting of nitro, trihalomethyl, cyano, halo, and phenoxy.

6. The 1,4-dihydropyridine derivative as claimed in claim 1, wherein $Ar^1$ is selected from the group consisting of 2-nitrophenyl, 3-nitrophenyl, 4-nitrophenyl, 2-cyanophenyl, 2,3-dichlorophenyl, 1-naphthyl, 3-azidophenyl, 3-trifluoromethylphenyl, 4-methoxyphenyl, 4-methylthiophenyl, 4-methylphenyl and 3-trichloromethylphenyl.

7. The 1,4-dihydropyridine derivative as claimed in claim 1, wherein $R^1$ is selected from the group consisting of methyl, ethyl, propyl, n-butyl, n-pentyl, n-hexyl, isopropyl, isobutyl, cyclopentyl, cyclohexyl propenyl, 2-butenyl, 3-butenyl, 2-pentynyl, 2,4-hexadienyl, 2,4-hexadinyl, hexa-2-yn-4-ene, and hexa-2-en-4-yne.

8. The 1,4-dihydropyridine derivative as claimed in claim 1, wherein $R^1$ is selected from the group consisting of methoxyethyl, ethoxyethyl, methoxypropyl, ethoxypropyl, methylthioethyl, ethylthioethyl, methylthiopropyl, ethylthiopropyl, phenylthioethyl, 2-(N-methylamino)ethyl, and 2-(N,N-dimethylamino)ethyl.

9. The 1,4-dihydropyridine derivative as claimed in claim 1, wherein the straight or branched unsaturated hydrocarbon group represented by A has 3 to 12 carbon atoms.

10. The 1,4-dihydropyridine derivative as claimed in claim 1, wherein the cyclic unsaturated hydrocarbon group represented by A has 4 to 12 carbon atoms.

11. The 1,4-dihydropyridine derivative as claimed in claim 9, wherein the straight or branched unsaturated hydrocarbon group represented by A is selected from the group consisting of:

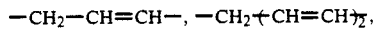

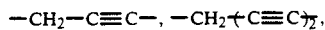

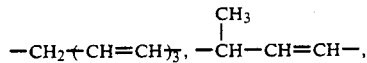

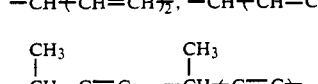

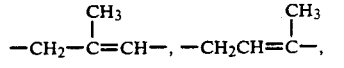

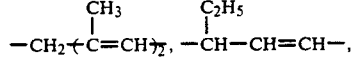

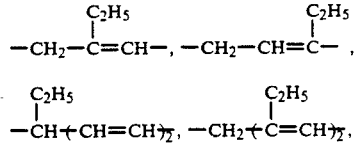

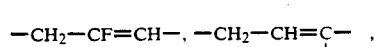

-continued

—CH₂—CH=CH—C≡C—, and

—CH₂—C≡C—CH=CH—.

12. The 1,4-dihydropyridine derivative as claimed in claim 1, wherein the alkylene or alkenylene group represented by B is selected from the group consisting of methylene, ethylene, trimethylene, ethylidene, benzylidene, vinylene, cychohexylmethylene and 2-phenylethylidene.

13. An optically active 1,4-dihydropyridine derivative having formula (II)

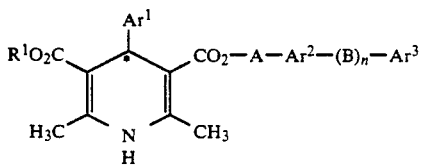

wherein $Ar^1$ is phenyl or naphthyl which may be substituted by one or more substituents selected from the group consisting of nitro, trihalomethyl, cyano, a halo, phenoxy, azido, amido, alkoxy having 1 to 4 carbon atoms, alkyl having 1 to 4 carbon atoms, alkylthio, alkoxycarbonyl and alkylcarbonyl; $R^1$ is (a) a straight, branched or cyclic saturated or unsaturated hydrocarbon which may be substituted by alkoxy having 1 to 6 carbon atoms, thioalkoxyl oralkylthio having 1 to 6 carbon atoms, amino or mono-or di-alkyl amino group, halo, cyano, nitro, nitrato, hydroxyl, phenoxy, or phenylthio, or (b) alkenyl which may be substituted by an unsubstituted or substituted phenyl; A is a straight, branched or cyclic unsaturated hydrocarbon group, which may be substituted by halo, phenyl, cyano, alkylcarbonyl, or alkoxycarbonyl; $Ar^2$ is phenylene (o-, m- or p-); B is alkylene or alkenylene which may be substituted by alkyl having 1 to 4 carbon atoms, cycloalkyl, phenyl, naphthyl or benzyl group, and $Ar^3$ is imidazolyl, which may be substituted by alkyl having 1 to 4 carbon atoms, and n is 1 and * indicates an optically active site.

14. The 1,4-dihydropyridine derivative as claimed in claim 13, wherein said hydrocarbon represented by $R^1$ is alkyl having 1 to 6 carbon atoms.

15. The 1,4-dihydropyridine derivative as claimed in claim 13, wherein said straight or branched chain unsaturated hydrocarbon group represented by A is a straight chain or branched chain, alkenylene or alkynylene.

16. The 1,4-dihydropyridine derivative as claimed in claim 13, wherein $Ar^1$ is phenyl which may have substituents selected from the group consisting of nitro, trihalomethyl, cyano, halo, phenoxy, azido, amido, alkoxy having 1 to 4 carbon atoms, alkyl having 1 to 4 carbon atoms, alkylthio, alkoxycarbonyl and alkylcarbonyl.

17. The 1,4-dihydropyridine derivative as claimed in claim 13, wherein $Ar^1$ is phenyl or naphthyl which may be substituted by one or more substituents selected from the group consisting of nitro, trihalomethyl, cyano, halogen, and phenoxy.

18. The 1,4-dihydropyridine derivative as claimed in claim 13, wherein $Ar^1$ is selected from the group consisting of 2-nitrophenyl, 3-nitrophenyl, 4-nitrophenyl, 2-cyanophenyl, 2,3-dichlorophenyl, 1-naphthyl, 3-azidophenyl, 3-trifluoromethylphenyl, 4-methoxyphenyl, 4-methylthiophenyl, 4-methylphenyl and 3-tricloromethylphenyl.

19. The 1,4-dihydropyridine derivative as claimed in claim 13, wherein $R^1$ is selected from the group consisting of methyl, ethyl, propyl, n-butyl, n-pentyl, n-hexyl, isopropyl, isobutyl, cyclopentyl, cyclohexyl propenyl, 2-butenyl, 3-butenyl, 2-pentynyl, 2,4-hexadienyl, 2,4-hexadinyl, hexa-2-yn-4ene, and hexa-2-en-4-yne.

20. The 1,4-dihydropyridine derivative as claimed in claim 13, wherein $R^1$ is selected from the group consisting of methoxyethyl, ethoxyethyl, methoxypropyl, ethoxypropyl, methylthioethyl, ethylthioethyl, methylthiopropyl, ethylthiopropyl, penenylthioethyl, 2-(N-methylamino)ethyl, and 2-(N,N-dimethylamino)ethyl.

21. The 1,4-dihydropyridine derivative as claimed in claim 13, wherein the straight or branched unsaturated hydrocarbon group represented by A has 3 to 12 carbon atoms.

22. The 1,4-dihydropyridine derivative as claimed in claim 13, wherein the cyclic unsaturated hydrocarbon group represented by A has 4 to 12 carbon atoms.

23. The 1,4-dihydropyridine derivative as claimed in claim 21, wherein the straight or branched unsaturated hydrocarbon group represented by A is selected from the group consisting of:

—CH₂—CH=CH—, —CH₂╌(CH=CH)₂,

—CH₂—C≡C—, —CH₂╌(C≡C)₂, $$\underset{\text{CH}_3}{|}$$
—CH₂╌(CH=CH)₃, —CH—CH=CH—, $$\underset{\text{CH}_3}{|} \quad \underset{\text{CH}_3}{|}$$
—CH╌(CH=CH)₂, —CH╌(CH=CH)₃, $$\underset{\text{CH}_3}{|} \quad \underset{\text{CH}_3}{|}$$
—CH—C≡C—, —CH╌(C≡C)₂, $$\underset{\text{CH}_3}{|} \quad \underset{\text{CH}_3}{|}$$
—CH₂—C=CH—, —CH₂CH=C—, $$\underset{\text{CH}_3}{|} \quad \underset{\text{C}_2\text{H}_5}{|}$$
—CH₂╌(C=CH)₂, —CH—CH=CH—, $$\underset{\text{C}_2\text{H}_5}{|} \quad \underset{\text{C}_2\text{H}_5}{|}$$
—CH₂—C=CH—, —CH₂—CH=C—, $$\underset{\text{C}_2\text{H}_5}{|} \quad \underset{\text{C}_2\text{H}_5}{|}$$
—CH╌(CH=CH)₂, —CH₂╌(C=CH)₂, —CH₂—CF=CH—, —CH₂—CH=C— 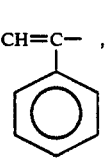, —CH₂—CH=CH—C≡C—, and

—CH₂—C≡C—CH=CH—.

24. The 1,4-dihydropyridine derivative as claimed in claim 13, wherein the alkylene or alkenylene group represented by B is selected from the group consisting of methylene, ethylene, trimethylene, ethylidene, benzylidene, vinylene, cychohexylmethylene and 2-phenylethylidene.